United States Patent
Kodadek et al.

(10) Patent No.: US 8,334,239 B2
(45) Date of Patent: Dec. 18, 2012

(54) HIGH AFFINITY VEGF-RECEPTOR ANTAGONISTS

(75) Inventors: Thomas Kodadek, Dallas, TX (US); D. Gomika Udugamasooriya, Coppell, TX (US); Rolf Brekken, Dallas, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 839 days.

(21) Appl. No.: 12/166,042

(22) Filed: Jul. 1, 2008

(65) Prior Publication Data

US 2009/0246124 A1 Oct. 1, 2009

Related U.S. Application Data

(60) Provisional application No. 60/948,845, filed on Jul. 10, 2007.

(51) Int. Cl.
C40B 30/04 (2006.01)
(52) U.S. Cl. .......................................................... 506/9
(58) Field of Classification Search ....................... 506/9
See application file for complete search history.

(56) References Cited

U.S. PATENT DOCUMENTS

| | | | |
|---|---|---|---|
| 5,510,240 A | 4/1996 | Lam et al. | 435/7.1 |
| 6,342,219 B1 | 1/2002 | Thorpe et al. | 424/145.1 |
| 6,342,221 B1 | 1/2002 | Thorpe et al. | 424/178.1 |
| 6,416,758 B1 | 7/2002 | Thorpe et al. | 424/145.1 |
| 6,524,583 B1 | 2/2003 | Thorpe et al. | 424/145.1 |
| 6,613,582 B1 | 9/2003 | Kodadek et al. | 424/524 |
| 6,617,114 B1* | 9/2003 | Fowlkes et al. | 506/10 |
| 6,676,941 B2 | 1/2004 | Thorpe et al. | 424/178.1 |
| 6,703,020 B1 | 3/2004 | Thorpe et al. | 424/178.1 |
| 6,783,760 B1 | 8/2004 | Thorpe et al. | 424/178.1 |
| 6,818,213 B1 | 11/2004 | Thorpe et al. | 424/130.1 |
| 6,887,468 B1 | 5/2005 | Thorpe et al. | 424/130.1 |
| 7,056,509 B2 | 6/2006 | Thorpe et al. | 424/145.1 |
| 7,067,109 B1 | 6/2006 | Thorpe et al. | 424/1.49 |
| 2002/0028457 A1* | 3/2002 | Empedocles et al. | 435/6 |
| 2004/0161798 A1 | 8/2004 | Kodadek | 506/9 |
| 2005/0089523 A1 | 4/2005 | Thorpe et al. | 424/178.1 |
| 2005/0123537 A1 | 6/2005 | Thorpe et al. | 424/143.1 |
| 2006/0083745 A1 | 4/2006 | Thorpe et al. | 424/155.1 |

OTHER PUBLICATIONS

Aina et al. Biopolymers (Pept. Sci.), 2002, vol. 66, pp. 184-199.*
Olivos et al. ChemBioChem, 2003, vol. 4, pp. 1242-1245.*
Alluri et al., "Isolation and characterization of coactivator-binding peptoids from a combinatorial library," *Mol. BioSystems.*, 2:568-579, 2006.
Alluri et al., "Isolation of protein ligands from large peptoid libraries," *J. Amer. Chem. Soc.*, 125:13995-14004, 2003.
Bachhawat-Sikder and Kodadek, "Mixed-element capture agents: a simple strategy for the construction of synthetic, high-affinity protein capture ligands," *J. Amer. Chem. Soc.*, 125:9550-9551, 2003.
Clark et al., "Safety and pharmacokinetics of the dual action Raf kinase and vascular endothelial growth factor receptor inhibitor, BAY 43/9006, in patients with advanced, refractory solid tumors," *Clin. Cancer Res.*, 11:5472-5480, 2005.
D'Andrea et al., "Peptide-based molecules in angiogenesis," *Chem. Biol. Drug Des.*, 67:115-126, 2006.
Gerber and Ferrara, "Pharmacology and pharmacodynamics of bevacizumab as monotherapy or in combination with cytotoxic therapy in preclinical studies," *Cancer Res.*, 65:671-680, 2005.
Getmanova et al., "Antagonists to human and mouse vascular endothelial growth factor receptor 2 generated by directed protein evolution in vitro," *Chem. Biol.*, 13:549-556, 2006.
Hicklin and Ellis, "Role of the vascular endothelial growth factor pathway in tumor growth and angiogenesis," *J. Clin. Oncol.*, 23:1011-1027, 2005.
Liu et al., "A potent transactivation domain mimic with activity in living cells," *J. Amer. Chem. Soc.*, 127:8254-8255, 2005.
Liu et al., "HIV entry inhibitors targeting gp41: from polypeptides to small-molecule compounds," *Curr. Pharm. Des.*, 13:143-162, 2007.
Peng et al., "Combinatorial chemistry identifies high-affinity peptidomimetics against alpha4beta1 integrin for in vivo tumor imaging," *Nature Chem. Biol.*, 2:381-389, 2006.
Reddy et al., "Transformation of low-affinity lead compounds into high-affinity protein capture agents," *Chem. Biol.*, 11:1127-1137, 2004.
Udugamasooriya et al., A peptoid antagonist of VEGF receptor 2 recognizes a 'hotspot' in the extracellular domain distinct from the hormone-binding site, *Bioorg. Med. Chem.*, 16:6338-43, 2008.
Udugamasooriya et al., "A peptoid "antibody surrogate" that antagonizes VEGF receptor 2 activity," *J. Am. Chem. Soc.*, 130:5744-52, 2008.
Zuckermann et al., "Discovery of nanomolar ligands for 7-transmembrane G-protein-coupled receptors from a diverse N-(substituted)glycine peptoid library," *J. Med. Chem.*, 37:2678-2685, 1994.

* cited by examiner

*Primary Examiner* — James D Anderson
(74) *Attorney, Agent, or Firm* — Parker Highlander PLLC

(57) ABSTRACT

A cell-based screen is reported can be used to identify specific receptor-binding compounds in a combinatorial library of peptoids (N-alkylglycine oligomers) displayed on beads. This strategy was applied to the isolation of Vascular Endothelial Growth Factor Receptor 2 (VEGFR2)-binding peptoids, which were optimized to create lead compounds with high affinity for VEGFR2. One of these peptoids was shown to be an antagonist of VEGF-VEGFR2 interaction and receptor function.

19 Claims, 24 Drawing Sheets

FIG. 10A
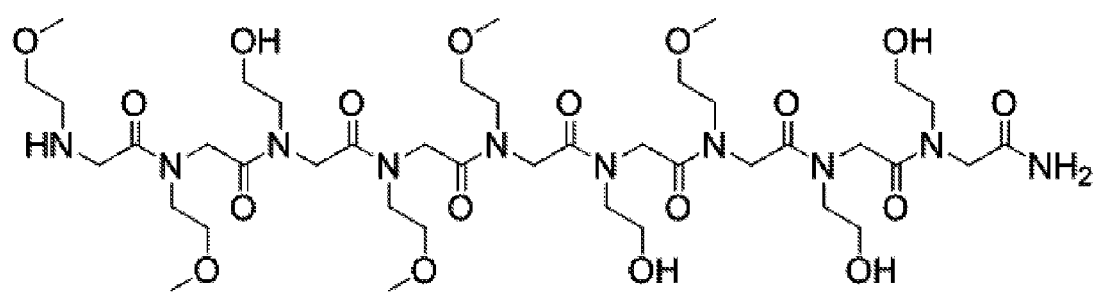
FIG. 10B
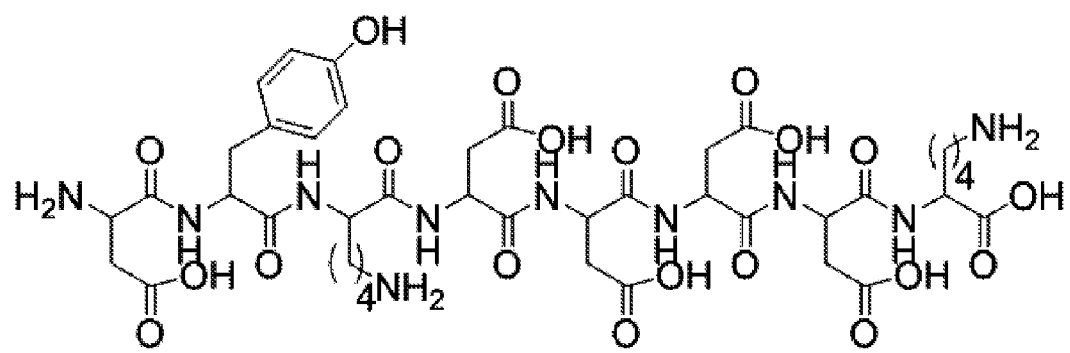
FIG. 10

GU40C

HIGH AFFINITY VEGF-RECEPTOR ANTAGONISTS

CROSS-REFERENCE TO RELATED APPLICATIONS

This application claims priority to U.S. Provisional Patent Application Ser. No. 60/948,845, filed Jul. 10, 2007, the entire contents of which are expressly incorporated herein by reference.

This invention was made with government support under N01-HV28185 awarded by National Heart, Lung and Blood Institute. The government has certain rights in the invention.

BACKGROUND OF THE INVENTION

1. Field of the Invention

The present invention relates to fields of peptide and peptoid chemistry, molecular biology and cell biology. More particularly, the present invention relates to peptidomimetics that antagonize the VEGF receptor and inhibit angiogenesis as well as methods with which to identify said antagonists. In particular, such inhibitors may find use in the treatment of diseases such as cancer and macular degeneration.

2. Description of Related Art

Monoclonal antibodies that antagonize the formation of various hormone receptor interactions are used widely in the clinic. For example, Remicade, and Adalimumab are anti-arthritic antibodies that block binding of Tumor Necrosis Factor (TNF)-α to its cognate receptor and thus reduce inflammation (Taylor, 2003). Avastin (Gerber and Ferrara, 2005), a Vascular Endothelial Growth Factor (VEGF)-binding antibody, prevents VEGF from docking with VEGF Receptor 2 (VEGFR2) (Hicklin and Ellis, 2005), a key step in the angiogenic cascade (Folkman, 1990) that is critical to support solid tumor survival and proliferation (Dvorak, 2002; Millauer et al., 1993; Zeng et al., 2001). Avastin is employed widely in the treatment of various tumors (Hurwitz et al., 2004; Johnson et al., 2004) and, more recently, to block blood vessel formation in "wet" macular degeneration (Ambresin and Mantel, 2007). While therapeutic monoclonal antibodies are obviously of great value, they are not without drawbacks. They are relatively difficult and expensive to manufacture in large quantities, there is some problem with immune reactions (Stevenson, 2005), though this has been minimized by humanization (Mateo et al., 2000).

Thus, it would be of great interest to develop relatively small, easily manipulable synthetic compounds that display antibody-like affinity and specificity for a given receptor, but which could be made cheaply and be easily tailored to carry cargo of various sorts. Unfortunately, it has traditionally proven difficult to isolate small molecule antagonists of protein-protein interactions, particularly those involving large, shallow interaction surfaces typical of hormone receptor complexes (Whitty and Kumaravel, 2006). While many examples are known of small molecules that act as agonists or antagonists of integral membrane receptors, these generally act by alternative mechanisms, for example as inhibitors of the ligand-activated kinase activity of the receptor (Cabebe and Wakelee, 2006; Ciardiello et al., 2003; Thomas, 2003). On the other hand, there are several examples of receptor- or hormone-binding peptide antagonists (D'Andrea et al., 2006). This is not surprising, since peptides are much better able to mimic the natural binding partner of a hormone or receptor than is a classical small molecule. In a few cases, these peptide antagonists have been developed into clinically useful compounds (Liu et al., 2007) but this approach to drug development is severely limited by the sensitivity of peptides to proteolysis. However, there remains a need in the field to develop agents that are able to antagonize those proteins involved with angiogenesis, particularly in the context of pathologic conditions that require the development of new blood vessels.

SUMMARY OF THE INVENTION

Thus, in accordance with the present invention, there is provided a method of antagonizing VEGFR, in particular VEGFR2, comprising contacting a cell containing the receptor with a compound having the formula:

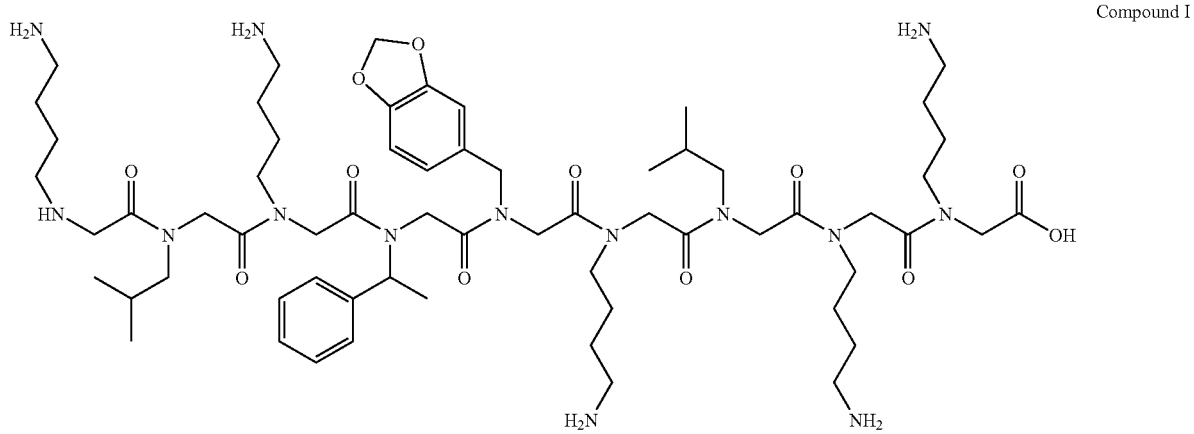

Compound I

The cell may be an endothelial cell, such as a vascular endothelial cell. The compound may comprise a dimer of the formula shown above, where two monomers are connected by a linker, as exemplified below:

cancer, a cervical cancer, a testicular cancer, a rectal cancer, an esophageal cancer, or a brain cancer. The cancer may be recurrent, metastatic or multi-drug resistant. The subject may be further administered a chemotherapeutic, radiotherapeu- Compound II

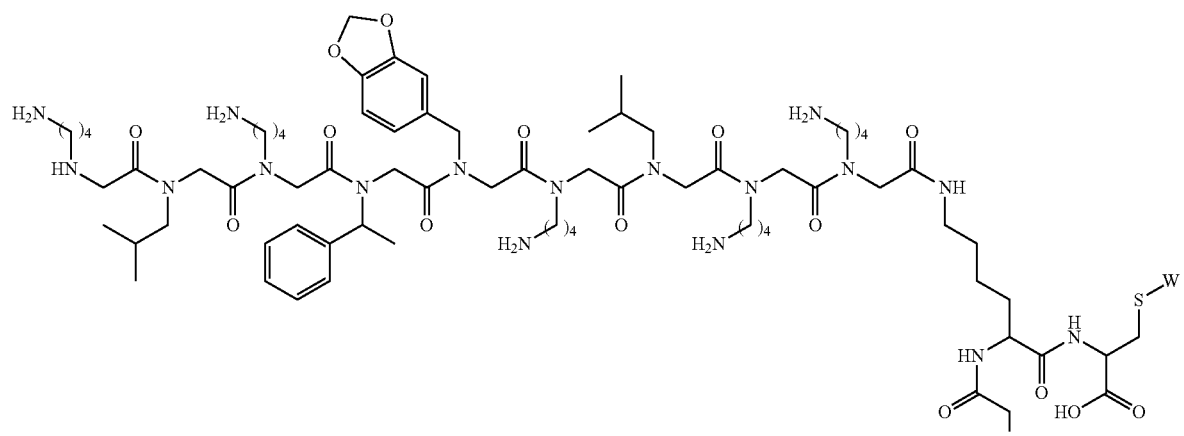

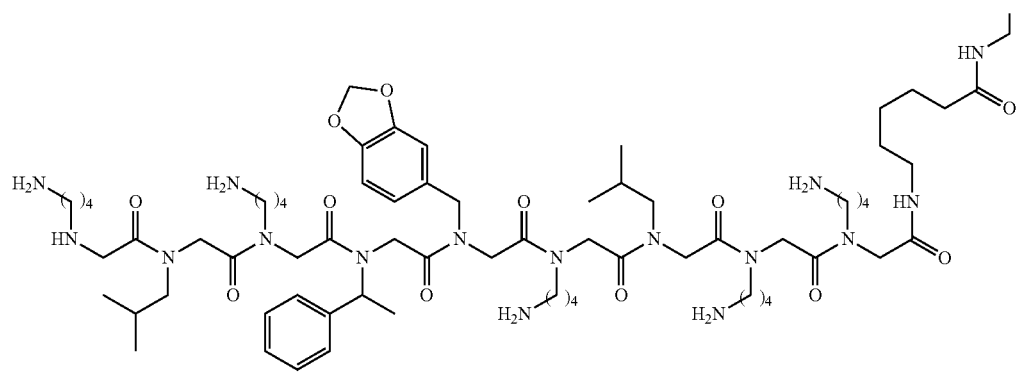

wherein W is defined as can be any arrangement of from 1-1000 carbon, hydrogen, nitrogen, sulfur, oxygen, chlorine, bromine, fluorine or silicon atoms, including, but not limited to biotin, fluorescein or other fluorescent molecules or any commonly used detectable moiety. Other linkers may also be utilized, and the foregoing linker is purely exemplary. The compound may be formulated in a lipid vehicle.

The cell may be located in a subject with cancer, and the vascular endothelial cell may be tumor-related, i.e., associated with the development of blood vessels feeding a solid tumor. The cancer may be a glioma, a sarcoma, or a myeloma. The cancer may also be a lung cancer, a skin cancer, a head & neck cancer, a stomach cancer, a breast cancer, a colon cancer, a pancreatic cancer, a liver cancer, an ovarian cancer, a uterine tic, immunotherapeutic or anti-cancer gene therapy. The compound may be delivered intravenously, intraarterially, subcutaneously, intra-tumorally, orally, by nasal inhalation, or any other suitable route given the location of the cancer cell.

The cell also may be located in a subject with a non-cancer hyperproliferative state, such as macular (wet) degeneration. Such treatments will generally follow those provided above for cancer, except that delivery may involve local administration to areas such as the eye, for example, by injection or by topical opthalmic solution. Combination therapies, using agents that are used to treated these other diseases also are contemplated.

Also provided is a pharmaceutical formulation comprising a compound having the structure:

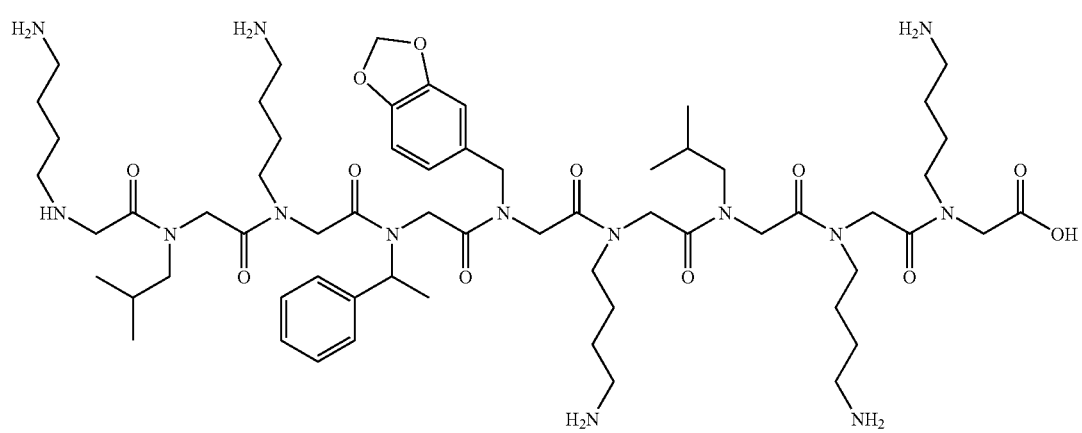

Compound I dispersed in a pharmacologically acceptable medium, diluent or excipient. The compound may comprise a homodimer of the formula shown above, where two monomers are connected by a linker, or a heterodimer of Compound I and Compound III, connected by a linker:

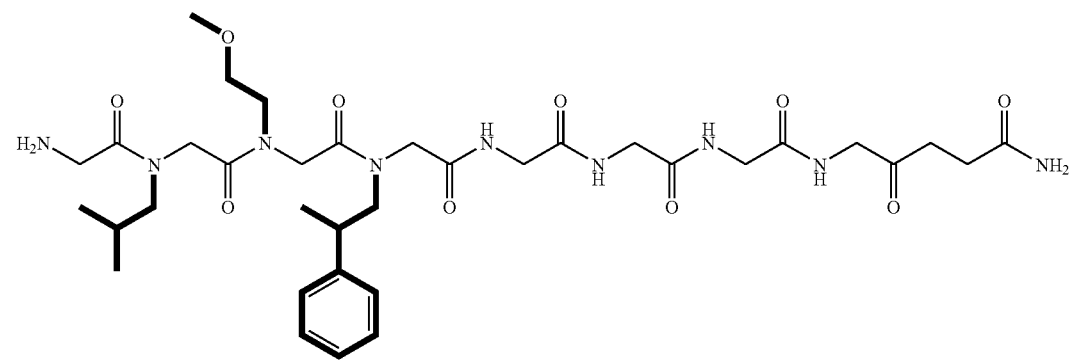

Compound III

The pharmacologic formulation may comprise a lipid formulation.

In yet another embodiment, there is provided a method of inhibiting VEFG signaling comprising contacting a cell expressing a VEGFR2 with a compound having the general formula:

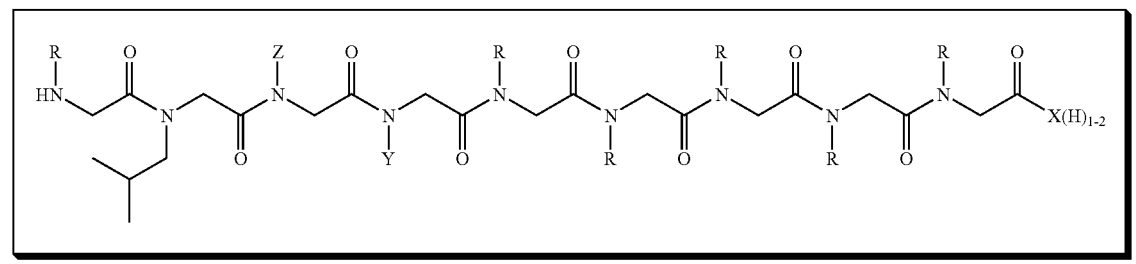

Formula I

-continued

X = O, N

Y = 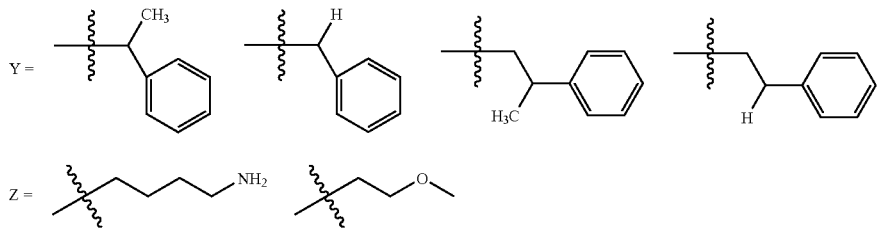

Z = wherein X, Y and Z are defined as shown above and R can be any arrangement of from 1-1000 carbon, hydrogen, nitrogen, sulfur, oxygen, chlorine, bromine, fluorine or silicon atoms, including, but not limited to H and $CH_3$.

The compound may comprise a dimer of the formula shown above, where two monomers are connected by a linker. R, X, Y and Z would be defined as above in Formula I, and W can be any arrangement of from 1-1000 carbon, hydrogen, nitrogen, sulfur, oxygen, chlorine, bromine, fluorine or silicon atoms, including, but not limited to biotin, fluorescein or other fluorescent molecules. Other linkers may also be utilized, and the foregoing linker is purely exemplary. Moreover, the dimer may be a homodimer comprised of identical monomeric units linked together (i.e., R, X, Y and Z are identical in the two linked units) or could be a heterodimer of two different molecules with non-identical R, X, Y, and Z groups. The atoms linking the two units of Formula II shown below are exemplary in nature, and other linker arms are not excluded:

Formula II

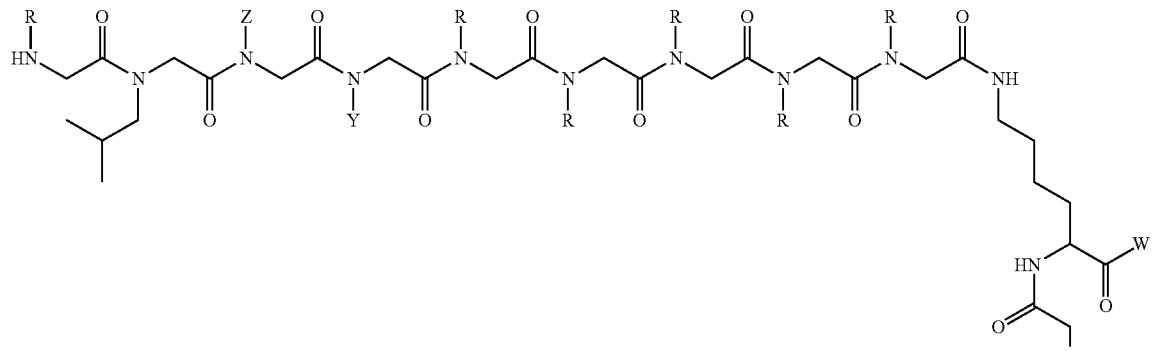

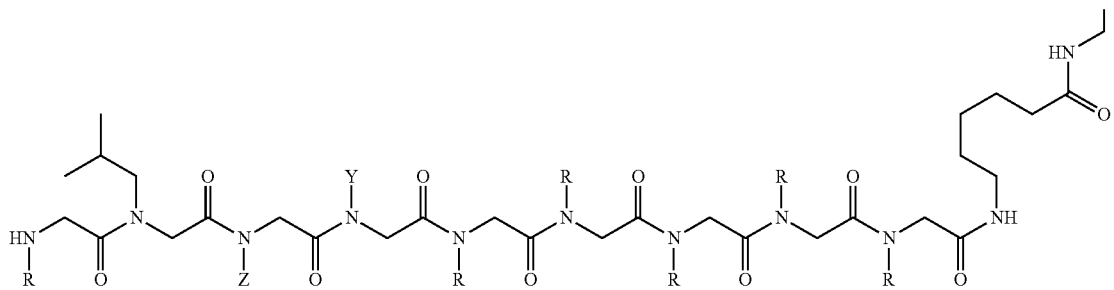

The compound may be formulated in a lipid vehicle. The cell may be an endothelial cell, such as a vascular endothelial cell. The human subject is contacted with said compound more than once The cell may be located in a human subject, for example, one that suffers from glioma, sarcoma or myeloma. Alternatively, the subject may suffer from lung cancer, skin cancer, head & neck cancer, stomach cancer, breast cancer, colon cancer, pancreatic cancer, liver cancer, ovarian cancer, uterine cancer, cervical cancer, testicular cancer, rectal cancer, esophageal cancer, or brain cancer. The compound may be formulated in a lipid vehicle. The human subject may further be treated with chemotherapeutic, radiotherapeutic, immunotherapeutic or anti-cancer gene therapy, such as a chemotherapeutic, radiotherapeutic, immunotherapeutic or anti-cancer gene therapy. The cancer may be recurrent, metastatic, or multi-drug resistant.

The human subject may alternatively suffer from a non-cancer disease characterized by abnormal or pathologic angiogenesis, such as macular (wet) degeneration. The human subject may be further treated with a second therapy for said non-cancer disease state.

In still yet another embodiment, there is provided a pharmaceutical formulation comprising a compound having the structure:

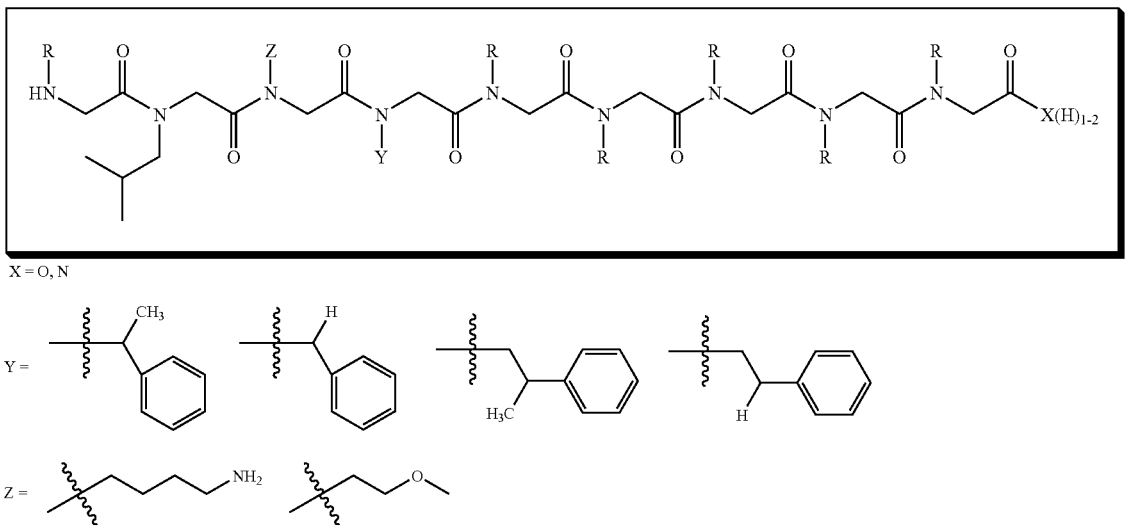

dispersed in a pharmacologically acceptable medium, diluent or excipient. R can be any arrangement of from 1-1000 carbon, hydrogen, nitrogen, sulfur, oxygen, chlorine, bromine, fluorine or silicon atoms, including, but not limited to H and $CH_3$ The compound may be a dimer of Formula I, said dimer comprising a linker that replaces the free —OH or —$NH_2$ group of each monomer. The compound may be a homodimer, or may be a heterodimer of two different compounds of Formula I, said homo- or heterodimer comprising a linker that replaces the —OH or —NH group of each monomer. The formulation may comprise a lipid formulation. The compound may have the structure:

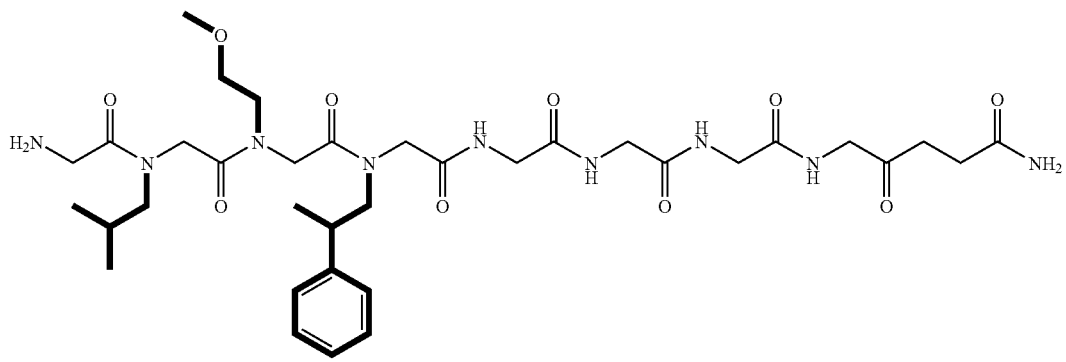

The compound may also have the structure:

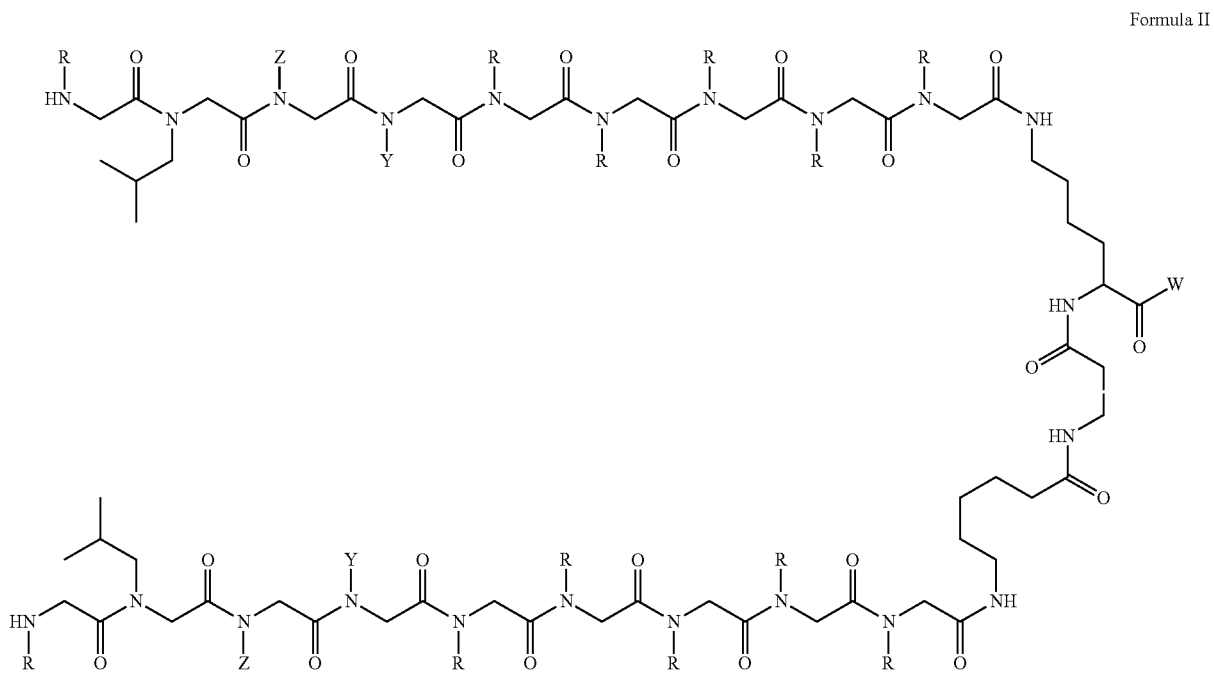

Formula II wherein R, W, Y and Z are defined as above.

There is also provided a method by which to identify molecules in a library that bind to a molecule displayed on the surface of a cell. This method is distinguished from existing protocols in that it demands that the isolated ligand have extremely high specificity for the target receptor.

As shown in FIG. 1, the method involves screening a library of compounds displayed on beads against a mixture of two cell types. The two cell types are identical except for the presence or absence of the target receptor (VEGFR2 in the case of FIG. 1). This is achieved by beginning with a cell type that does not naturally express the target receptor. These cells are labeled with a quantum dot or other appropriate dye of a given color. The target receptor is then expressed in this same cell type. The gene for the target receptor can be introduced in many different ways, for example by transfection, by virus-mediated integration or other methods known to those skilled in the art. The cells expressing the target receptor are labeled with a different colored quantum dot or appropriate dye. The two cell types, that differ solely in the presence or absence of the target receptor, are then mixed together. The mixed population is then treated so as to de-adhere the cells from the plate without destroying the cell surface receptors (i.e., proteolysis is avoided) and the "free" cells are incubated with the bead library. After a suitable incubation and washing, the beads are examined so as to distinguish those that bind ONLY the cells containing the target receptor and that do not bind the cells lacking the target receptor. This means that if the molecule displayed on the bead is capable of binding to any other molecule on the surface of the cell besides the target receptor, it will bind both red and green cells and thus be rejected as a potential hit.

The cells employed in this screen can be any cell that lacks the target receptor. This includes T cells, B cells, epithelial cells, kidney cells or any other culturable cell type. It also includes single celled organisms such as yeast or *Eschericia coli*. The target receptor may be any protein that exposes part of its structure on the cell surface so as to be accessible to cell impermeable molecules.

The method described may employ two different cells, one carrying the target receptor, the other not, labeled with two different colored dyes or may be carried out with multiple cells carrying different receptors and each labeled with a different colored dye. Such a multi-color assay would be useful in identifying compounds capable of distinguishing between very closely related receptors, for example VEGFR1 and VEGFR2 (see FIG. 24).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Schematic representation of the assay. The large blue circles represent peptoid library beads, the small red and green circles represent quantum dot-stained PAE/KDR (VEGFR2 over expressing) cells and PAE parental (lacking VEGFR2) cells, respectively. Beads that display peptoids that bind specifically to VEGFR2 should retain only red-stained cells. (FIG. 1B) Structure of the peptoid library employed in the screen, Top: general structure of all of the compounds inn the library (attached to bead via their C-terminal carboxyl group). Three residues (two Lys, and one Leu) at C-terminus were fixed and the remaining six residues (drawn in blue) were diversified (side chains represented by "R", drawn in red). Box: the amines employed to make the library. The nitrogen shown in blue becomes the main chain nitrogen in the peptoid. (FIG. 1C) and (FIG. 1D) Fluorescence microscopic images of select beads after screening and washing (10× magnification; DAPI filter). The arrows in (FIG. 1C) indicate beads that bind both cells that do and do not express VEGFR2. The bead indicated by the arrow in (FIG. 1D) represents one of five out of ≈300,000 observed to bind only red-stained cells.

(FIG. 4A) General chemical structure of the dimeric compounds tested. Longer dimeric compounds (GU40C1-5 or GU40E 1-5) contain two full monomeric units, connected by a Lys (blue) and a variable number of γ-aminobutyric acid (red) or γ-aminohexanoic acid (brown) linkers (refer to Table 2). The shorter dimers lack the γ-aminobutyric acid and γ-aminohexanoic acid linkers as well as one to three of the fixed residues at the C-terminus of each monomer unit (refer to Table 2). In these shorter dimers, two truncated monomer units were directly connected via Lys residue. Each compound was synthesized with a C-terminal Cys residue that was used to attach Fluorescein via maleimide chemistry. (FIG. 4B) Binding affinities (shown as dissociation constants; $K_D$) for the two series of homo-dimeric peptoids derived from monomers GU40C and GU40E. (FIG. 4C) Chemical structure of the best dimeric ligand identified; GU40C4. (FIG. 4D) Binding isotherm of fluoresceinated GU40C4 for immobilized VEGFR2 extracellular domain ($K_D \approx 30$ nM). Data points represent the mean of four measurements with error bars corresponding to the standard error of the mean.

(FIG. 5A) PAE/KDR cells; (FIG. 5B) PAE/KDR cells+100-fold excess of unlabeled GU40C4; (FIG. 5C) PAE/KDR cells; (FIG. 5D) PAE parental cells; (FIG. 5E) Hela cells; (FIG. 5F) HEK-293 cells; (FIG. 5G) MCF-7 cells; (FIG. 5H) Human foreskin fibroblast (HFF) cells.

(FIG. 6A) Effect of the indicated levels of GU40C4 and Avastin on autophosphorylation of VEGFR2 in PAE/KDR cells in the presence and absence of VEGF (1.3 nM) using antibodies for VEGFR2 and phosphorylated VEGFR2. (FIG. 6B) Quantification of the data shown in (FIG. 6A) reveal an $IC_{50}$ value of 0.9 µM. The data represent the average of four independent experiments with the error bars corresponding to the standard error of the mean. (FIG. 6C) Quantification of HUVEC proliferation in the absence and presence of 1.3 nM VEGF, competing with GU40C4. After four days, viable cells were determined using a luminescent assay. HUVEC were treated as follows (starting from left), without VEGF, VEGF only, VEGF+0.1 µM GU40C4, VEGF+1 µM GU40C4, VEGF+10 µM GU40C4, VEGF+10 µM FLAG peptide (control). GU40C4 was able to inhibit HUVEC proliferation halfway at 1 µM and almost to the basal level at 10 µM. FLAG peptide had no effect on HUVEC proliferation at 10 µM. Data points represent the mean of duplicate measurements with error bars corresponding to the standard error of the mean.

FIGS. 10A-B. (FIG. 10A) Structure of the control peptoid (Nmea-Nmea-Nser-Nmea-Nmea-Nser-Nmea-Nser-Nser).

(FIG. 10B) Sequence and structure of FLAG peptide used as the control ligand in HUVEC proliferation assay.

(FIG. 15A) Structure of GU40C(1) (FIG. 15B) Binding isotherms of GU40C, GU40(1) and a control peptoid that does not selective to bind to VEGFR2 ECD.

(FIG. 16A) Structures of GU40C(2) and GU40C(3). R: please see FIGS. 15A-B. (FIG. 16B) Binding isotherms of GU40C and its derivatives. Only GU40C and GU40C(2) able to display binding to VEGFR2 ECD.

(FIG. 17A) Downward arrows show GU40C truncation positions (FIG. 17B) Competitive binding assay results; increasing concentrations of unlabelled GU40C and truncated derivatives were competed with a constant amount of fluoraceinated GU40C. Symbols represent; GU40C (□), 8-mer (▲), 7-mer (▼), 6-mer (◇), 5-mer (○), 4-mer (■), control (x).

DESCRIPTION OF ILLUSTRATIVE EMBODIMENTS

Figure 1:
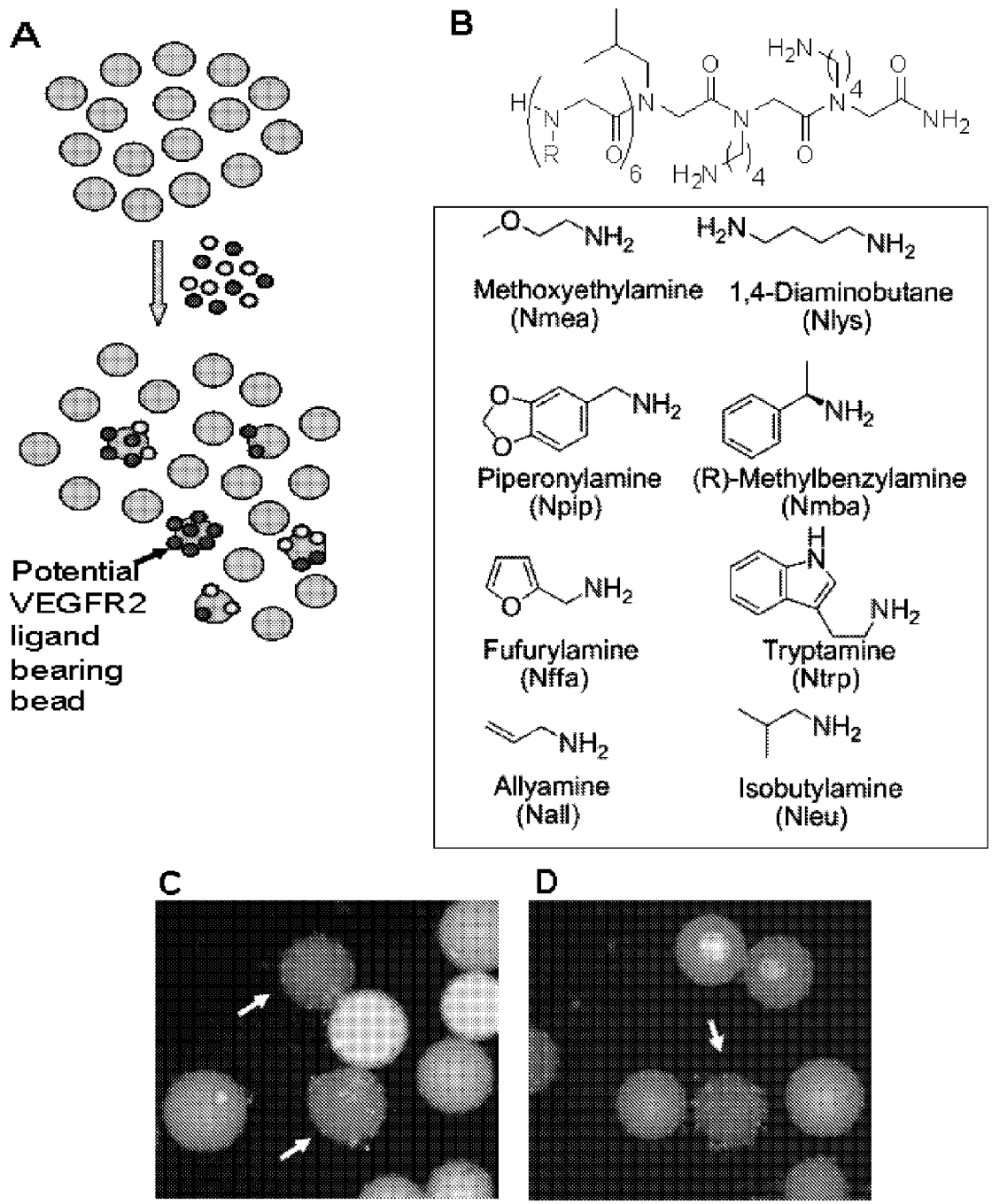
FIGS. 1A-D. A two-color, cell-based assay for the identification of peptoid ligands for VEGFR2.

The inventors and others have demonstrated that libraries of peptoids (oligo-N-substituted glycines) are rich sources of protein-binding ligands (Alluri et al., 2003; Zuckermann et al., 1994). Indeed, screens of combinatorial peptoid libraries result in the isolation of protein-binding peptoids that exhibit affinities and specificities quite similar to those exhibited by protein-binding peptides isolated from phage display libraries or other common means (Simon et al., 1992). However, peptoids are not sensitive to peptidases or proteases (Simon et al., 1992) and are even easier and more economical to synthesize than peptides (Zuckermann et al., 1992). Thus, peptoids would appear to be viable candidates for antagonists of receptor-hormone interactions. Based on the limitations of the antibody- and peptide-based approaches to antagonizing hormone-receptor interactions, the inventors decided to explore an alternative approach.

Using VEGFR2 as a model system, the inventors developed a novel cell-based binding screen that allows very large libraries of peptoids displayed on beads to be screened for receptor-binding compounds. This assay does not require elaborate automated instrumentation as is the case for functional screens of receptor activity. The inventors demonstrated that the peptoids isolated from such a screen bind VEGFR2 with dissociation constants in the low μM region, an affinity comparable to that of receptor-binding peptides, but much weaker than that exhibited by monoclonal antibodies (Witte et al., 1998). However, a simple dimerization strategy was employed to create low nM VEGFR2 lead compounds, an affinity that is comparable with that exhibited by an antibody. The inventors further showed that one of these dimeric peptoids is capable of acting as an antagonist of VEGF-VEGFR2 binding, and thus blocks hormone-dependent receptor activation and angiogenesis in vitro. This technology constitutes a general approach to the isolation of relatively low molecular mass, high affinity, serum-stable antagonists of receptor-hormone interactions. These, and other aspects of the invention, are described in great detail in the following pages.

1. Peptoids and Peptoid Array

The inventors synthesized a library of peptoids with a theoretical diversity of approximately 250,000 compounds on TentaGel beads. The design of the library (FIG. 1B) attempted to take some advantage of the structure of the VEGF-VEGR2 complex. The receptor consists of seven extracellular immunoglobulin-like domains, a single transmembrane region, and an intracellular tyrosine kinase domain (Matthews et al., 1991; Terman et al., 1991). VEGF binds to extracellular domains 2 and 3 (Fuh et al., 1998) of VEGFR2. It has been reported that Isoleucine (Ile-43, 46, 83), Glutamate (Glu-64), Phenylalanine (Phe-17), Glutamine (Gln-79), Lysine (Lys-84) and Proline (Pro-85) side chains of VEGF are the most important moieties for the binding to VEGFR2 (Muller et al., 1997). Therefore, in designing this peptoid library, the inventors decided to have at least two of the above residues fixed with the intent of biasing the library for VEGFR2 binding. The inventors selected Lys-like and Leu-like residues to be fixed at the C-terminus of each molecule in the library. Leu was chosen instead of Ile because Ile was not validated for peptoid synthesis at the time of synthesis, and Leu was the most suitable substitute. Also, the inventors decided to place one additional Lys-like residue in between the resin and the 8-mer peptoid, making the full-length of each peptoid a total of nine residues. The positively-charged Lys-like residue can repel the peptoids from each other on the bead surface and would avoid aggregation of the peptoids that could hinder proper display. The library was synthesized on TentaGel macrobeads (140-170 μM diameter), which have excellent stability and swelling properties and also provide a non-sticky surface that is ideal for reducing non-specific binding in screening experiments (Alluri et al., 2003). Synthesis of the library was conducted using eight different amines (FIG. 1B) resulting in a theoretical diversity of 262,144 compounds.

A. Peptoid Array Synthesis 9-mer peptoid library was synthesized on TentaGel macrobeads (140-170 μm; substitution: 0.48 mmol/g resin; Rapp Polymere) using microwave (1000 W) assisted synthesis protocol. TentaGel macrobeads were distributed equally into eight peptide synthesis reaction vessels, swelled in dimethylformamide (DMF) and each reaction vessel was treated with 2M Bromoacetic acid and 3.2M Di-isopropylcarbodiimide (DIC) the coupling was performed in microwave oven set to deliver 10% power (2×15 sec). After washing the beads with DMF, each vessel was treated with one of the eight primary amines at 2M concentration and again the coupling was performed in microwave as described above. Beads were washed, pooled, randomized and were redistributed equally into eight peptide synthesis vessels, and the procedure was repeated until the desired length is achieved. For first three fixed residues (Nleu-Nlys-Nlys), each step was followed as above except the pooling step. At the completion of the library synthesis, beads were treated with 95% TFA, 2.5% tri-isopropylsilane and 2.5% water for 2 h to remove side chain protection groups and were neutralized with 10% di-isopropylethylamine in DMF. Finally, washed with dichloromethane, dried and stored at 4° C. (Alluri et al., 2003).

B. Synthesis of GU40C, GU40C4, GU81 and GU81 Dimer

In both monomeric (GU40C) and dimeric (GU40C4) forms, resynthesis of peptoid ligands were conducted on Knorr Amide MBHA resin. After loading Cys residue, general microwave assisted protocol was used to build the peptoid portion and finally Fluorescein-5-maleimide and Maleimide PEO2-Biotin (Pierce) were coupled.

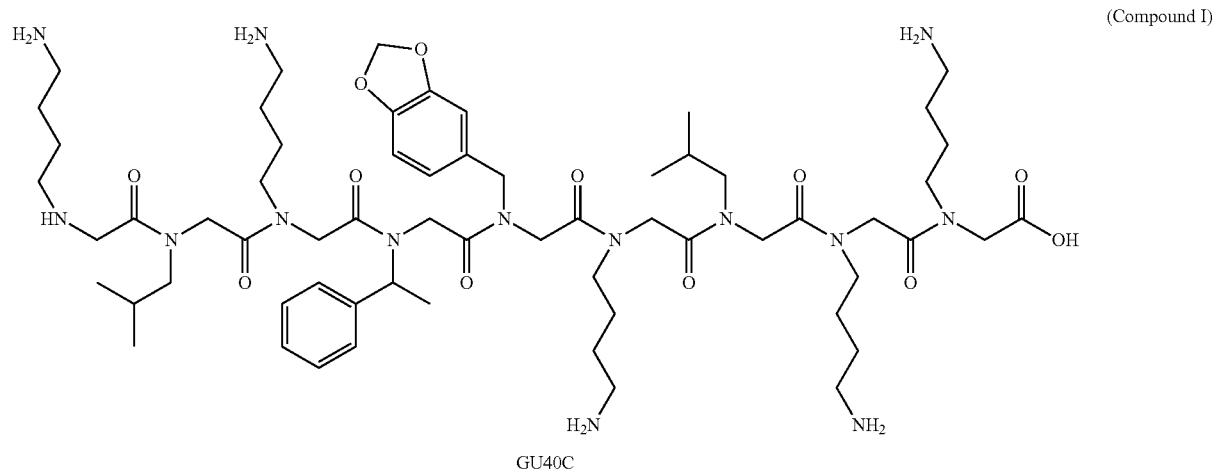

(Compound I)

GU40C

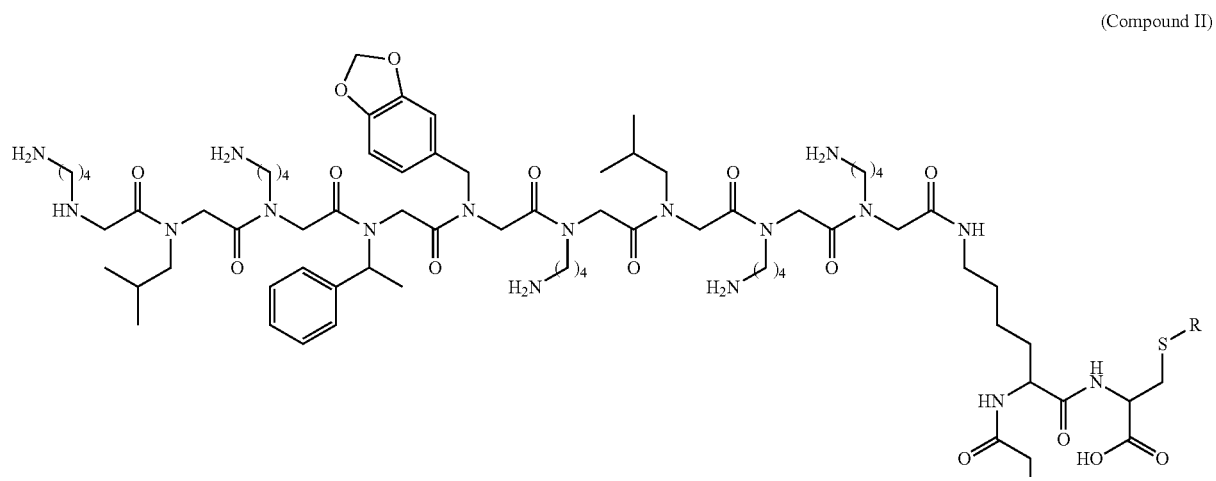

(Compound II)

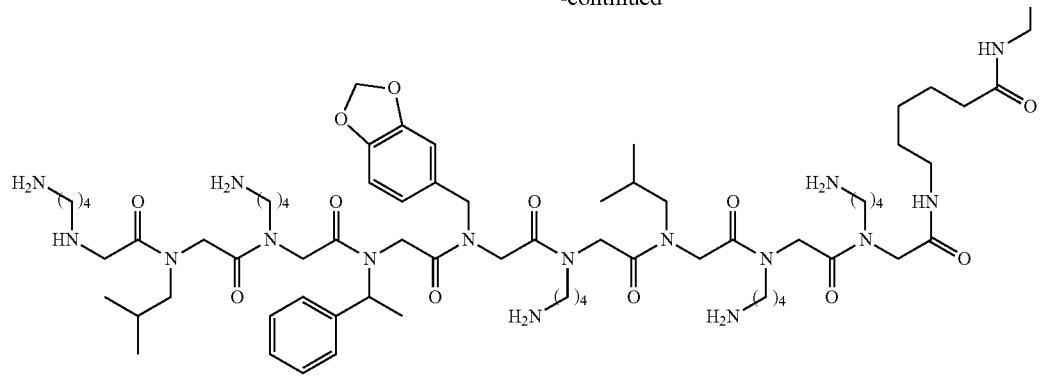

GU40C4

C. Linkers

The present invention may comprise multimeric species—dimers, trimers or other multimers of monomeric peptoids—that can be synthesized by solid-phase methods, for example by first attaching a lysine or other diamine-containing compound to the bead, followed by growing the peptoid chains from each amino group, or created first and then joined via a linker. Any of a wide variety of linkers may be utilized to effect the joinder of peptoids. Certain linkers will generally be preferred over other linkers, based on differing pharmacologic characteristics and capabilities. In particular, the linkers will be attached at the free —OH group of GU40C, and may be represented by an R group substituted for that —OH group, i.e., —C(=O)—R—C(=O)—.

Cross-linking reagents are used to form molecular bridges that tie together functional groups of two molecules. Linking/coupling agents used to combine to peptoids of the present invention include linkages such as avidin-biotin, amides, esters, thioesters, ethers, thioethers, phosphoesters, phosphoramides, anhydrides, disulfides, and ionic and hydrophobic interactions.

TABLE 1

HETERO-BIFUNCTIONAL CROSS-LINKERS

| Linker | Reactive Toward | Advantages and Applications | Spacer Arm Length |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |

TABLE 1-continued

HETERO-BIFUNCTIONAL CROSS-LINKERS

| Linker | Reactive Toward | Advantages and Applications | Spacer Arm Length |
|---|---|---|---|
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is particular that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1988). The use of such cross-linkers is well understood in the art. Another embodiment involves the use of flexible linkers.

Peptide linkers that include a cleavage site for an enzyme preferentially located or active within a tumor environment also are contemplated. Exemplary forms of such peptide linkers are those that are cleaved by urokinase, plasmin, thrombin, Factor Ixa, Factor Xa, or a metallaproteinase, such as collagenase, gelatinase, or stromelysin.

D. Variants or Analogs of GU40C and GU40C4

Generic Formula. As discussed below in the Examples, hundreds of derivatives of the parent GU40C peptoid were made in which modest alterations in the three critical side chains were introduced in an effort to improve the "fit" of this region of the peptoid with the receptor. One of these was the GU81 peptoid, described above, which gave a 4-fold better binding to the receptor than did the parent GU40C molecule. Also as discussed below, the dimer of GU81 is active in an in vivo assay in combination with doxorubicin against in particularly aggressive mouse cancer model. The formula below shows variant and invariant locations by position number:

GENERIC PHARMACORE

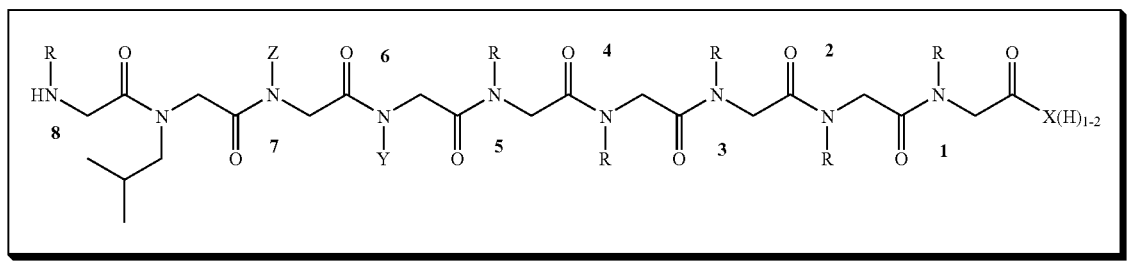

X = O, N

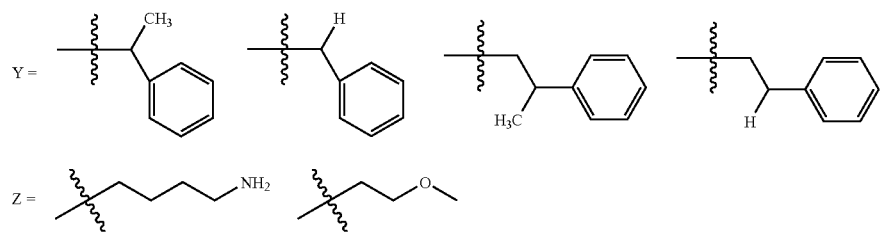

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single-chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

In addition to constraints on the side chains, as indicated above, the carbonyl groups shown in the yellow boxes have also been found to be important for binding.

Substitutional Variants. It also is contemplated in the present invention that variants or analogs of GU40C and GU40C4 peptoids may also inhibit VEGF signaling through VEGFR2. Sequence variants of GU40C and GU40C4, primarily making conservative substitutions, may provide improved compositions. Substitutional variants typically contain the exchange of one amino acid or amino acid analog for another at one or more sites within the molecule, and may be designed to modulate one or more properties of the molecule, in particular the affinity of the molecule for the target, without the loss of other functions or properties.

Altered Amino Acids. As shown above, peptoids may employ modified, non-natural and/or unusual amino acids. A table of exemplary, but not limiting, modified, non-natural and/or unusual amino acids is provided herein below. Chemical synthesis may be employed to incorporate such amino acids into the peptides of interest.

TABLE 2

Modified, Non-Natural and Unusual Amino Acids

| Abbr. | Amino Acid |
|---|---|
| Aad | 2-Aminoadipic acid |
| Baad | 3-Aminoadipic acid |
| Bala | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| Ahyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Mimetics. In addition to the variants discussed above, the present inventors also contemplate that structurally similar compounds may be formulated to mimic the key portions of peptoids of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and high permissive for mutation. This motif is composed of a β sheet and an α-helix bridged in the interior core by three disulfides.

β-II turns have been mimicked successfully using cyclic L-pentapeptides and those with D-amino acids (Weisshoff et al., 1999). Also, Johannesson et al. (1999) report on bicyclic tripeptides with reverse turn inducing properties.

Methods for generating specific structures have been disclosed in the art. For example, α-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

E. Purification of Peptoids

It may be desirable to purify peptoids according to the present invention. Purification techniques are well known to those of skill in the art. These techniques typically involve chromatographic and electrophoretic techniques to achieve partial or complete purification (or purification to homogeneity). Analytical methods particularly suited to the preparation of a pure peptoid are ion-exchange chromatography, exclusion chromatography; polyacrylamide gel electrophoresis; isoelectric focusing. A particularly efficient method of purifying peptoids is fast protein liquid chromatography or even HPLC.

Certain aspects of the present invention concern the purification, and in particular embodiments, the substantial purification, of a peptoid. The term "purified peptoid" as used herein, is intended to refer to a composition, isolatable from other components, wherein the peptoid is purified to any degree relative to its normally-obtainable state. A purified peptoid therefore also refers to a peptoid free from the environment in which it may normally occur.

Generally, "purified" will refer to a peptoid composition that has been subjected to fractionation to remove various other components, and which composition substantially retains its expressed biological activity. Where the term "substantially purified" is used, this designation will refer to a composition in which the peptoid forms the major component of the composition, such as constituting about 50%, about 60%, about 70%, about 80%, about 90%, about 95% or more of the composition by weight.

Various methods for quantifying the degree of purification of the peptoid will be known to those of skill in the art in light of the present disclosure. These include, for example, determining the specific activity of an active fraction, or assessing the amount of peptoid within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the peptoid exhibits a detectable activity.

Various techniques suitable for use in peptoid purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified peptoid.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

2. VEGF

A. VEGF

Vascular endothelial growth factor (VEGF) is an important signaling protein involved in both vasculogenesis (the de novo formation of the embryonic circulatory system) and angiogenesis (the growth of blood vessels from pre-existing vasculature). As its name implies, VEGF activity has been mostly studied on cells of the vascular endothelium, although it does have effects on a number of other cell types (e.g., stimulation monocyte/macrophage migration, neurons, cancer cells, kidney epithelial cells). In vitro, VEGF has been shown to stimulate endothelial cell mitogenesis and cell migration. VEGF is also a vasodilator and increases microvascular permeability and was originally referred to as vascular permeability factor.

The broad term "VEGF" covers a number of proteins from two families, that result from alternate splicing of mRNA from a single, 8 exon, VEGF gene. The two different families are referred to according to their terminal exon (exon 8) splice site—the proximal splice site (denoted $VEGF_{xx}$) or distal splice site ($VEGF_{xxb}$). In addition, alternate splicing of exon 6 and 7 alters their heparin binding affinity, and amino acid number (in humans: $VEGF_{121}$, $VEGF_{121}b$, $VEGF_{145}$, $VEGF_{165}$, $VEGF_{165}b$, $VEGF_{189}$, $VEGF_{206}$; the rodent orthologs of these proteins contain one fewer amino acid). These domains have important functional consequences for the VEGF splice variants as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate proteoglycans (HSPGs) and neuropilin co-receptors on the cell surface, enhancing their ability to bind and activate the VEGF signaling receptors (VEGFR's).

The VEGF splice variants are released from cells as glycosylated disulfide-bonded dimers. Structurally VEGF belongs to the PDGF family of cystine-knot growth factors. Subsequently, several closely-related proteins were discovered (Placenta growth factor (PlGF), VEGF-B, VEGF-C and VEGF-D) which together comprise the VEGF sub-family of growth factors. VEGF is sometimes referred to as VEGF-A to differentiate it from these related growth factors. A number of VEGF-related proteins have also been discovered encoded by viruses (VEGF-E) and in the venom of some snakes (VEGF-F).

B. VEGFR

All members of the VEGF family stimulate cellular responses by binding to tyrosine kinase receptors (the VEGFRs) on the cell surface, causing them to dimerize and become activated through transphosphorylation, although to different sites, times and extents. The VEGF receptors have an extracellular portion consisting of 7 immunoglobulin-like domains, a single transmembrane spanning region and an intracellular portion containing a split tyrosine-kinase domain. VEGF-A binds to VEGFR-1 (Flt-1) and VEGFR-2 (KDR/Flk-1). VEGFR-2 appears to mediate almost all of the known cellular responses to VEGF. The function of VEGFR-1 is less well defined, although it is thought to modulate VEGFR-2 signaling. Another function of VEGFR-1 may be to act as a dummy/decoy receptor, sequestering VEGF from VEGFR-2 binding (this appears to be particularly important during vasculogenesis in the embryo). VEGF-C and VEGF-D, but not VEGF-A, are ligands for a third receptor (VEGFR-3), which mediates lymphangiogenesis.

C. Known Antagonists of VEGFR

Anti-VEGF therapies are important advances in the treatment of certain cancers. They can be monoclonals such as Bevacizumab (Avastin®), or oral small molecules that inhibit the tyrosine kinases stimulated by VEGF, such as Sunitinib, Sorafenib, Axitinib, Pazopanib.

3. Screening Assays

A. Peptoid Variants

The present invention also contemplates the screening of peptoid variants of GU40C4 for their ability to bind to VEGFR2 and to inhibit angiogenesis. In addition to performing the binding assay described in the Examples, by which GU40C4 was identified, various other assays may also be conducted, such as in vitro and in vivo binding and inhibition assays, as well as assays for particular therapeutic efficacy, e.g., anti-cancer, anti-macular degeneration and anti-angiogenesis.

The present invention provides methods of screening for agents that bind VEGFR2. In an embodiment, the present invention is directed to a method of:

(a) providing a candidate peptoid;
(b) contacting the peptoid with VEGFR2; and
I determining the binding of the candidate peptoid with VEGFR2, wherein binding to VEFGR2 identifies the candidate as a putative inhibitor of angiogenesis.

Measuring binding to may be direct, by identifying a VEGFR2-candidate complex, by identifying labeled candidate associated with VEGFR2, or by assessing the inhibition of binding of a labeled peptoid to VEGFR2.

It will, of course, be understood that all the screening methods of the present invention are useful in themselves notwithstanding the fact that effective candidates may not be found. The invention provides methods for screening for such candidates, not solely methods of finding them.

Various cells that express VEGFR2 can be utilized for screening of candidate substances. Exemplary cells include, but are not limited to porcine aortic endothelial cells and human vascular endothelial cells (HUVECs). Depending on the assay, culture may be required. Labeled candidate peptoids may be contacted with the cell and binding assessed therein. Various readouts for binding of candidate substances to cells may be utilized, including ELISA, fluorescent microscopy and FACS. In particular, the assay shown in FIG. 1A may be utilized in various formats to identify peptoids of interest.

The present invention particularly contemplates the use of various animal models. For example, various animal models of cancer may be used to determine if the candidate peptoids inhibits cancer cell growth, metastasis or recurrence, or affects its ability to evade the effects of other drugs. Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by oral, sublingual, intratracheal instillation, bronchial instillation, intradermal, subcutaneous, intramuscular, intraperitoneal or intravenous injection. Specifically contemplated are intratumoral and intraocular administration and regional (to a tumor or eye) administration.

B. Cell Based Screening Formats

Another aspect of the invention involves cell based screening assays that identify target-specific ligands, such as peptoids. Cells having differential characteristics, such as the presence or absence of a cell surface receptor, but otherwise identical, are differentially labeled (e.g., two different colored quantum dots). The cells are then mixed in an approximately 1:1 ratio and then exposed to a library of molecules displayed on hydrophilic beads. After appropriate incubation and washing, the beads that bind only one color cell are picked. The beads are treated to remove the cells and other debris, and the bound molecule is identified by an appropriate analytical technique. This two-color assay demands extremely high specificity. If the bead-displayed molecule binds any other molecule on the cell surface other than the target receptor, then both colored cells will be retained and the molecule will not be identified as a hit. See Udugamasooriya et al. (2008).

The assay can be modified to accommodate a variety of different formats. For example, a three cell types assay can be used to distinguish ligands that bind to highly related molecules. For example, where two receptors are almost identical, cells are provided that are null or have one or the other related receptor. Each cell type (null, receptor 1-containing and receptor 2-containing) is labeled with a different agent (e.g., colored quantum dot). The cells are mixed together in an approximately 1:1:1 ratio and exposed to a bead library. Beads that bind only one color cell are picked and the chemical that they display is characterized (see FIG. 24).

Examples of structures that can be differentiated include antibody or T-cell receptors of various immune cells, growth factor receptors, cell matrix proteins, lectins, carbohydrates, lipids, cell surface antigens from various pathogens. Additionally, the cells could differ not in the composition of the cell surface molecules, but in their arrangement. For example on one cell type, two given cell surface molecules might associate with one another and provide a unique binding site for a ligand that might be absent from a different cell type where these receptors do not associate. Labeling can utilize calorimetric, fluorimetric, bioluminescent or chemiluminescent labels.

The assay can also be modified to identify ligands that bind to cells present in only one of two or more distinct cell populations. For example, all CD4+ T cells from a healthy individual or group of individuals could be labeled with one colored dye and the CD4+ T cells from an individual or group of individuals with an autoimmune disease could be labeled with a different colored dye. The two populations of T cells could then be mixed with the bead library and beads retaining only cells from the autoimmune patients could be selected. These T cells would be candidates for the autoimmune T cells that display the T cell Receptor (TCR) that binds the autoantigen and contributes to disease, since these cells should only be abundant in the autoimmune samples and not in cells obtained from healthy individuals.

In another application, the two or more cell populations could differ solely in the presence or absence of a genetic mutation that might result in a change in the composition and/or organization of molecules on the cell surface. An example would be cells that contain wild-type or mutant ras gene (e.g., K-ras).

4. Treating Cancers

In one aspect of the present invention, one may utilize the peptoid compounds of the present invention and analogs thereof in the inhibition of cancer. Any of a variety of different cancers, particularly solid tumors, are contemplated as suitable for treatment with the present invention. For example, a glioma cell, a sarcoma cell, a myeloma cell may be treated with peptoids, as can cancer cells such as a lung cancer cell, a skin cancer cell, a head & neck cancer cell, a stomach cancer cell, a breast cancer cell, a colon cancer cell, a pancreatic cancer cell, a liver cancer, an ovarian cancer cell, a uterine cancer cell, a cervical cancer cell, a testicular cancer cell, a rectal cancer cell, an esophageal cancer cell, or a brain cancer cell. The cancer may also be primary, metastatic, multi-drug resistant or recurrent.

A. Monotherapy

In one embodiment, the subject will be administered peptoid or variants, mimetics or analogs thereof. Formulations would be selected based on the route of administration and purpose including, but not limited to, parenteral formulations, topical formulations, liposomal formulations and classic pharmaceutical preparations for oral administration. Particular routes include intratumoral injection and injection into the tumor cell vasculature. Repeated or continuous therapy over a period of time (weeks to months) also is contemplated.

B. Combined Therapy

In order to increase the effectiveness of peptoid therapy, it may be desirable to combine these compositions with another agent effective in the treatment of cancer. The terms "contacted" and "exposed," when applied to a cell, tissue or organism, are used herein to describe the process by which an peptoid therapy and/or other agent are delivered to a target cell, tissue or organism or are placed in direct juxtaposition with the target cell, tissue or organism.

The peptoid treatment may precede, be concurrent with and/or follow the other agent(s) by intervals ranging from minutes to weeks. In embodiments where the peptoid treatment and other agent(s) are applied separately to a cell, tissue or organism, one would generally ensure that a significant period of time did not expire between the time of each delivery, such that the peptide and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the peptoid or mimic or analog. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 18 hours, about 24 hours, about 36 hours, about 48 hours, about 3 days, about 4 days, about 5 days, about 6 days, about 7 days, about 8 days, about 9 days, about 10 days, about 11 days, about 12 days, about 13 days, about 14 days, about 21 days, about 4 weeks, about 5 weeks, about 6 weeks, about 7 week or about 8 weeks or more, and any range derivable therein, prior to and/or after administering peptoid or mimic or analog thereof.

For example, as shown in FIG. 26, treatment of a mouse bearing a tumor with the GU81 dimer and the classical anti-cancer compound doxorubicin is more effective in slowing tumor growth than either compound alone.

Various combination regimens of the peptoid treatment and one or more other anti-pain agents may be employed. Non-limiting examples of such combinations are shown below, wherein a peptoid composition is "A" and the other anti-cancer agent is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Other combinations are contemplated. Again, to achieve cancer cell inhibition, both agents are delivered to a cell in a combined amount effective to achieve the desired inhibition, which may include cell stasis or cell death.

Administration of the peptoid composition to a cell, tissue or organism may follow general protocols for the administration of pharmaceuticals, taking into account the toxicity, if any. It is expected that the treatment cycles would be repeated as necessary. In particular embodiments, it is contemplated that various additional agents may be applied in any combination with the present invention.

Agents or factors suitable for use in a combined therapy are any chemical compound or treatment method that may also produce an advantageous effect, alone or in combination with GU40C4. Such agents and factors include radiation and waves that induce DNA damage such as, $\gamma$-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., doxorubicin, verapamil, podophyllotoxin, adriamycin, 5-fluorouracil (5FU), etoposide (VP-16), camptothecin, actinomycin-D, mitomycin C, cisplatin (CDDP) and even hydrogen peroxide.

C. Pharmaceutical Formulations

Pharmaceutical formulations of the present invention comprise an effective amount of a peptoid dissolved or dispersed in a pharmaceutically acceptable carrier. The phrases "pharmaceutical or pharmacologically acceptable" refer to compositions that do not produce an adverse, allergic or other untoward reaction when administered to an animal, such as, for example, a human, as appropriate. The preparation of such pharmaceutical compositions are known to those of skill in the art in light of the present disclosure, as exemplified by Remington's Pharmaceutical Sciences, $18^{th}$ Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

The pharmaceuticals of the present invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The pharmaceuticals may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi.

It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

5. Treatment of Macular Degeneration

A. Background

Macular degeneration is a medical condition predominantly found in elderly adults in which the center of the inner lining of the eye, known as the macula area of the retina, suffers thinning, atrophy, and in some cases bleeding. This can result in loss of central vision, which entails inability to see fine details, to read, or to recognize faces. According to the American Academy of Opthalmology, it is the leading cause of central vision loss (blindness) and in the United States today for those over the age of fifty years. Although some macular dystrophies that affect younger individuals are sometimes referred to as macular degeneration, the term generally refers to age-related macular degeneration (AMD or ARMD).

Age-related macular degeneration begins with characteristic yellow deposits in the macula (central area of the retina) called drusen. Most people with these early changes have good vision. People with drusen can go on to develop advanced AMD. The risk is considerably higher when the drusen are large and numerous and associated with disturbance in the pigmented cell layer under the macula. Recent research suggests that large and soft drusen are related to elevated cholesterol deposits and may respond to cholesterol lowering agents or the Rheo Procedure.

Advanced AMD, which is responsible for profound vision loss, has two forms: dry and wet. Central geographic atrophy, the dry form of advanced AMD, results from atrophy to the retinal pigment epithelial layer below the retina, which causes vision loss through loss of photoreceptors (rods and cones) in the central part of the eye. While no treatment is available for this condition, vitamin supplements with high doses of antioxidants, Lutein and Zeaxanthin, have been demonstrated by the National Eye Institute and others to slow the progression of dry macular degeneration and in some patients, improve visual acuity.

Neovascular or exudative AMD, the wet form of advanced AMD, causes vision loss due to abnormal blood vessel growth in the choriocapillaries, through Bruch's membrane, ultimately leading to blood and protein leakage below the macula. Bleeding, leaking, and scarring from these blood vessels eventually cause irreversible damage to the photoreceptors and rapid vision loss if left untreated.

Fluorescein angiography allows for the identification and localization of abnormal vascular processes. Optical coherence tomography is now used by most ophthalmologists in the diagnosis and the followup evaluation of the response to treatment by using either Avastin or Lucentis which are injected into the vitreous of the eye at various intervals.

Until recently, no effective treatments were known for wet macular degeneration. However, anti-VEGF (anti-Vascular Endothelial Growth Factor) agents, when injected directly into the vitreous humor of the eye using a small, painless needle, can cause contraction of the abnormal blood vessels and improvement of vision. The injections frequently have to be repeated on a monthly or bi-monthly basis. Examples of these agents include Lucentis, Avastin and Macugen. Only Lucentis and Macugen are FDA approved as of April 2007, and only Lucentis and Avastin appear to be able to improve vision, but the improvements are slight and do not restore full vision. It is anticipated by GU40C4 would be used similar to how Avastin is administered.

The Age-Related Eye Disease Study showed that a combination of high-dose beta-carotene, vitamin C, vitamin E, and zinc can reduce the risk of developing advanced AMD by about 25% in those patients who have earlier but significant forms of the disease. This is the only proven intervention to decrease the risk of advanced AMD at this time. A follow up study, Age-Related Eye Disease Study 2 to study the potential benefits of lutein, zeaxanthine, and fish oil, is currently underway.

Anecortave acetate, (Retanne), is an anti-angiogenic drug that is given as an injection behind the eye (avoiding an injection directly into the eye) that is currently being studied as a potential way of reducing the risk of neovascular (or wet) AMD in high-risk patients. Recent studies suggest that statins, a family of drugs used for reducing cholesterol levels, may be effective in prevention of AMD, and in slowing its progression.

B. Treatment

In accordance with the present invention, peptoids will be utilized much in the same way as Avastin. It is contemplated that in addition to injection, peptoids of the present invention, because of their smaller size, may be administered in a topical solution, i.e., eye drops. Treatment can be prophylatic, prior to the development of symptoms, or may be therapeutic in that a diagnosis and/or symptoms of AMD are present. Administration may be chronic, i.e., on a daily or weekly basis.

Opthalmic formulation delivers the drug on the eye, into the eye, or onto the conjunctiva. Transcorneal transport (i.e., drug penetration into the eye) is not an effective process, with an estimated only one-tenth of a dose penetrating into the eye. Most ophthalmic solutions are dispensed in eye dropper bottles. Patients should be shown how to properly instill the drops in their eyes, and every effort should be made to emphasize the need for instilling only one drop per administration, not two or three. When more than one drop is to be administered, wait at least five minutes between administrations.

The physiologic pH of blood and tears is approximately 7.4. Thus, from a comfort and safety standpoint, this would be the optimal pH of ophthalmic and parenteral solutions. This may not be possible, however, from a perspective of solubility, chemical stability or therapeutic activity. Thus, some compromise must be made and product stability must be considered paramount. When a formulation is administered to the eye, it stimulates the flow of tears. Tear fluid is capable of quickly diluting and buffering small volumes of added substances, thus the eye can tolerate a fairly wide pH range. Ophthalmic solutions may range from pH 4.5-11.5, but the range to prevent corneal damage is 6.5-8.5.

Isotonic or iso-osmotic solutions do not damage tissue or produce pain when administered are desired. Solutions which contain fewer particles and exert a lower osmotic pressure than 0.9% saline are called hypotonic and those exerting higher osmotic pressures are referred to as hypertonic. Administration of a hypotonic solution produces painful swelling of tissues as water passes from the administration site into the tissues or blood cells. Hypertonic solutions produce shrinking of tissues as water is pulled from the biological cells in an attempt to dilute the hypertonic solution. The eye can tolerate a range of tonicities as low as 0.6% and as high as 1.8% sodium chloride solution. Several methods are used to adjust isotonicity of pharmaceutical solutions.

Preservatives are commonly used in ophthalmic formulations. The FDA Advisory Review Panel on OTC Ophthalmic Drug Products (December 1979) has established concentrations for formulations that will have direct contact with the eye.

Some drugs can be chemically degraded by oxidation, and an antioxidant should be added to such formulations. The common agents and their maximum concentration used in ophthalmic formulations include sulfites (can cause allergic-type reactions in certain people) and disodium ethylenediaminetetraacetic acid.

Viscosity measures the resistance of a solution to flow when a stress is applied. Generally the solutions are 1% or 2% and the viscosity is measured at 20° C. Viscosity enhancers are used in ophthalmic solutions to increase their viscosity. This enables the formulation to remain in the eye longer and gives more time for the drug to exert its therapeutic activity or undergo absorption. The most common viscosity desired in an ophthalmic solution is between 25 and 50 cps.

Sterility is defined as the absence of viable microbial contamination, and is an absolute requirement of all ophthalmic formulations. Therefore, ophthalmic formulations must be prepared in a laminar flow hood using aseptic techniques just the same as intravenous formulations. The sterile formulations must be packaged in sterile containers.

For additional resources, see Hecht, G. *Ophthalmic Preparations*, Chapter 89, pp. 1563-1573; Niebergall, P. J. *Ionic Solutions and Electrolytic Equilibria*, Chapter 17, pp. 225-227; Sokoloski, T. D. *Solutions and Phase Equilibria*, Chapter 16, pp. 206-208 and Reich, I., Schnaare, R., Sugita, E. T. *Tonicity, Osmoticity, Osmolality and Osmolarity*, Chapter 36, pp. 613-616, 620-627 all in *Remington's*, $19^{th}$ ed.

6. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A. Materials and Methods

Peptoid library synthesis. 9-mer peptoid library was synthesized on TentaGel macrobeads (140-170 μm; substitution: 0.48 mM/g resin; Rapp Polymere) using microwave (1000 W) assisted synthesis protocol. TentaGel macrobeads were distributed equally into eight peptide synthesis reaction vessels, swelled in dimethylformamide (DMF) and each reaction vessel was treated with 2M Bromoacetic acid and 3.2M Di-isopropylcarbodiimide (DIC) and the coupling was performed in microwave oven set to deliver 10% power (2×15 seconds). After washing the beads with DMF, each vessel was treated with one of the eight primary amines at 2M concentration and again the coupling was performed in microwave as described above. Beads were washed, pooled, randomized and were redistributed equally into eight peptide synthesis vessels, and the procedure was repeated until the desired length is achieved. For first three fixed residues (Nleu-Nlys-Nlys), each step was followed as above except the pooling step. At the completion of the library synthesis, beads were treated with 95% TFA, 2.5% tri-isopropylsilane and 2.5% water for 2 h to remove side chain protection groups and were neutralized with 10% di-isopropylethylamine in DMF. Finally, washed with dichloromethane, dried and stored at 4° C. (Alluri et al., 2003).

Bi-color on-bead cells screening assay. About 100,000 library beads were swelled in DMF, washed with PBS and finally equilibrated in 3% BSA containing DMEM media for 1 h. PAE/KDR and PAE parental cells (Sibtech, Inc.) were removed from culture plates using enzyme free cell dissociation buffer (Gibco), washed and re-suspended in DMEM media. Cells were labeled using quantum dots (Invitrogen) following the manufactures protocol. PAE/KDR cells labeled with Qtracker 655 (red) and PAE parental cells labeled with Qtracker 565 (green). Both labeled cells were mixed with 1:1 ratio to give final cell density $1 \times 10^6$ per cell type, and gently stirred to break cell clusters. Cell suspension mixture was added to the beads containing culture plates and incubated at 37° C. with gentle shaking for 60-75 min. Beads were gently washed two times with DMEM media and visualized under the fluorescent microscope equipped with the DAPI filter (10× magnification). Single positive beads containing fluorescently tagged red cells only were manually removed with a 20 μl pipette using medium size pipette tips. Selected beads were washed and boiled with 1% SDS solution for 30 min to strip off cells and subjected to Edman sequencing in order to identify the sequence.

Dimeric library synthesis. The dimer libraries were synthesized on Knorr Amide MBHA resin (substitution: 0.78 mmol/g resin; Novabiochem). First Fmoc-Cys(Trt)-OH was loaded onto the bead (HOBt, HBTU, DIPEA) followed by Fmoc-Lys(Dde)-OH(HOBt, DIC). Then Fmoc group was selectively removed and coupled different numbers and combinations of Fmoc-B-Ala-OH or/and Fmoc-Y-Ahx-OH (HOBt, DIC) onto the N-terminal amino group of Lys in longer dimer series. Then, both Fmoc and Dde groups were removed (2% hydrazine and 20% piperidine) and continued general microwave assisted peptoid synthesis steps as described in the library synthesis procedure until the total nine residues were added. Here in each treatment, the residues were added to both open amino ends ultimately connected by Lys (double addition). In shorter dimers, after coupling with initial Cys, Fmoc-Lys(Fmoc)-OH was coupled. Once both Fmoc groups were removed simultaneously, started coupling peptoid residues again using the microwave assisted protocol, which resulted in double addition as above. For truncated peptoid dimers, avoided adding C-terminal residues one at a time up to first 3 residues, which ultimately resulted shorter dimers with 6-8 residues in each monomer. After the synthesis, peptoid dimers were cleaved off the resin using 95% TFA, 2.5% tri-isopropylsilane and 2.5% water for 2 h and purified using HPLC. Each compound was treated with fluorescein-5-maleimide (pH=7; Pierce) in PBS to attach FITC group and were re-purified using HPLC.

Resynthesis of biotinylated and FITC labeled peptoids. In both monomeric and dimeric forms, resynthesis of peptoid ligands were conducted on Knorr Amide MBHA resin. After loading Cys residue, general microwave assisted protocol was used to build the peptoid portion and finally Fluorescein-5-maleimide and Maleimide PEO2-Biotin (Pierce) were coupled.

ELISA based binding assay. White, clear bottom 96-well plates (Corning Inc.) were coated with of 1 μg/ml recombinant human VEGFR2 protein (R&D Systems) using the sensitizing buffer (0.621 g $NaHCO_3$ & 0.275 g $Na_2CO_3$ dissolved on 100 ml of ddH$_2$O, pH=9.5) overnight at 4° C. Washed with 3×200 μl of wash buffer 1×PBS with 0.05% Tween-20 and blocked with Startingblock blocking buffer (Pierce). Added 50 μl of serial dilutions of FITC labeled peptoids dissolved in Startingblock blocking buffer to each well & allowed to react for 1 h at room temperature. Washed with 5×200 μl of wash buffer 1×PBS with 0.05% Tween-20 and remaining fluorescence was measured at 520 nm using the plate reader.

GU40C4 cell surface binding assay. Different types of cells (PAE/KDR, PAE, Hela, HEK-293, MCF-7, HFF) were grown on each well of chamber slides (Nalge Nunc International) (10,000 cells/chamber) overnight. Washed, and fixed cells with 3.7% formaldehyde and blocked with Startingblock blocking buffer. Each chamber was treated (except the control) with 75 nm biotinylated GU40C4 peptoid followed by Qdot® 655 streptavidin conjugate (Invitrogen). After the final washing, cells were mounted by ProLong® Gold antifade reagent with DAPI (Invitrogen) and visualized under DAPI filter of the fluorescence microscope.

Western blots. Experiments were conducted using PAE/KDR cells that were grown on 6-well plates. Overnight serum starved cells were treated with 1.3 nM VEGF (Invitrogen) and different concentrations of GU40C4 peptoid or Avastin (Genentech). The blots were probed with Phospho-VEGF receptor 2 (Tyr1175) (19A10) rabbit monoclonal or Total VEGFR2 primary antibodies (Cell signaling) and HRP-conjugated secondary antibody (BioRad).

HUVEC proliferation assay. HUVEC cells (ScienceCell) were harvested using enzyme free cell dissociation buffer and resuspended in ECM (5% FBS). Cells were plated (2000 cells/well) on white, clear bottom 96-well plates coated with gelatin. Cells were grown for 24 h at 37° C. Change the media which has 0.2% FBS, and treated with 1.3 nM VEGF and different concentrations of GU40C4 peptoid and FLAG peptide as the control. The treatment was repeated with fresh media (0.2% FBS) and reagents after two days. After four days, viable cells were determined using CellTiter-Glo® Luminescent Cell Viability Assay kit (Promega), and the luminescent signal was read by the plate reader.

HUVEC tube formation assay. Endothelial cell medium gel (ECM gel) was thawed overnight at 4° C. refrigerator and added 50 μl to each well of pre-chilled white, clear bottom 96-well plate. Incubated for 30 min to facilitate the gel formation. HUVEC cells were harvested using enzyme free cell dissociation buffer and resuspended in ECM (0.2% FBS) and treated with 1.3 nM VEGF and different concentrations of GU40C4 peptoid and 10 μM control peptoid, GU40C (monomer) and GU40CC (ineffective dimer) as the controls. 150 μl of these treated cell suspension (20,000 cells) was added per well and incubated at 37° C. and visualized tube formation under the light microscope after 16 hours (10× magnification).

Cell Culture. The human Ewing's sarcoma cell line A673 (CRL-1598, ATCC, Manassas, Va.) was grown as a monolayer in Dulbeco's minimal essential medium (Invitrogen, Carlsbad, Calif.) supplemented with 10% heat-inactivated fetal calf serum (Atlanta Biologicals, Lawrenceville, Ga.). Cells were maintained at 37° C. in a mixture of 5% CO$_2$ and 95% air. Cell viability was monitored by Trypan Blue (Invitrogen, Carlsbad, Calif.) exclusion after trypsinization. Cell fingerprinting was performed by Dr. Luc Girard at the McDermott Center at UT Southwestern to verify identity of cells and the cells were also tested and found to be negative for *Mycoplasma* prior to use.

Tumor study. Tumors were established in the right flank of 6-8 week old female athymic nu/nu mice (NCl, Frederick, Md.) by subcutaneous injection of 2.5 million cells in a volume of 50 μl PBS. On the same day, an Alzet subcutaneous pump (DURECT Corporation, Cupertino Calif.) was implanted per manufacturer's recommendations. Briefly, the pumps were filled with 100 μl of GU40C4 or control peptoid (8 mg/ml in saline). Pumps were weighed empty and again when filled to ensure correct loading. Based on the mean pumping rate (0.2 μl/hr), these pumps were predicted to elute for 21 days. Implantation of the pump was performed by making a small incision on the back of the anesthetized animal and subsequently using a hemostat to create a subcutaneous pocket in which to place the pump. The incision was closed with a 5-0 prolene (Ethicon, Somerville, N.J.). Animal weights and tumor volumes (calipers) were recorded twice weekly. Volumes were calculated using the formula $D*d^2*0.52$ where D is the long diameter and d is the perpendicular short diameter. All animal experiments were approved by and performed in accordance with the Institutional Animal Care and Use Committee of UT Southwestern.

Immunohistochemistry. Formalin-fixed tissues were embedded in paraffin, sectioned and stained with hematoxylin and eosin by the Molecular Histopathology Laboratory at UT Southwestern. H&E photographs were taken at a total magnification of 40× on a Nikon DXM 1200 digital camera (Melville, N.Y.). For immunohistochemical staining, slides were deparaffinized by heating at 60° C. for one hour followed by immersion in xylenes. Tissue was rehydrated by sequential immersion in ethanols. Endogenous peroxidase activity was blocked with 3% H$_2$O$_2$ in methanol. Antigen retrieval was performed using pH 6.0 citrate buffer (LabVision, Freemont, Calif.) for 15 minutes in a pressure cooker. Sections were blocked with 20% Aquablock (EastCoast Bio, North Berwick, Me.) and subsequently incubated overnight at 4° C. with 1:25 dilution of rat anti-mouse CD34 (ab8158, Abcam, Cambridge, Mass.). The primary antibody was detected by incubating with a biotinylated donkey anti-rat IgG (Jackson ImmunoResearch, Westgrove, Pa.) followed by the ABC detection kit (Vector laboratories, Burlingame, Calif.). Subsequent DAB (Invitrogen, Carlsbad, Calif.) detection was performed and slides were counterstained with hematoxylin (Richard Allan Scientific, Kalamazoo, Mich.) and mounted with Crystal/Mount (Biomeda, Foster City, Calif.). Microvessel density (MVD) was determined by manually counting the number of blood vessels in visible in the microscopic field of view (total magnification, 100×). Five fields were taken for each slide (n=3 per group).

B. Results

A cell-based binding screen for the isolation of VEGFR2-binding peptoids. The inventors have shown previously that combinatorial libraries of peptoids (N-alkylglycine oligomers) are a rich source of ligands for many different proteins (Alluri et al., 2006; Alluri et al., 2003; Bachhawat-Sikder and Kodadek, 2003; Liu et al., 2005; Reddy et al., 2004). These experiments involved the synthesis of a "one bead-one compound" library in which each bead displays many copies of a unique peptoid. The fluorescently-tagged protein target is introduced to the bead library in the presence of a large excess of unlabeled competitor proteins (i.e., in a crude lysate) and the few beads in the library that retain the protein are identified by automated or manual detection of the most highly fluorescent beads. A significant drawback to applying this protocol to the isolation of peptoid ligands for integral membrane proteins such as VEGFR2 is that these receptors are often not well-behaved biochemically. Various strategies have been introduced to cope with this problem, for example the expression of an isolated extracellular domain or the incorporation of the full-length protein into synthetic micelles or vesicles (Robelek et al., 2007). However, all of these approaches have well-documented drawbacks, and the inventors wished to develop a new type of assay that would allow the library to be screened against the full-length receptor in as natural an environment as possible.

Therefore, the inventors developed the assay shown in FIG. 1A. Porcine aortic endothelial (PAE/KDR) lacking the human VEGFR2 were labeled with green-emitting quantum dots and the same cells, but including a vector that directs expression of human VEGFR2, were labeled with red-emitting quantum dots. Note that the quantum dots were internalized into the cell and thus should not affect their surface characteristics. In theory therefore, the only difference between the two differentially labeled cell types should be the presence or absence of the target receptor. If a 1:1 mixture of the red- and green-labeled cells are incubated with the bead library, then beads that bind only red and not green cells would be expected to display peptoids that are specific VEGFR2 ligands (FIG. 1A).

To execute this strategy, the inventors synthesized a library of peptoids with a theoretical diversity of approximately 250,000 compounds on TentaGel beads. The design of the library (FIG. 1B) attempted to take some advantage of the structure of the VEGF-VEGR2 complex. The receptor consists of seven extracellular immunoglobulin-like domains, a single transmembrane region, and an intracellular tyrosine kinase domain (Matthews et al., 1991; Terman et al., 1991). VEGF binds to extracellular domains 2 and 3 (Fuh et al., 1998) of VEGFR2. It has been reported that Isoleucine (Ile-43, 46, 83), Glutamate (Glu-64), Phenylalanine (Phe-17), Glutamine (Gln-79), Lysine (Lys-84) and Proline (Pro-85) side chains of VEGF are the most important moieties for the binding to VEGFR2 (Muller et al., 1997). Therefore, in designing this peptoid library, the inventors decided to have at least two of the above residues fixed with the intent of biasing the library for VEGFR2 binding. The inventors selected Lys-like and Leu-like residues to be fixed at the C-terminus of each molecule in the library. Leu was chosen instead of Ile because Ile was not validated for peptoid synthesis at the time of synthesis, and Leu was the most suitable substitute. Also, the inventors decided to place one additional Lys-like residue in between the resin and the 8-mer peptoid, making the full length of each peptoid nine residues. The positively charged Lys-like residue can repel the peptoids from each other on the bead surface and would avoid aggregation of the peptoids that could hinder proper display. The library was synthesized on TentaGel macrobeads (140-170 µM diameter), which have excellent stability and swelling properties and also provide a non-sticky surface that is ideal for reducing non-specific binding in screening experiments (Alluri et al., 2003). Synthesis of the library was conducted using eight different amines (FIG. 1B) resulting in a theoretical diversity of 262, 144 compounds.

Figure 2:
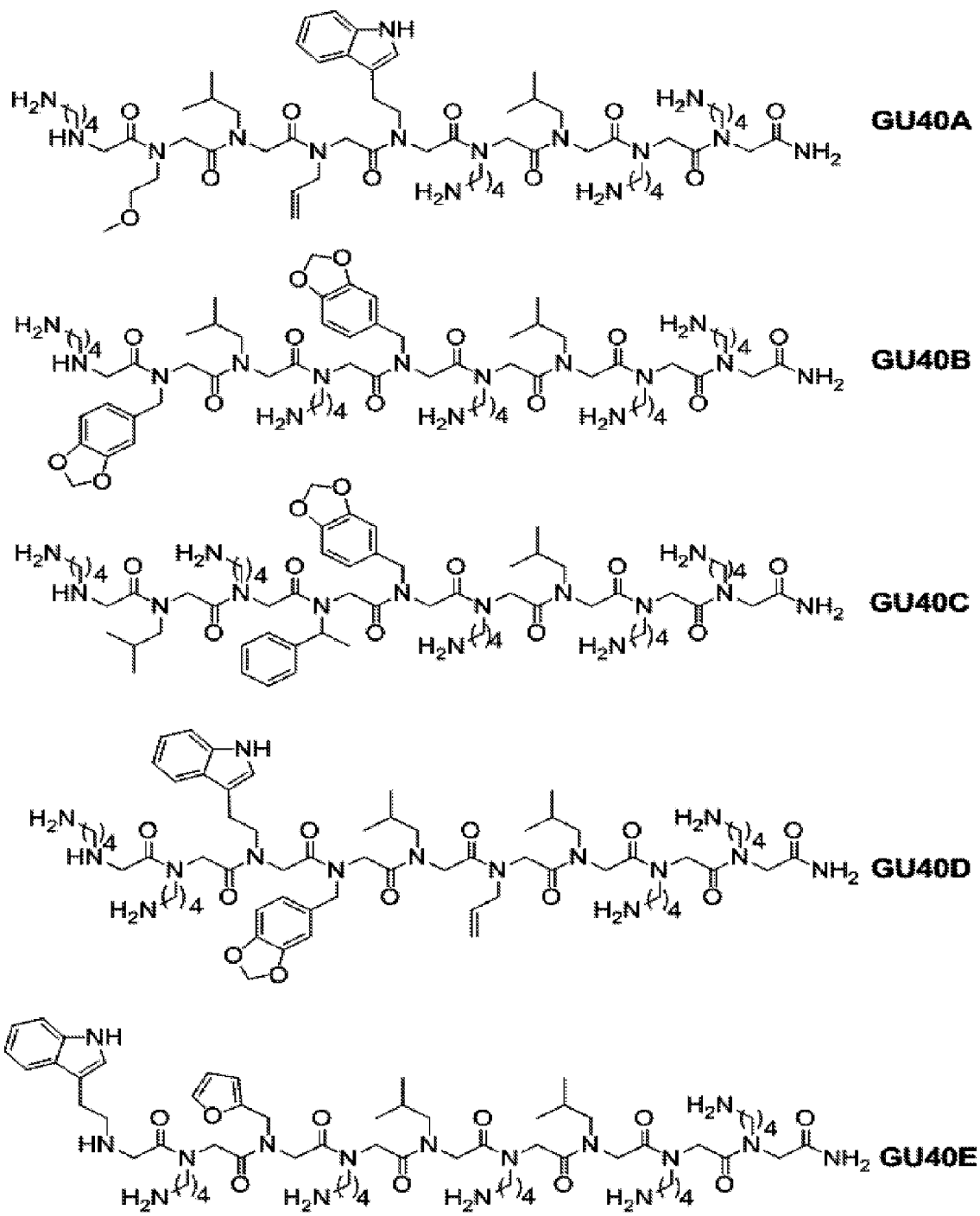
FIG. 2. Chemical structures of identified 'hit' compounds from on-bead cell screening GU40A. Nlys-Nmea-Nleu-Nall-Ntrp-Nlys-Nleu-Nlys-Nlys; GU40B: Nlys-Npip-Nleu-Nlys-Npip-Nlys-Nleu-Nlys-Nlys; GU40C: Nlys-Nleu-Nlys-Nmba-Npip-Nlys-Nleu-Nlys-Nlys; GU40D: Nlys-Nlys-Ntrp-Npip-Nleu-Nall-Nleu-Nlys-Nlys; GU40E: Ntrp-Nlys-Nffa-Nlys-Nleu-Nlys-Nleu-Nlys-Nlys FIGS. 3A-B. The peptoids GU40C and GU40E are VEGFR2 ligands.

The screen consisted of mixing a 1:1 ratio of the aforementioned red- and green-stained cells with the peptoid-displaying beads for 60-75 min at 37° C. After washing, the beads were examined under a fluorescence microscope with irradiation through a standard DAPI filter (FIGS. 1C and 1D). When irradiated at this wavelength, the polystyrene-based beads fluoresce blue whereas the quantum dots emit red and green light, respectively, allowing simultaneous visualization of the beads and both the cells lacking and containing VEGFR2. Three screens, each using about 100,000 beads, were conducted. As expected, in each case the vast majority of the beads did not bind either green or red cells. A much smaller number were observed to bind both the red- and green-stained cells approximately equally (large blue sphere with both green and red speckles indicated with the arrow in FIG. 1C). These beads presumably display peptoids that bind to molecules present on the surface of both cell types. These were not characterized further. Only five of the approximately 300,000 beads screened (approximately 0.0017% of the population) were observed to bind red-stained cells only. One such bead is shown in FIG. 1D. These putative "hits" were collected using a micropipette and placed into separate tubes. They were then boiled in an SDS-containing solution to remove cells, proteins and other extraneous matter and, after washing with aqueous buffer, subjected to automated Edman degradation to determine their sequence. The deduced structures of the putative VEGFR2-binding peptoids are shown in FIG. 2.

The isolated peptoids are VEGFR2 ligands. Two of the 'hits' from this screen, GU40C and GU40E (see FIG. 2) were resynthesized, both as free compounds and with C-terminal Cys (for C-terminal fluorescein tagging via maleimide chemistry), cleaved from the beads and purified to apparent homogeneity by reverse phase HPLC. These compounds were chosen initially because they had the widest structural differences among the isolated peptoids and also inspection of their sequence suggested that they would be the most water-soluble peptoids. The association of these peptoids with VEGFR2 was evaluated using an ELISA-like assay. A commercially available fusion protein containing the VEGFR2 extracellular domain (amino acids 1-764 fused to 6× histidine-tagged Fc of human IgG, via the peptide IEGRMD; R&D Systems) was plated into 96-well plates and then mixed with various concentrations of N-terminally Fluorescein (FITC)-labeled peptoid. After washing away unbound peptoid, the remaining fluorescence emission signal was measured at 520 nm. In this assay purified VEGFR2 protein was used instead of the whole PAE/KDR cells that over express VEGFR2, in order to confirm these compounds were binding only to the receptor.

Figure 3:
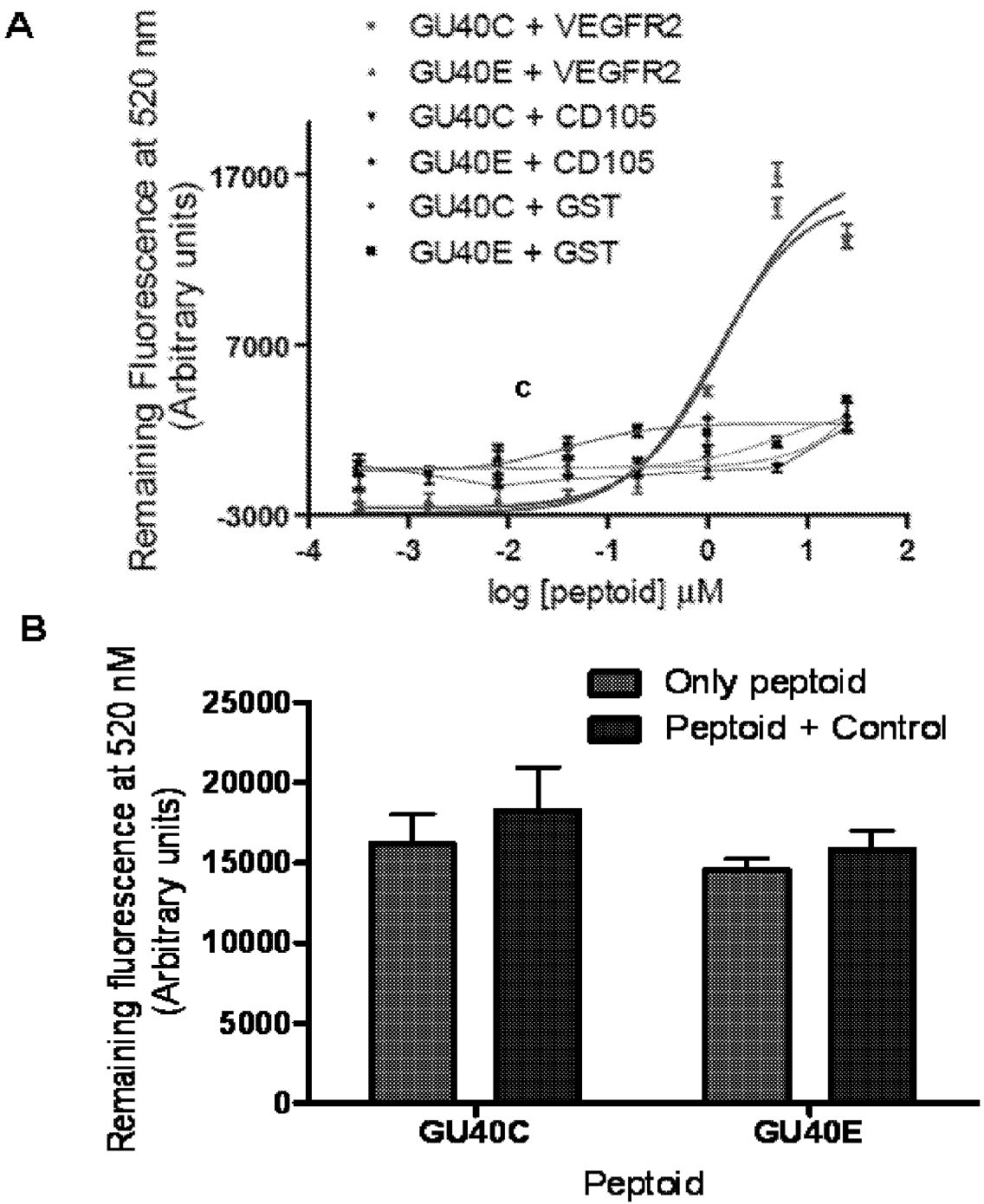
(FIG. 3A) Binding isotherms of fluoreceinated peptoids GU40C and GU40E against immobilized VEGFR2, CD105 and GST proteins evaluated by ELISA-like assay using immobilized. Data points represent mean of duplicate measurements with error bars corresponding to the standard error of the mean.
(FIG. 3B) Binding competition of fluoresceinated GU40C and GU40E peptoids with control peptoid to VEGFR2 evaluated by ELISA-like assay. Both peptoids were at 1 µM and control peptoid was at 10 µM. No significant disruption of the selected peptoid-VEGFR2 complexes by the control peptoid was observed. Data points represent the mean of duplicate measurements with error bars corresponding to the standard error of the mean.

As shown in FIG. 3A and Table 3, the peptoids were indeed found to behave as specific VEGFR2 ligands with dissociation constants (KDs) of about 2 µM. These values are similar to (Zilberberg et al., 2003), or better than (Binetruy-Tournaire et al., 2000; Hetian et al., 2002) those reported previously for peptidic VEGFR2 ligands. GU40C and GU40E did not bind detectably to CD105, another endothelial cell surface receptor, or GST, in the same assay (FIG. 3A). Conversely, a control peptoid not selected to bind VEGFR2 did not compete with GU40C or GU40E for binding to VEGFR2 (FIG. 3B). Finally, if the immobilized receptor was pre-incubated with unlabeled VEGF, almost no binding of fluoresceinated GU40C or GU40E could be observed, showing that these peptoids compete for the hormone for binding to VEGFR2 (not shown). The inventors conclude that peptoids GU40C and GU40E are indeed specific ligands for human VEGFR2.

Functional characterization of the VEGFR2-binding peptoids. GU40C and GU40E were then tested for their ability to modulate VEGFR function. Of course, since the screen simply demanded binding of the peptoid to the receptor, it was not a given that this would be the case. An early step in the angiogenesis cascade is auto phosphorylation of the VEGFR2 intracellular kinase domain upon VEGF binding. In order to test whether the VEGFR2-binding peptoids could mimic or inhibit this VEGF-induced VEGFR2 phosphorylation, the inventors incubated PAE/KDR cells that over express VEGFR2 with or without 1.3 nM VEGF and/or several different concentrations of the peptoid ligands. Western blot analysis using phospho-VEGFR2-specific antibodies was then employed to monitor receptor activation. Neither peptoid at any concentration tested evinced agonist activity in the absence of VEGF.

Figure 8:
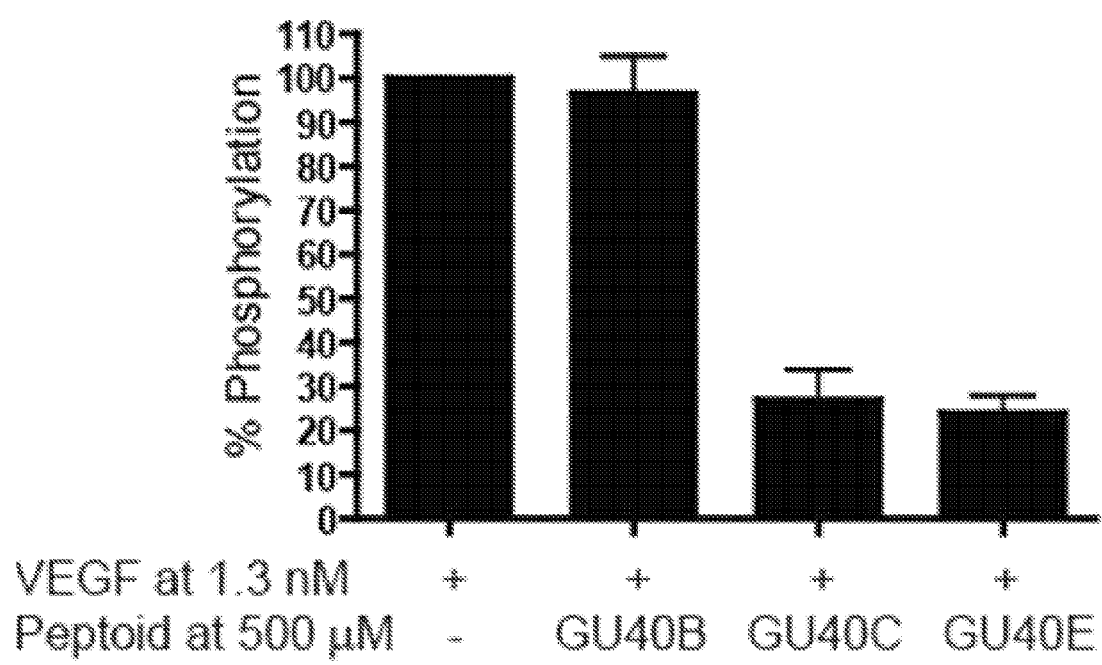
FIG. 8. Quantification of the % phosphorylation of above western blot analysis of three monomeric peptoids GU40B, GU40C and GU40E in PAE/KDR cells under 1.3 nM VEGF induction. All three peptoids were used at 500 µM concentration. Peptoid GU40B had no effect while GU40C and GU40E antagonized VEGFR2 phosphorylation by approximately 75%.

Instead, both GU40C and GU40E appeared to be weak antagonists of VEGF dependent VEGR2 autophosphorylation. At a peptoid concentration of 500 μM, an approximately 75% inhibition of phosphorylation was observed (FIG. 8). Note that that the hormone-receptor complex is extremely stable ($K_D \approx 50$ μM) (Fuh et al., 1998). Thus, the weak antagonistic activity of these μM affinity peptoid ligands was not unexpected, but does highlight the requirement for a major increase in binding affinity if these molecules are to be of practical utility.

High Affinity Dimeric VEGR2-Binding Peptoids. Much of the high affinity of the VEGF-VEGR2 complex derives from the fact that the hormone and receptor are both native dimers and associate in a 2:2 complex. Indeed, while the $K_D$ of the $(VEGF)_2 \cdot (VEGFR)_2$ complex is 50 μM, a monomeric derivative of VEGF binds to the VEGR2 receptor dimer with an affinity of only 1.5 μM (Fuh et al., 1998), a value quite similar to that exhibited by the GU40C and GU40E peptoids. Therefore, the inventors hypothesized that a large increase in affinity could be achieved by joining two molecules of either peptoid with an appropriate linker.

Figure 4:
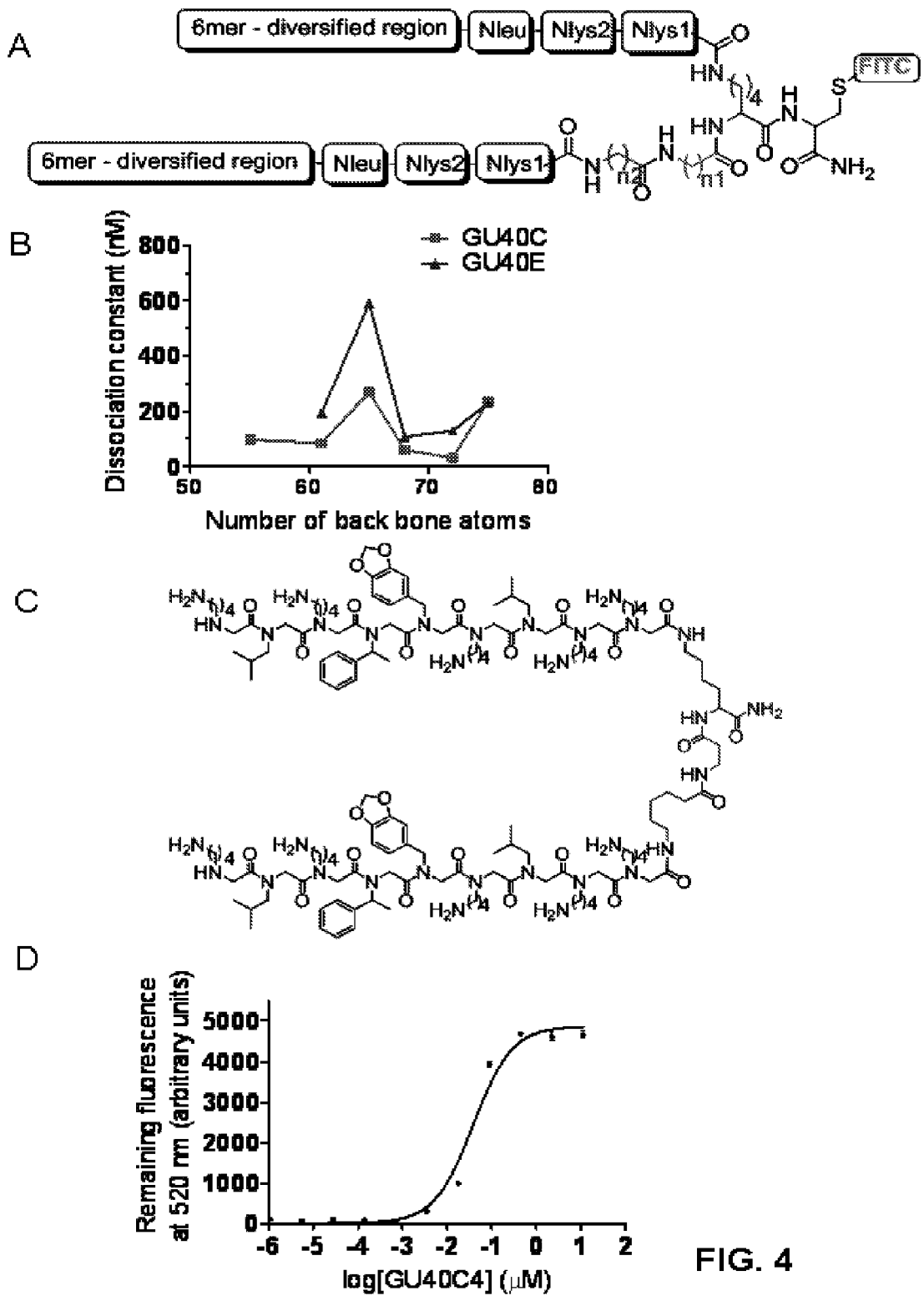
FIGS. 4A-D. Dimeric peptoid design and binding evaluation.

The VEGFR2 binding regions of the dimeric hormone are separated by approximately 70 Å (Wiesmann et al., 1997). Therefore, the inventors synthesized and characterized homodimeric derivatives of GU40C and GU40E with central Lys linker and additional linker arms that would place the N-termini of each peptoid between approximately 45-85 Å apart if the linkers were in their fully conformation. This was accomplished by using linkers with different numbers and combinations of β-alanine and aminohexanoic acid units (FIG. 4A; Table 3, GU40C1-5 and GU40E1-5). In addition, shorter dimers were obtained for compound GU40C by avoiding the additional linker region and also by truncating the three fixed C-terminal residues one at a time (FIG. 4A; Table 3, GU40CAC).

The binding of each of these dimeric peptoids to VEGFR2 was analyzed using the same ELISA-like method used for the monomeric ligands. As shown in FIG. 4B and Table 3, all of the longer dimeric peptoids exhibited improved affinity for the receptor, but the degree of improvement varied substantially depending on the nature of the linker. The best result was obtained with GU40C4 (FIG. 4C), which bound VEGFR2 with an apparent KD of 32 μM (FIG. 4D), an improvement of about 90-fold relative to the monomeric parent compound. This low nM dissociation constant is similar to that exhibited by some monoclonal antibodies for VEGFR2 ((Brekken et al., 1998; Lu et al., 2002) even though this compound is far smaller than an antibody. Therefore, GU40C4 was chosen for further study.

Specificity of the GU40C4-VEGFR2 interaction on the cell surface. To evaluate the specificity of the high affinity dimeric peptoid for VEGFR2, various cell types were incubated with biotinylated GU40C4 peptoid and association of the small molecule with the cells was probed using streptavidin conjugated red quantum dots (Qtracker 655) (FIGS. 5A-H). The DAPI-stained nuclei are shown in blue. GU40C4 binding to PAE/KDR cells that overexpress VEGFR2 was seen clearly (FIG. 5A), as expected. This intense red signal disappeared completely in the presence of 100-fold excess unlabeled GU40C4 (FIG. 5B). In addition, the red halo was not observed when the VEGFR2-expressing PAE/KDR cells were incubated with only the streptavidin-coated red quantum dots without addition of the biotinylated peptoid (FIG. 5C). Finally, biotinylated GU40C4 did not bind detectably to the PAE parental cells lacking the VEGFR2 expression vector (FIG. 5D). Together, these data demonstrate that GU40C4 binds specifically to VEGFR2 and does not associate detectably with other cell surface molecules displayed by the cell.

An important question is whether the peptoid is able to recognize VEGFR2 on the surface of cells when the receptor is expressed at native levels. To address this question, the inventors incubated biotinylated CU40C4 and streptavidin-coated red quantum dots with four different cell lines: HeLa,

TABLE 3

Dimeric peptoid library design and their binding study results

| Peptoid series | Peptoid name | Structural features | | | | | $K_D$ (nM) | Fold improved |
|---|---|---|---|---|---|---|---|---|
| | | n1 | n2 | Nleu | Nlys2 | Nlys1 | | |
| GU40C | GU40C | — | — | Y | Y | Y | 2854 ± 400 | x |
| | GU40C1 | N | N | Y | Y | Y | 85.7 ± 4.0 | 33 |
| | GU40C2 | 2 | N | Y | Y | Y | 268.7 ± 41.8 | 11 |
| | GU40C3 | 5 | N | Y | Y | Y | 60.6 ± 23.4 | 47 |
| | GU40C4 | 2 | 5 | Y | Y | Y | 32.1 ± 4.9 | 89 |
| | GU40C5 | 5 | 5 | Y | Y | Y | 234.2 ± 0.1 | 12 |
| | GU40CA | N | N | Y | Y | N | 97.5 ± 22 | 30 |
| | GU40CB | N | N | Y | N | N | weaker | — |
| | GU40CC | N | N | N | N | N | weaker | — |
| GU40E | GU40E | — | — | Y | Y | Y | 1213.1 ± 140 | x |
| | GU40E1 | N | N | Y | Y | Y | 193.6 ± 21 | 6 |
| | GU40E2 | 2 | N | Y | Y | Y | 591.1 ± 70 | 2 |
| | GU40E3 | 5 | N | Y | Y | Y | 107.9 ± 9 | 11 |
| | GU40E4 | 2 | 5 | Y | Y | Y | 129.3 ± 12 | 9 |
| | GU40E5 | 5 | 5 | Y | Y | Y | 230 ± 39 | 5 |

GU1040C1-5 and GU40E1-5 represent the longer dimers and GU40CA-C were shorter dimers. In both longer and shorter dimers, two monomeric units (with or without linker region) were linked together via amide bond formations between C-terminal carboxylic acid moiety and each one of the amine groups on Lys side chain and N-terminus (FIG. 4A).
Under structural features column, Y = present and N = absent of the corresponding moiety. The values on n1 and n2 columns are the number of carbon atoms present in that region.
$K_D$ values are in nM and the final column show how many fold the binding was improved compared to the monomer in each case.
[a]$K_D$ values were determined by ELISA-like assay.

HEK-293, human foreskin fibroblast (HFF) and MCF-7. Of these, only MCF-7 expresses significant quantities of the VEGFR2. As seen in FIG. 5D-5H, the red halo was observed only when the peptoid was incubated with the MCF-7 cells (see FIG. 5G). The inventors conclude from these experiments that the dimeric peptoid is highly specific for the VEGFR2 and can recognize the receptor even when it is expressed at native levels on the surface of a breast cancer cell.

Figure 6:
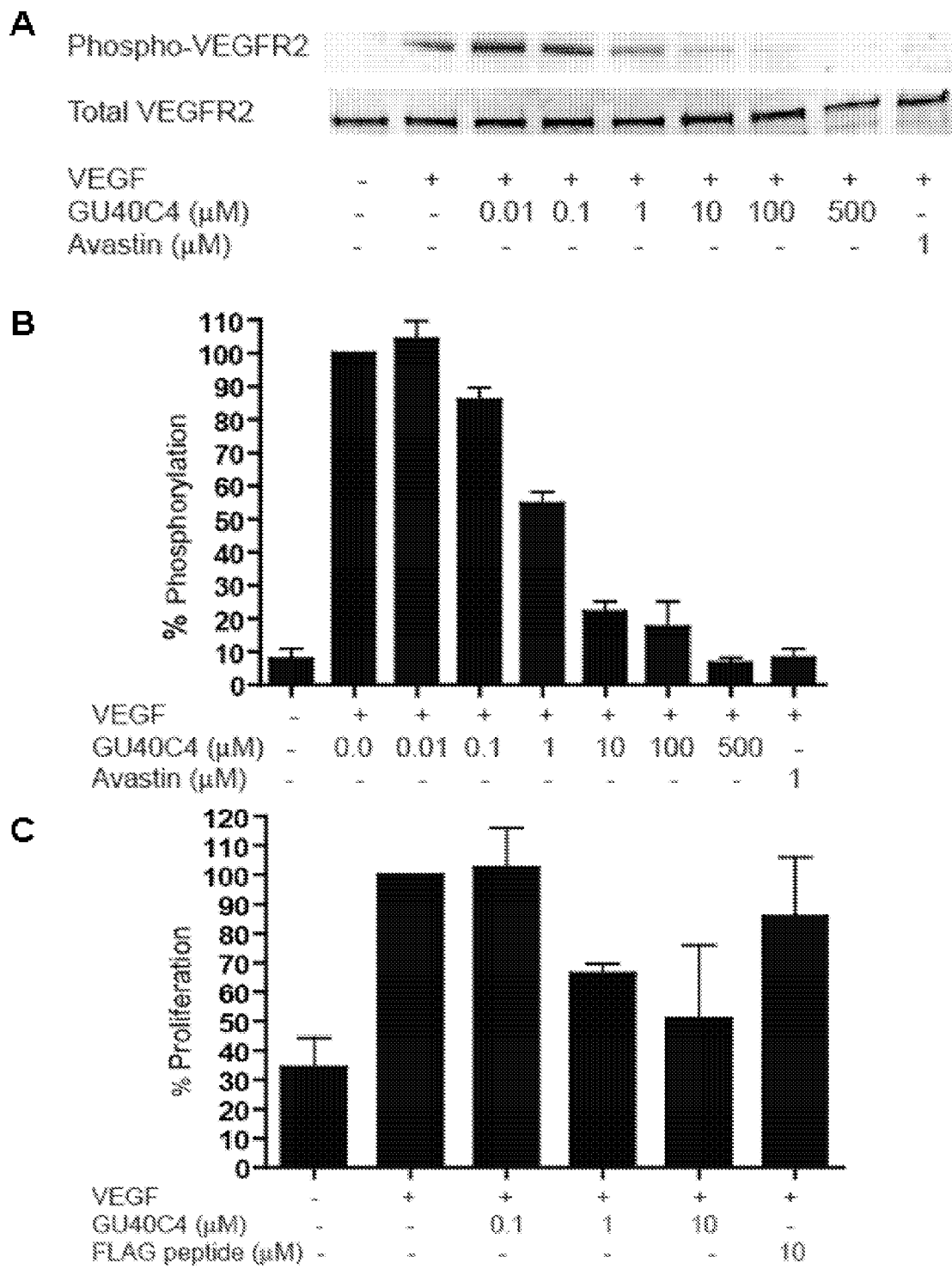
FIGS. 6A-C. Effects of GU40C4 on VEGF-induced, VEGFR2-dependent functions.
Figure 9:
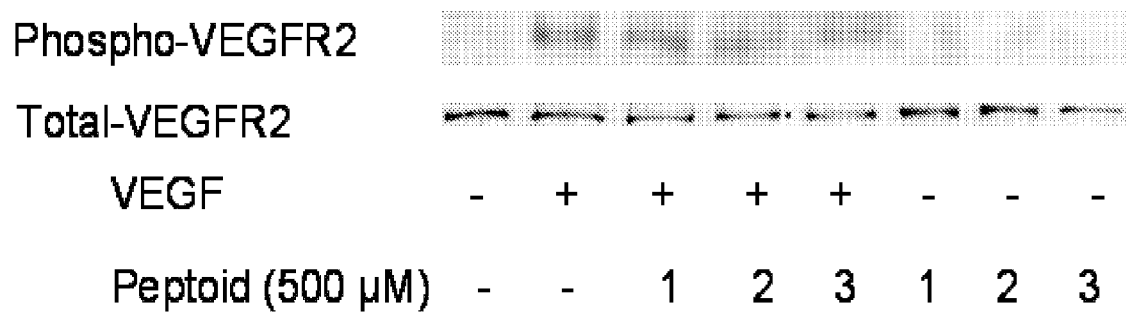
FIG. 9. Western blot analysis of monomers affecting on VEGF induced VEGFR2 phosphorylation. Western blot analysis of three monomeric peptoids (1: GU40B, 2: GU40C, 3: GU40E) to detect VEGFR2 phosphorylation levels in PAE/KDR cells under 1.3 nM VEGF induction. All three peptoids were used at 500 µM concentration. None of the peptoids exhibited agonist activity. GU40C and GU40E were weak antagonists.
Figure 11:
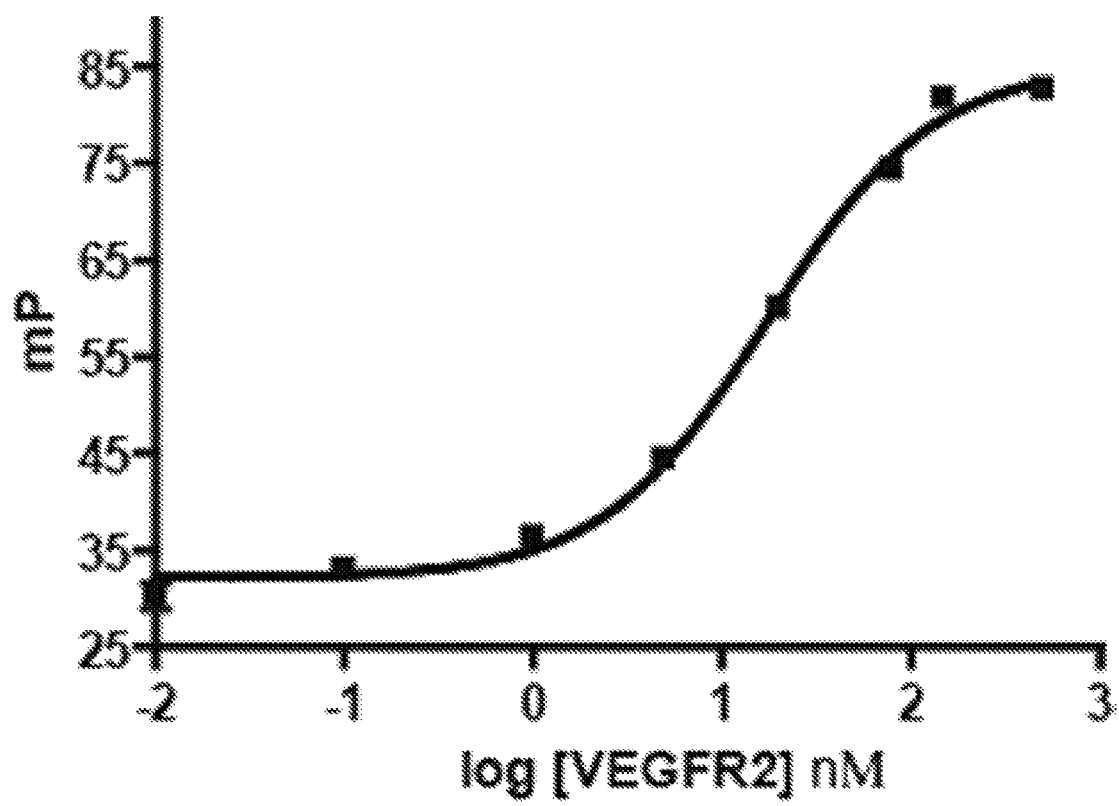
FIG. 11. Binding isotherm of GU40C4 derived from Fluorescence Polarization. Binding isotherm of GU40C4 derived from fluorescence polarization experiments. 0.5 nM fluoresceinated GU40C4 was treated with increasing amounts of soluble VEGFR2. $K_D \approx 20$ nM.
Figure 12:
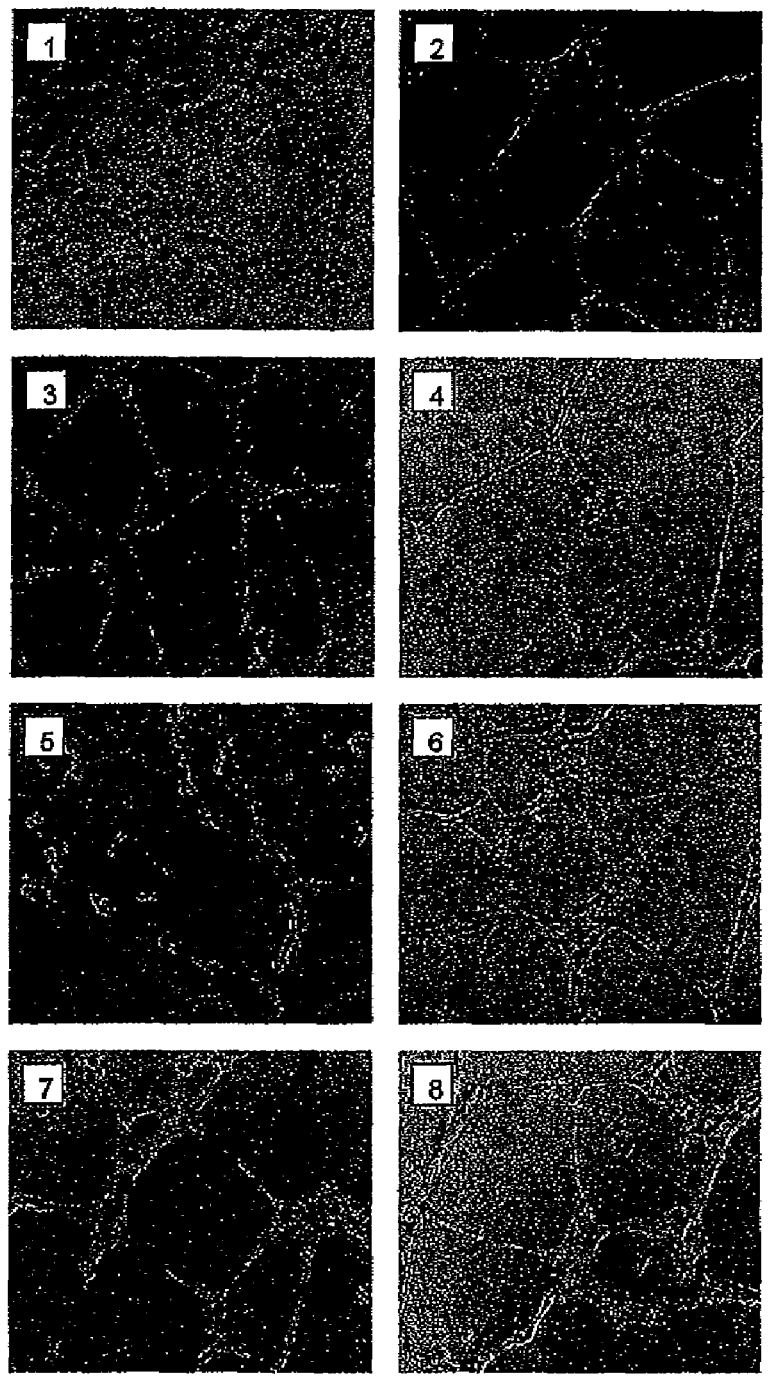
FIG. 12. HUVEC Tube formation assay; GU40C4 inhibits VEGF-induced tube formation in vitro. HUVECs were grown on endothelial cell medium gel, and treated with 1.3 nM VEGF and different amounts of GU40C4, or 10 μM control peptoid, GU40C (monomer) or GU40CC (ineffective dimer). (Panel 1) without VEGF treatment, (Panel 2) VEGF only, (Panel 3) VEGF+0.1 μM GU40C4, (Panel 4) VEGF+1 μM GU40C4, (Panel 5) VEGF+10 μM GU40C4, (Panel 6) VEGF+10 μM control peptoid, (Panel 7) VEGF+10 μM GU40C (monomer), (Panel 8) VEGF+10 μM GU40CC (ineffective dimer). GU40C4 disrupted HUVEC tube formation at 1 μM and 10 μM concentrations. Control peptoid and GU40CC (ineffective dimer) had no detectable effect on HUVEC tube formation at 10 μM. GU40C (monomer) had a small effect. Images were taken at 100× total magnification and each experiment was repeated three times.

GU40C4 is a relatively potent antagonist of VEGF-dependent receptor activation. Having demonstrated that GU40C4 is a high affinity and high specificity ligand for the VEGFR2, the inventors next asked if it is capable of antagonizing receptor function in vitro. To do so, the inventors examined the effect of the peptoid on VEGF-induced VEGFR2 autophosphorylation by Western blotting, as described earlier. VEGFR2 over-expressing PAE/KDR cells were induced with 1.3 nM VEGF in the presence of the indicated concentrations of GU40C4 (FIG. 6A). Subsequent measurement of the fraction of VEGFR2 that had undergone autophosphorylation demonstrated that the GU40C4 peptoid is indeed an antagonist of receptor activation with an $IC_{50}$ value of approximately 0.9 μM (FIGS. 6A and 6B). This represents an improvement of between 100- to 500-fold over the monomeric parent compound (FIGS. 8 and 9), consistent with the increased affinity of the dimeric peptoid for the receptor. Under the same conditions, 1 μM Avastin, the ultra-high affinity anti-VEGF antibody employed clinically, completely blocked VEGFR2 autophosphorylation (FIGS. 6A and 6B).

The inventors also studied the ability of GU40C4 to inhibit VEGF-induced proliferation of human vascular endothelial cells (HUVECs). HUVECs were grown in 96-well plates and treated with 1.3 nM VEGF to induce proliferation. Various concentrations of GU40C4 were added as a competitor and the effects were monitored after 4 days. As expected, GU40C4 was able to inhibit VEGF-induced HUVEC proliferation with an $IC_{50}$ of approximately 1 μM. At 10 μM peptoid, cell proliferation was reduced to essentially basal levels (FIG. 6C). FLAG peptide (FIG. 10B), which was used as a negative control, did not show an effect on proliferation at 10 μM.

Finally, the inventors examined the effect of the GU40C4 on the VEGF-induced rearrangement of HUVECs into tubes in an endothelial cell medium (ECM) gel, a commonly used in vitro model for VEGF-induced angiogenesis. HUVECs were grown on ECM gel and treated with 1.3 nM VEGF and different concentrations of GU40C4 or various control compounds, including 10 μM unselected peptoid, GU40C (monomer) and GU40CC (ineffective shortest dimer; Table 3). Clear evidence of the inhibition of tube formation could be seen at GU40C4 peptoid concentrations of 1 μM and 10 μM. The control peptoid and shortest dimer GU40CC with no binding had no effect. A slight effect was observed for monomeric GU40C which is smaller compared to its homodimer. From these experiments, it was concluded that the dimeric peptoid GU40C4 is a relatively potent antagonist of VEGFR2.

Figure 7:
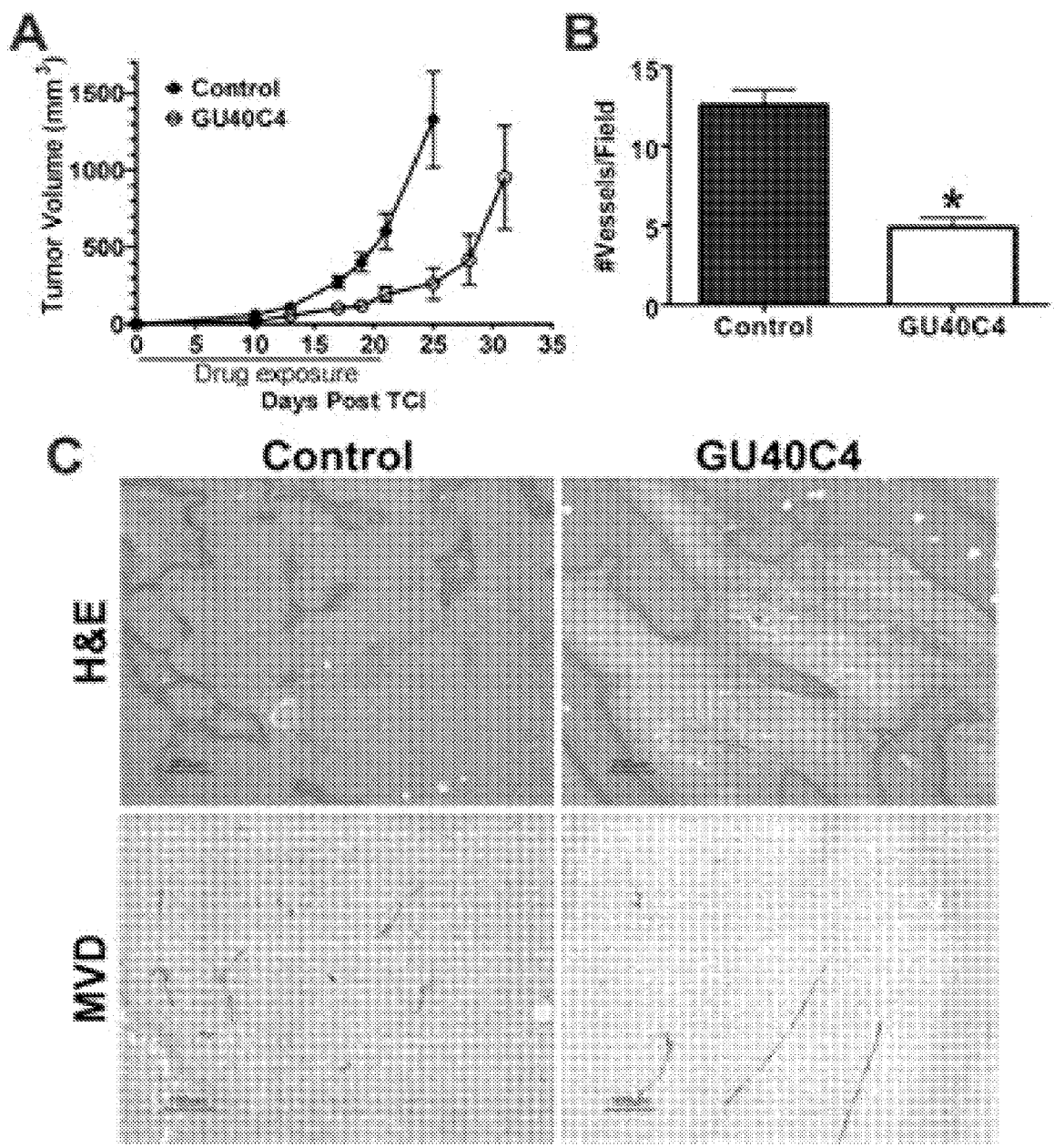
FIGS. 7A-C. Effects of GU40C4 on VEGF-induced tube formation in HUVEC cells. HUVECs were grown on endothelial cell medium gel, and were treated with 1.3 nM VEGF and different competing amounts of GU40C4, or 10 µM control peptoid, GU40C (monomer) and GU40CC (ineffective dimer). (1) without VEGF treatment, (2) VEGF only, (3) VEGF+0.1 µM GU40C4, (4) VEGF+1 µM GU40C4, (5) VEGF+10 µM GU40C4, (6) VEGF+10 µM control peptoid, (7) VEGF+10 µM GU40C (monomer), (8) VEGF+10 µM GU40CC (ineffective dimer). GU40C4 was able to disrupt HUVEC tube formation at 1 µM and 10 µM concentrations. Control peptoid and GU40CC (ineffective dimer) had no detectable effect on HUVEC tube formation at 10 µM. GU40C (monomer) had a small effect. Images were taken at 10× magnification and each experiment was repeated three times.

GU40C4 has in vivo therapeutic efficacy in a preclinical mouse model. Based on the in vitro data showing that GU40C4 blocked VEGF-mediated effects, the inventors hypothesized that the dimeric peptoid would inhibit tumor growth in a murine model. This was tested using A673 (human Ewing's sarcoma) cells implanted into the flank of athymic nude mice. A total of 800 μg of GU40C4 (n=10) or a control peptoid (n=11) was delivered by an osmotic pump that was implanted subcutaneously at a site distant from the tumor on the day of tumor cell injection. The pumps eluted drug at a rate of 0.2 μl/hr continuously for a period of 20.8 days. To validate the control peptoid, the inventors included a group of animals who received only saline (n=6) via the pump. Tumor growth in the saline treated animals did not differ from tumor growth in control peptoid treated animals (data not shown). Importantly, since peptoids have not been examined extensively in animals, we observed no adverse effects of treatment with either GU40C4 or the control peptoid. Animals treated with GU40C4 had a reduced tumor growth rate and significantly smaller tumors at the end of therapy compared to control peptoid treated animals (FIG. 7A). On day 22 post tumor cell injection five animals from each group were sacrificed for histological analysis (FIGS. 7B-C). The inventors continued to follow the remaining animals for ten days to determine the extent of tumor growth delay in the GU40C4 treated animals. Within 3-4 days after cessation of therapy, tumors in the GU40C4 group began to grow at a rate similar to the control treated animals. However, tumors remained small for approximately one week, suggesting that GU40C4 retained some effect after delivery had stopped. Histological analysis revealed that GU40C4 reduced microvessel density by approximately 50% at day 22 post tumor cell injection (p<0.0001, FIG. 7B). Furthermore, GU40C4, but not the control peptoid, induced significant tumor necrosis as evaluated by H&E histology (FIG. 7C). This is particularly striking when considering the smaller size of GU40C4-treated tumors (approximately 200 $mm^3$ at day 22) and the fact that A673 tumors of this size do not typically show evidence of substantial necrosis. These data are consistent with GU40C4-mediated inhibition of VEGF-induced angiogenesis in vivo and further validate our in vitro studies.

C. Discussion

Many hormone-receptor interactions have been identified as therapeutic targets. The VEGF-VEGFR2 complex, in particular, has received much attention given its essential role in angiogenesis. The majority of VEGF pathway inhibitors reported to date are either monoclonal antibodies (Brekken et al., 2000; Gerber et al., 2000; Kim et al., 1993; Prewett et al., 1999), other protein based molecules (Getmanova et al., 2006) or peptides (D'Andrea et al., 2006) targeting VEGF itself or the extracellular domain of one of the VEGF receptors. The considerable success of Avastin, a very high affinity anti-VEGF antibody highlights the utility of this strategy in the treatment of cancer and wet macular degeneration, but also the limitations of therapeutic monoclonal antibodies. These must be injected or infused, have only limited tumor penetrance and are difficult and costly to manufacture in large quantities. More classical small molecules are also used in this arena. Sutent (Sunitinib, Pfizer) (Motzer et al., 2006), Nexavar (Sorafenib, Bayer/Onyx) (Clark et al., 2005) and a few other small molecular VEGF receptor tyrosine kinase (RTK)-targeted drugs have been approved for anti-angiogenic therapy. But due to the structural homology of many different kinase domains, most of these inhibitors show cross-reactivity, decreasing the specificity of the drug (Fabian et al., 2005). Finally, as mentioned above, there are several reports of modest affinity VEGF- and VEGFR2-binding peptides, but the limited serum half-life of these peptides limits their practical utility. Thus, there remains a need for the development of new strategies with which to target the hormone-receptor interaction itself with relatively low molecular weight molecules.

Isolation of receptor-binding peptides as potential antibody surrogates. To circumvent the limitations of current technology mentioned above, the inventors sought to develop a general approach to the isolation of readily synthesized, protease-stable receptor-binding compounds. They chose to employ a peptoid (oligo-N-substituted glycine) library as the starting point. Peptoids have a number of favorable properties for this potential application. They are even more straightforward to synthesize than peptides (Figliozzi et al., 1996), yet are protease-insensitive (Simon et al., 1992). In addition, large collections of peptoids have been shown by us and others to be a rich source of protein-binding ligands (Kodadek et al., 2004). Finally, since the small amounts of peptoid on a single bead in a combinatorial library can be sequenced sensitively by Edman degradation (Alluri et al., 2003) or mass spectrometry (Paulick et al., 2006), no encoding of the library is necessary.

To simplify screening peptoid libraries for ligands to cell surface receptors, the inventors developed the two-color, cell-based screen shown in FIG. 1A. In this approach, the receptor target is introduced into a cell type that does not normally express it. For example, human VEGFR2 was over expressed in PAE cell in this study. These cells are labeled with a red-emitting quantum dot. The parental line lacking the receptor is labeled with green-emitting quantum dots and the cells are then mixed and introduced to the bead-displayed peptoid library. Beads that bind only red cells and not green cells are then identified under a fluorescence microscope and collected. After removing cells and other debris with a denaturing wash, the identities of the putative receptor-binding peptoids are determined by Edman degradation.

This protocol avoids a common problem in targeting integral membrane receptors, which is the poor solubility and biochemical properties of many such proteins, often necessitating the use of detergents, micelles or other problematic reagents in screening experiments using recombinant receptors. In this case, the receptor is displayed in a relatively natural environment on the surface of the cell. Thus, this protocol is less likely to provide hits that do not bind the receptor under native conditions. It is important to point out that this is not the first study to employ cells as the targets in a bead-based screen. In particular, the elegant work of Lam and co-workers (Peng et al., 2006) is noteworthy. They reported a screen of an encoded-bead-based library of peptidomimetic compounds against $\alpha_4\beta_1$ integrin that employed integrin-expressing Jurkat cells. In this case however, the isolation of a specific receptor ligand was dependent on the availability of a known, high-affinity receptor antagonist that could be used as a soluble competitor in the screen. Otherwise most of the beads in the library were covered with cells. The use of the different colored cells that do and do not express the target receptor and the experimental conditions the inventors employed removes this limitation and allows this approach to be applied to almost any cell surface target.

It also means that a ligand for almost any accessible surface of the receptor could be isolated, whereas in the competitive assay of Peng et al. (2006) only bead-displayed molecules that compete with the soluble receptor binding molecule will register. Of course, many cell-based assays have been reported in which some easily monitored cellular event dependent on receptor function, such as activation of a downstream reporter gene, is triggered by a small molecule. But these assays require spatial separation of the cells and molecules into different wells of a microtiter plate and a significant robotics infrastructure to carry out screens of large numbers of compounds. Furthermore, it is always possible to isolate molecules that modulate the reporter event in some other way than by simply binding to the receptor. In contrast, this screen registers only selective binding to the target receptor and requires no specialized equipment other than a fluorescence microscope and can easily accommodate libraries containing hundreds of thousands of molecules. Thus, the inventors believe that the FIG. 1A assay represents a significant advance in receptor screening technology.

Dimeric peptoids as potent VEGFR2 antagonists. As reported above, a screen of more than 250,000 peptoids with the general structure shown in FIG. 1B resulted in the isolation of five hits. Two were subsequently shown to be bona fide VEGFR2 ligands, while the other three remain to be analyzed. Quantitative analysis revealed that the affinity of these peptoids for the receptor's extracellular domain was about 2 µM, a value typical for lead molecules isolated from peptoid libraries under standard conditions. Both peptoids proved to be low-potency antagonists of the hormone-receptor interaction, though this was not demanded in the screen. Since peptoids are peptide-like in their structure, the inventors speculate that the VEGF-binding surface of VEGR2 is a "hot spot" (Clackson and Wells, 1995; Mattos and Ringe, 1996) for binding molecules of this type, leading to a much greater likelihood of isolating molecules that bind this surface. The poor potency of antagonism was expected from the modest affinity of the peptoid and the very high affinity of VEGF for VEGFR2.

Figure 5:
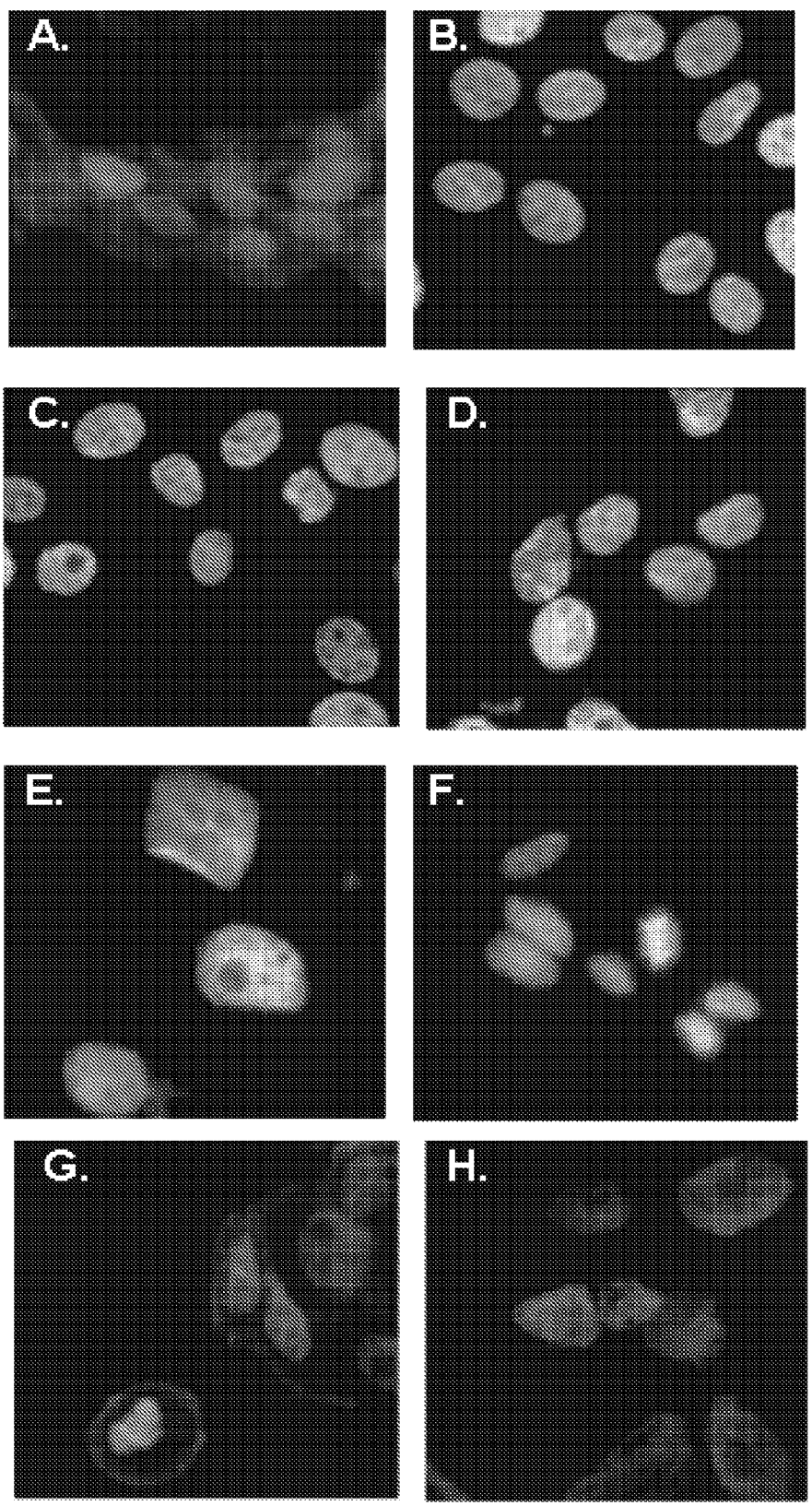
FIGS. 5A-H. Cell specific binding study for GU40C4. All the cells were treated with biotinylated GU40C4 and subsequently with streptavidin-conjugated red quantum dots except for (FIG. 5C), which was treated only with streptavidin-conjugated red quantum dot as a control. The nuclei are stained with DAPI. Fluorescence microscopic images were taken under DAPI filter at 40× magnification.

To achieve higher affinity, the inventors used a simple dimerization approach that takes advantage of the fact that VEGFR2 is a native dimer, as is VEGF. Analysis of a small number of such compounds (FIG. 4 and Table 3) revealed that GU40C4 (FIG. 4C) bound VEGFR2 strongly, with a dissociation constant of approximately 30 nM. A biotinylated version of this compound could be used to visualize the VEGFR2 on the surface of not only the cells used in the screen, but MCF-7 breast cancer cells expressing the receptor at the native level (FIG. 5). The peptoid did not associate detectably with cells that lacked VEGFR2 on their surface (FIG. 5). This is an application for which one normally employs a labeled antibody and highlights the antibody-like binding properties of the peptoid. Yet its molecular mass is similar to that of only a 21-residue peptide. In functional assays, peptoid GU40C4 proved to be a reasonably potent inhibitor of VEGF-dependent VEGFR2 autophosphorylation, endothelial cell proliferation and tube formation by HUVECs (FIGS. 6 and 7) with an $IC_{50}$ of approximately 1 µM. This is in the range of what one would expect for a direct competition between the peptoid and VEGF, given their respective affinities for the receptor ($K_D$s of 30 nM and 50 pm). Since GU40C is a completely unoptimized lead compound, it should be possible to identify derivatives with significantly increased affinity for VEGFR2 and thus reduce the amount of compound necessary to compete the native hormone.

Example 4

Figure 13:
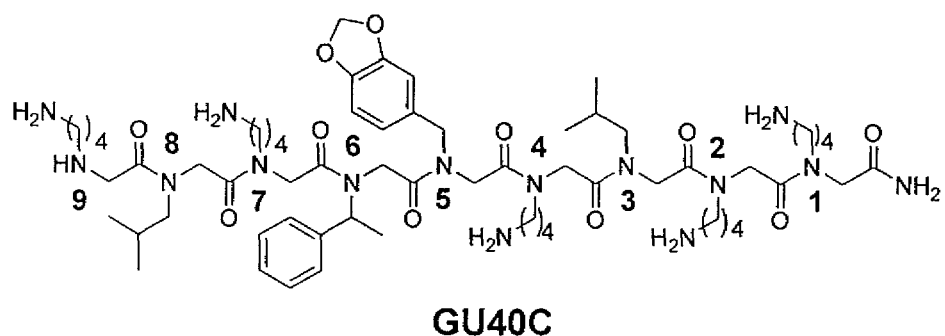
FIG. 13. Annotated Structure of GU40C. Residues are numbered starting from C-terminus.

Rapid identification of the 'minimum pharmacophore' of a lead compound is a vital step in the drug development process since it sets the stage for subsequent optimization. With peptide-based agents, this exercise is simplified by the regular structure of the molecule. A common practice is to evaluate a series of derivatives in which each residue in turn is replaced with a glycine or alanine (alanine scanning) (El Kasmi et al., 1998; Slon-Usakiewicz et al., 1997). Recently, the inventors reported the effective application of glycine scanning to a peptoid (N-substituted oligoglycine) inhibitor of the 19S regulatory particle of the proteasome. This allowed the inventors to create a minimal derivative of the original hit with about half the mass and thus increased cell permeability and potency (Lim et al., 2008). They have also reported the isolation of highly specific peptoid ligands for the extracellular domain of the Vascular Endothelial Growth Factor Receptor-2 (VEGFR2) (Udugamasooriya et al., 2008), an integral membrane receptor that triggers angiogenesis when bound by its cognate hormone VEGF (Ferrara, 2004). A dimerized derivative (GU40C4) of one of these nine residue peptoids (GU40C; see FIG. 13) is a low nM ligand for the receptor's extracellular domain and is a potent antagonist of angiogenesis in vivo (Udugamasooriya et al., 2008). Inhibition of VEGFR2-mediated angiogenesis is a validated strategy to slow the growth of tumors as well as to treat "wet" macular degeneration (Ambresin and Mantel, 2007; Brekken et al., 2000; D'Andrea et al., 2006; Gerber et al., 2000; Getmanova et al., 2006; Hicklin and Ellis, 2005; Hurwitz et al., 2004; Kim et al., 1993; Klohs and Hamby, 1999). Thus, this peptoid is of potential therapeutic interest and its optimization is an important goal. Therefore, the inventors sought to identify the minimal pharmacophore in GU40C as the initial step in this effort.

Figure 14:
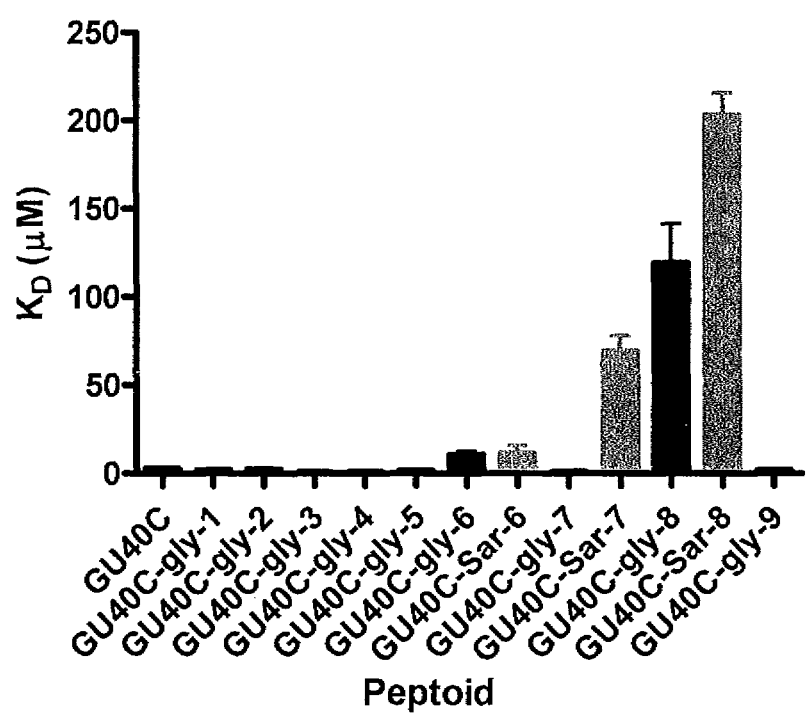
FIG. 14. Glycine (black bars) sarcosine (grey bars) scan binding results of GU40C. Please refer FIG. 13 for residue numbers.

First, nine derivatives of GU40C were synthesized in which each of the nine residues in the parent peptoid was replaced with a glycine. All these derivatives were synthesized with a C-terminal cysteine to facilitate fluorescein attachment via maleimide chemistry. The affinity of each of these derivatives for the extracellular domain (ECD) of VEGFR2 was then determined using an ELISA-like binding assay described in the inventors' previous report (Udugamasooriya et al., 2008). The results are shown in FIG. 14 (black bars). Only two side chains (the $6^{th}$ and $8^{th}$ from the C-terminus) appeared to be important for binding of GU40C to the VEGFR2ECD. To buttress these data, the inventors repeated the analysis, but replaced each monomer in the peptoid with sarcosine rather than glycine. Since secondary amides have a strong preference for a transoid configuration about the peptide bond, while tertiary amides do not, it is possible that glycine substitution could introduce conformational constraints not present in the parent peptoid and thus the comparison of the derivative to the parent molecule might reflect issues other than simply deleting the side chain. For example, if the preferred binding conformation of a peptoid involved a cisoid conformation about a particular peptide bond in the molecule, then replacement of the side chain with a hydrogen would discriminate against this conformation and presumably inhibit binding, even though the side chain was not involved directly. A sarcosine scan has the effect of replacing each of the side chains in turn with a methyl group rather than a hydrogen, preserving the tertiary amide bond, but removing the bulk of the side chain. Therefore, the inventors decided to conduct a sarcosine scan in the region of the molecule identified as being critical for binding by the glycine scan.

As shown in FIG. 14 (grey bars), substitution of the methyl group for isobutyl moiety at position 8 or the α-methylbenzyl group at position 6 weakened binding of the peptoid for the VEGFR2 ECD significantly, consistent with the glycine scan results. However, in contrast with the glycine scanning result, substitution of the lysine-like side chain at position 7 with methyl also reduced binding affinity. This result was confirmed by competition binding assays that compared directly the relative affinities of the peptoids with glycine and sarcosine substitution at position 7. The inventors do not fully understand the basis of the different results obtained using the two scanning methods at position 7. One possibility might be that a polar substituent capable of donating a hydrogen bond to solvent might be favorable there. In any case, the combined data from the glycine and sarcosine scans indicate that the N-terminal region of GU40C, specifically positions 6-8 (see FIG. 13), are important for binding of the peptoid to VEGFR2.

Figure 15:
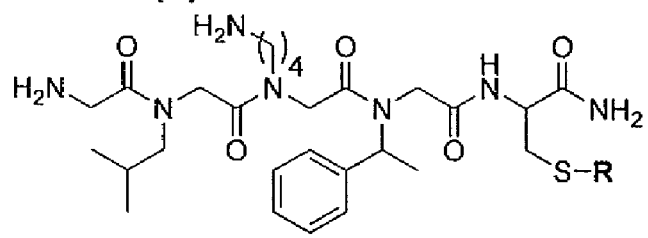
FIGS. 15A-B. Shortest derivative of GU40C which contains only the important side chains and it's binding isotherm.
Figure 15:
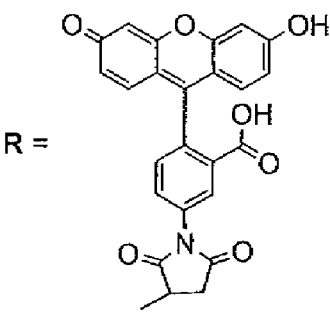
Figure 15:
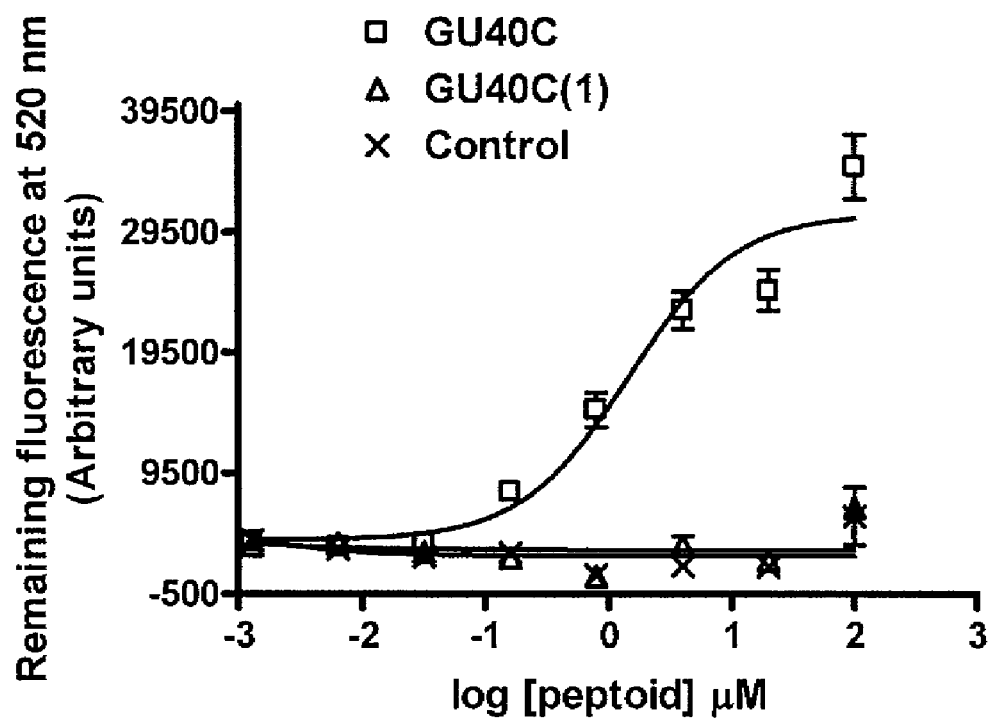

Based on these data, it seemed reasonable to speculate that a trimeric peptoid including positions 6-8 would be a good ligand for the VEGFR2 ECD, an interesting possibility since this molecule would have a mass of less than 450 Daltons. To test this idea, the inventors synthesized a fluorescein-conjugated tetramer peptoid GU40C(1) that contains the three original residues at 6-8 positions along with an N-terminal glycine (FIG. 15A).

The affinity of this minimized GU40C derivative for the receptor ECD was then tested, again using the ELISA-like binding assay. Somewhat surprisingly, this molecule showed no detectable binding to the receptor ECD at any of the concentrations tested (FIG. 15B). Combined with the glycine scanning data shown in FIG. 14, this result suggested the possibility that some of the main chain atoms in the parent peptoid might be involved in receptor binding.

Figure 16:
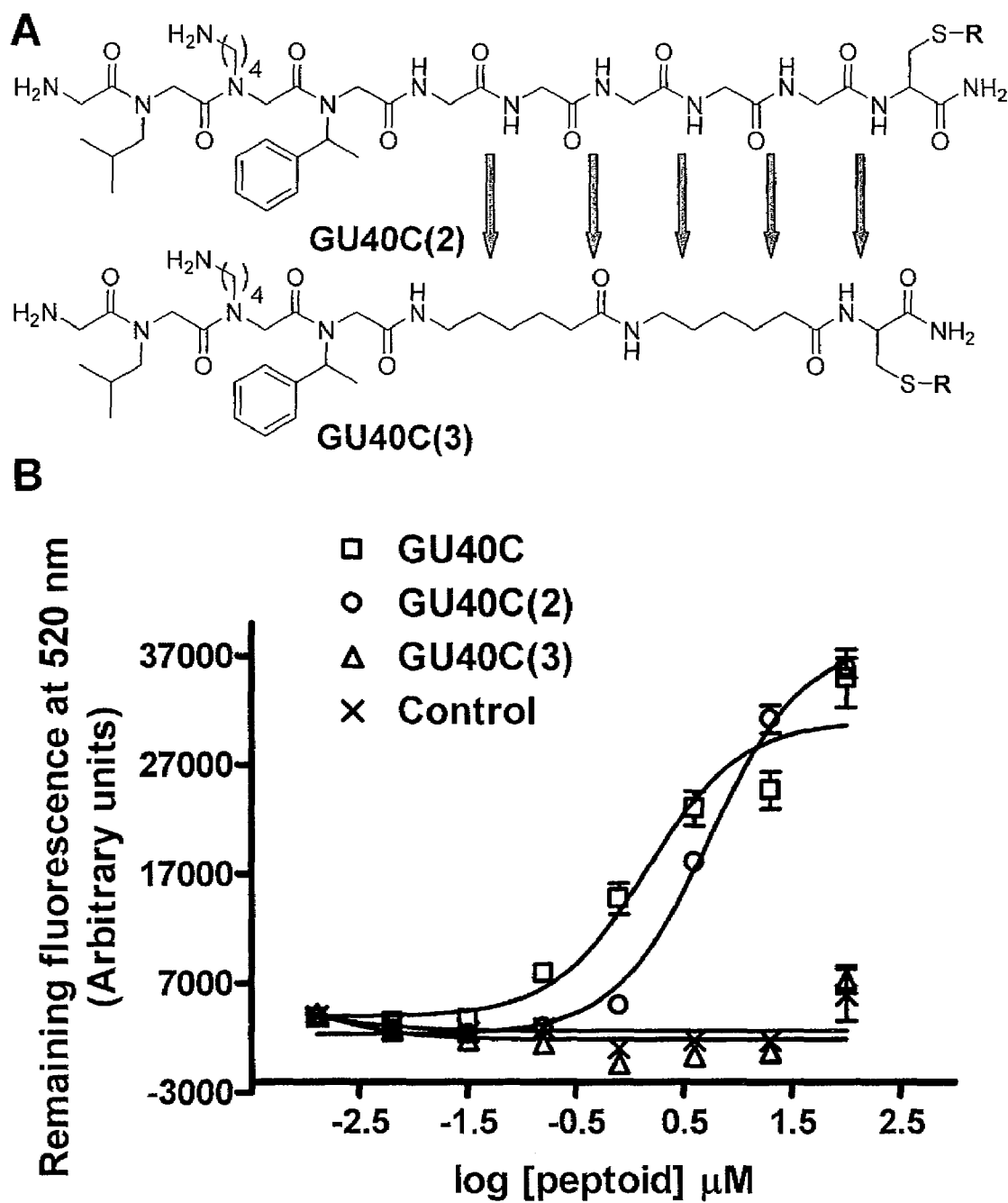
FIGS. 16A-B. Structures and binding isotherms of GU40C and its derivatives.

Therefore, the inventors decided to reintroduce the full backbone, but leave out the side chains, except those important residues at positions 6-8 (GU40C(2)-FIG. 16A, first structure). Interestingly, this compound recognized the receptor ECD with an affinity similar to that of the GU40C parent peptoid (FIG. 16B, square and circle data points), confirming the conclusion derived from the scanning experiments that the side chains at positions 1-5 are not involved in receptor binding. This observation, combined with the sarcosine scanning data, confirm that some of the backbone amide bonds within the first five residues participate in the binding event. The inventors also synthesized and tested GU40C(3) (FIG. 16A), a compound containing the essential side chains and two amide groups C-terminal to these residues, but which are out of register with the amides in the parent peptoid. This compound had no detectable affinity for the receptor ECD (FIG. 16B).

Figure 17:
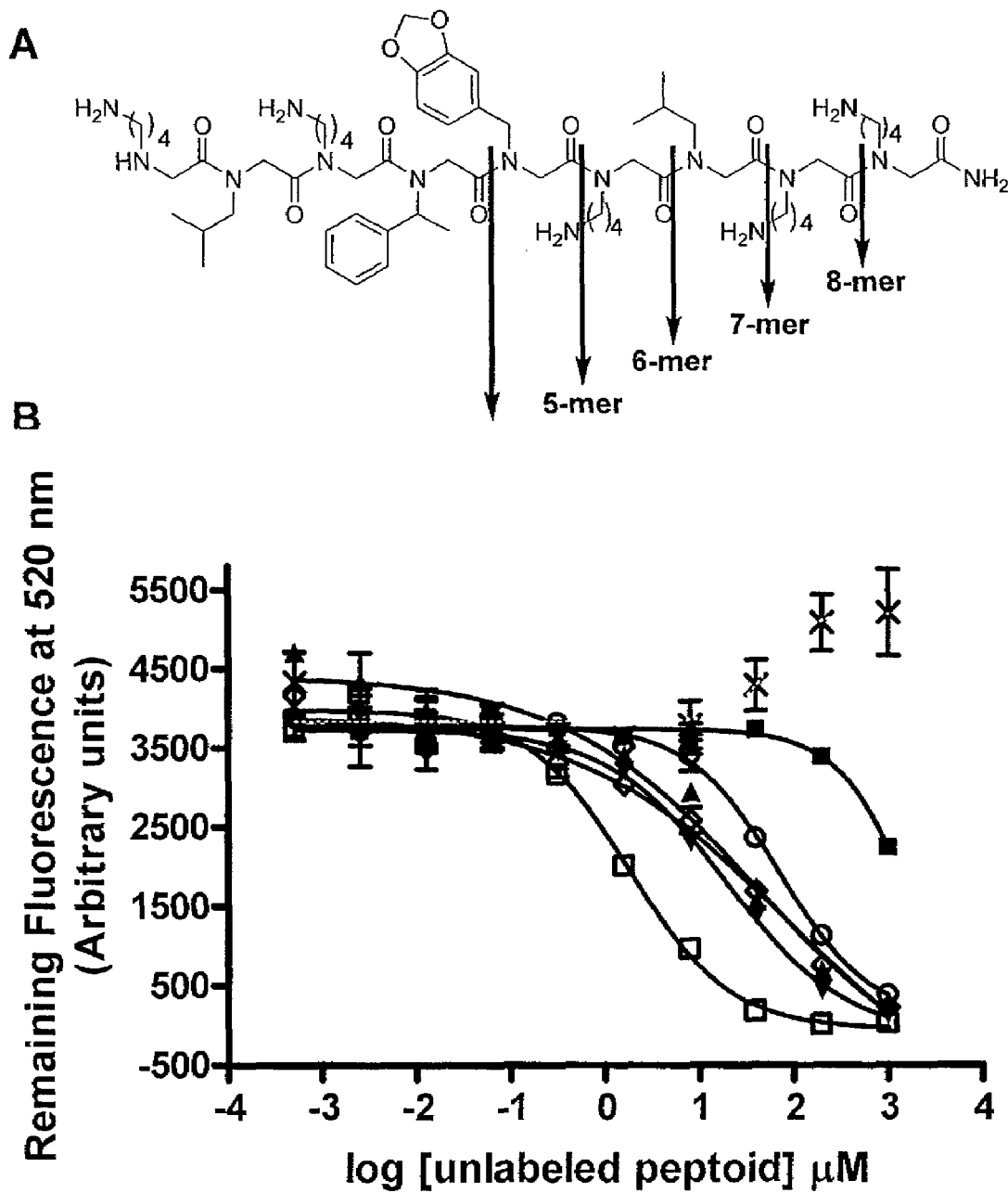
FIGS. 17A-B. GU40C truncation study results.

To identify the main chain amides important for binding, the inventors synthesized five different truncated versions of GU40C, each containing all four of the N-terminal residues (FIG. 17A). Increasing concentrations of these truncated versions were competed with a constant amount of fluoresceinated GU40C for binding to the VEGR2 ECD. The results are shown in FIG. 17B. Unlabeled GU40C competed efficiently with its labeled counterpart as expected (FIG. 17B). Elimination of the first C-terminal residue weakened binding about ten-fold (FIG. 17B). Further elimination of the next three C-terminal residues further diminished binding only slightly. However, deletion of the next residue essentially abolished binding of the peptoid to the VEGFR2 ECD.

Figure 18:
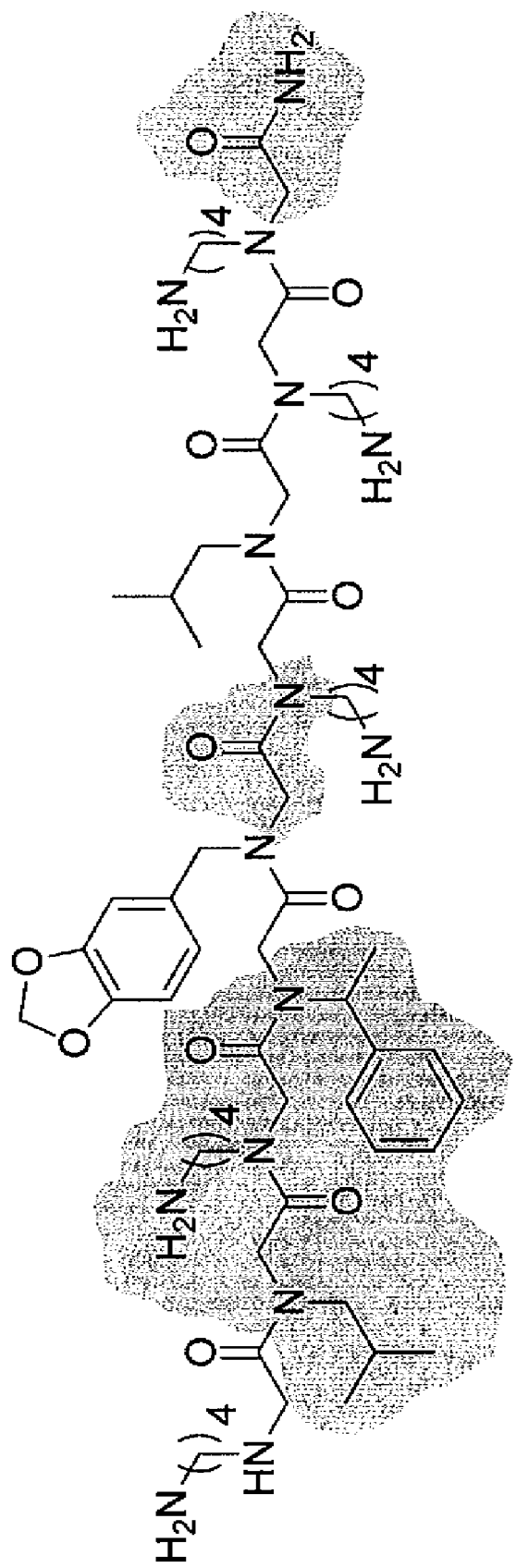
FIG. 18. Structure of the GU40C with highlighted residues that are proposed to constitute the minimal pharmacophore.

In summary, the data described above have defined the minimal pharmacophore of the peptoid VEGFR2 antagonist GU40C4. Only three side chains are important for peptoid-receptor binding (the $6^{th}$ through $8^{th}$ counting from the C-terminus; FIG. 18) as shown by glycine and sarcosine scanning (FIG. 14). However, a smaller peptoid containing only these residues is inactive (FIGS. 15A-B). Furthermore, an analysis of truncated derivatives of GU40C showed that elimination of the first C-terminal residue reduced the affinity of the peptoid by about ten-fold and removal of the fifth residue essentially abolished binding. Combined with the insensitivity of the binding affinity to the removal of the side chains at these residues, these data argue that it is the main chain residues at positions 1 and 5 that contact the receptor ECD. This model is further supported by the fact that the nine residue peptoid GU40C(2), which contains only the side chains at positions 6-8 but is otherwise comprised of glycines, binds the receptor ECD about as well as the GU40C parent.

Figure 19:
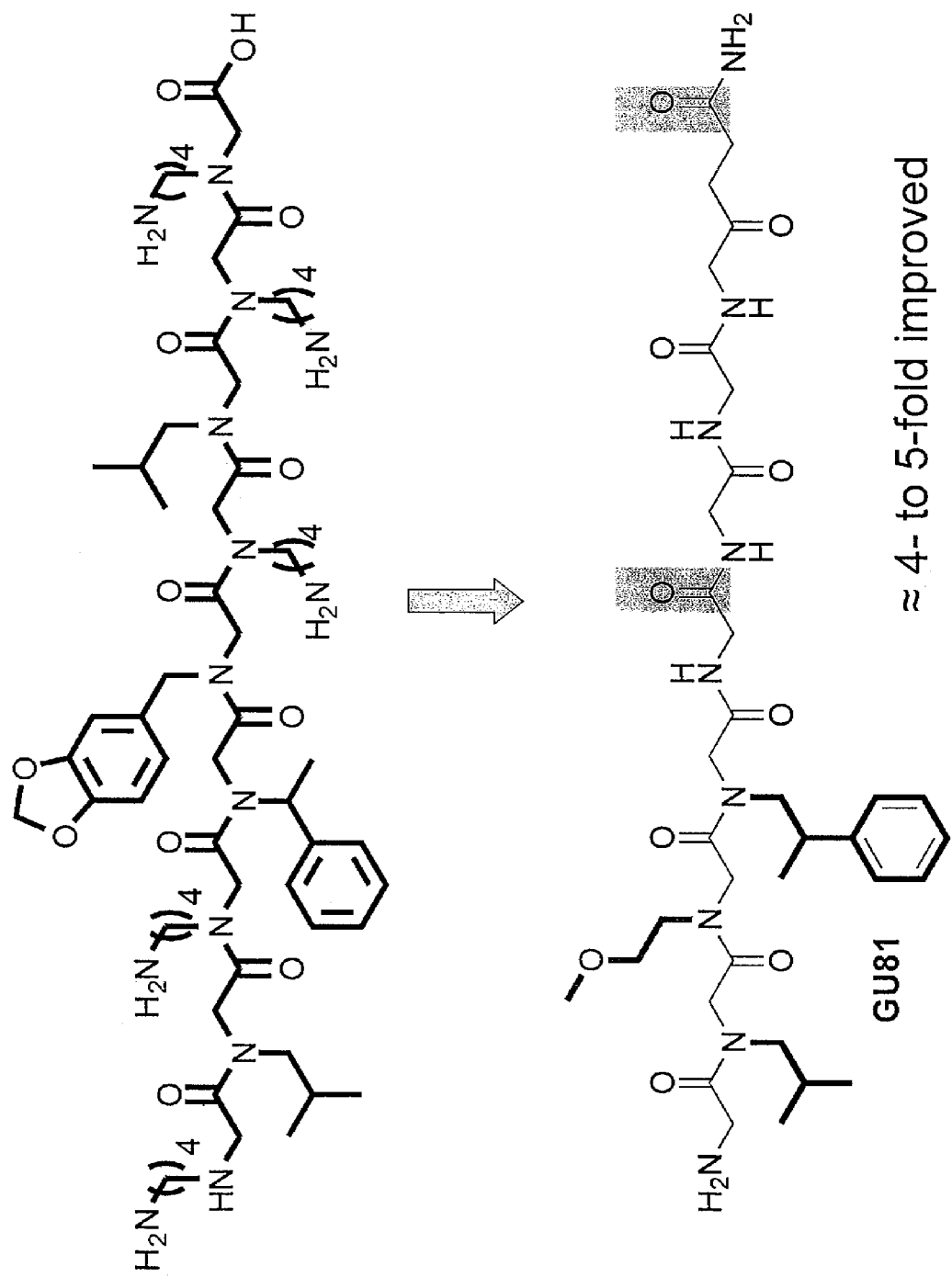
FIG. 19. Chemical structures of GU40C (top) and GU81. GU40C was one of five hits isolated originally from screening a library of ≈250,000 peptoids for specific binding to human VEGFR2. GU81 is the result of a medicinal chemistry exercise aimed at improving the potency of the molecule. This derivative binds the VEGFR2 about 4 times more tightly than the GU40C parent.
Figure 20:
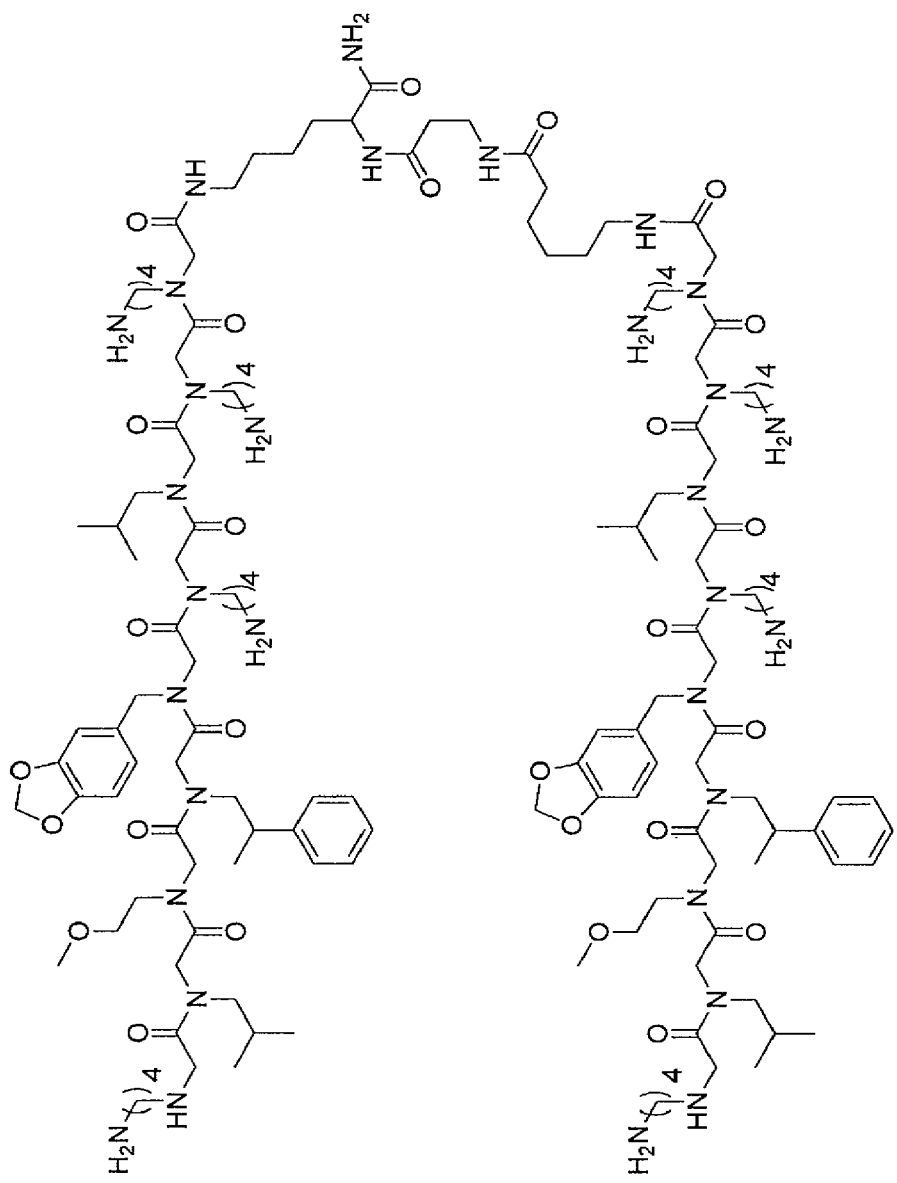
FIG. 20. The chemical structure of the GU81 dimer. This molecule has a high affinity for the VEGFR2 and is a potent antagonist of its activity in vitro and in vivo.
Figure 21:
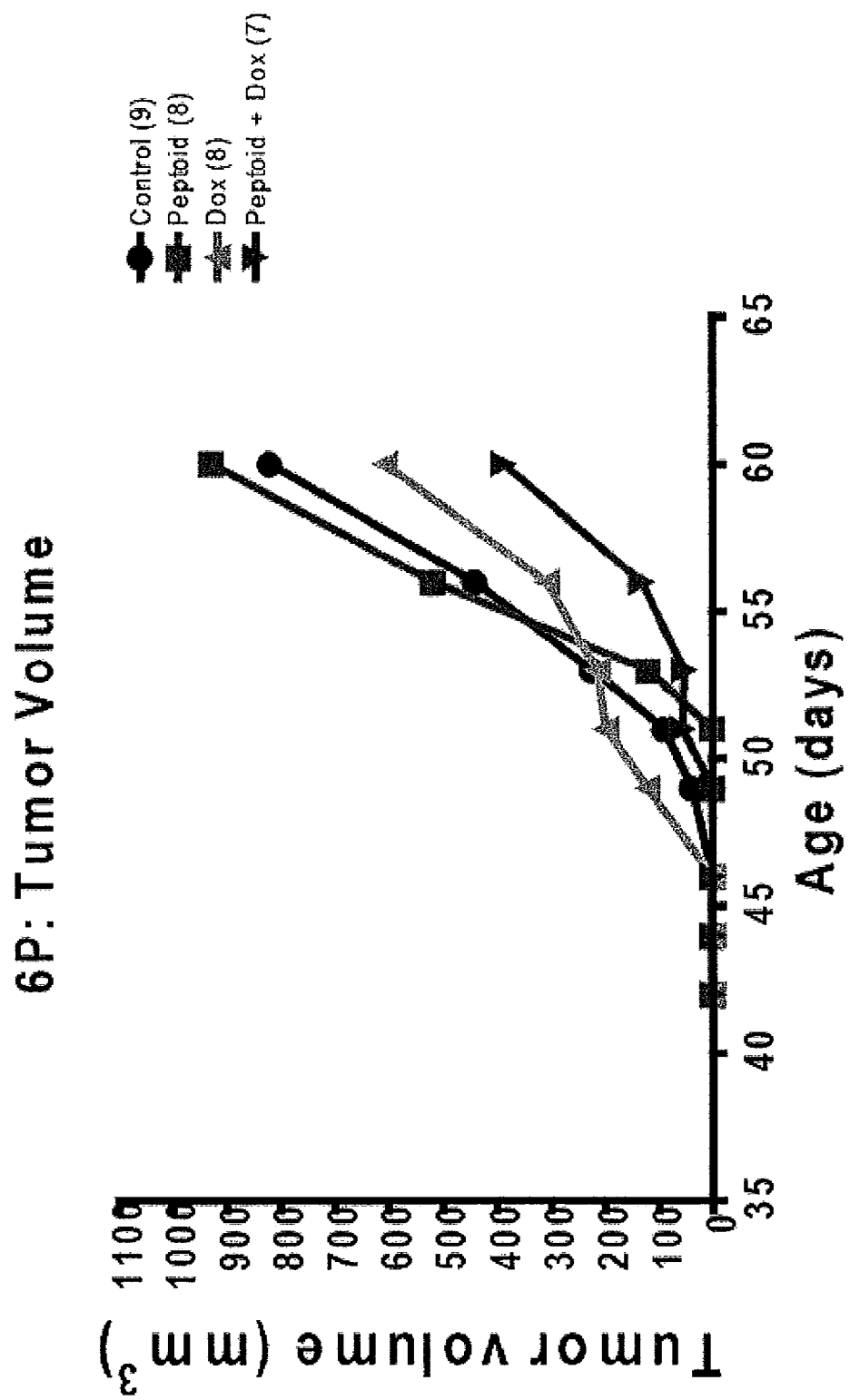
FIG. 21. Effect of doxorubicin (Dox) and the GU81 dimer (peptoid) on the growth of an aggressive MMTV-induced tumor in a mouse. The data show that while the peptoid alone did not result in significant reduction in the rate of tumor growth, it did function synergistically with Dox.
Figure 22:
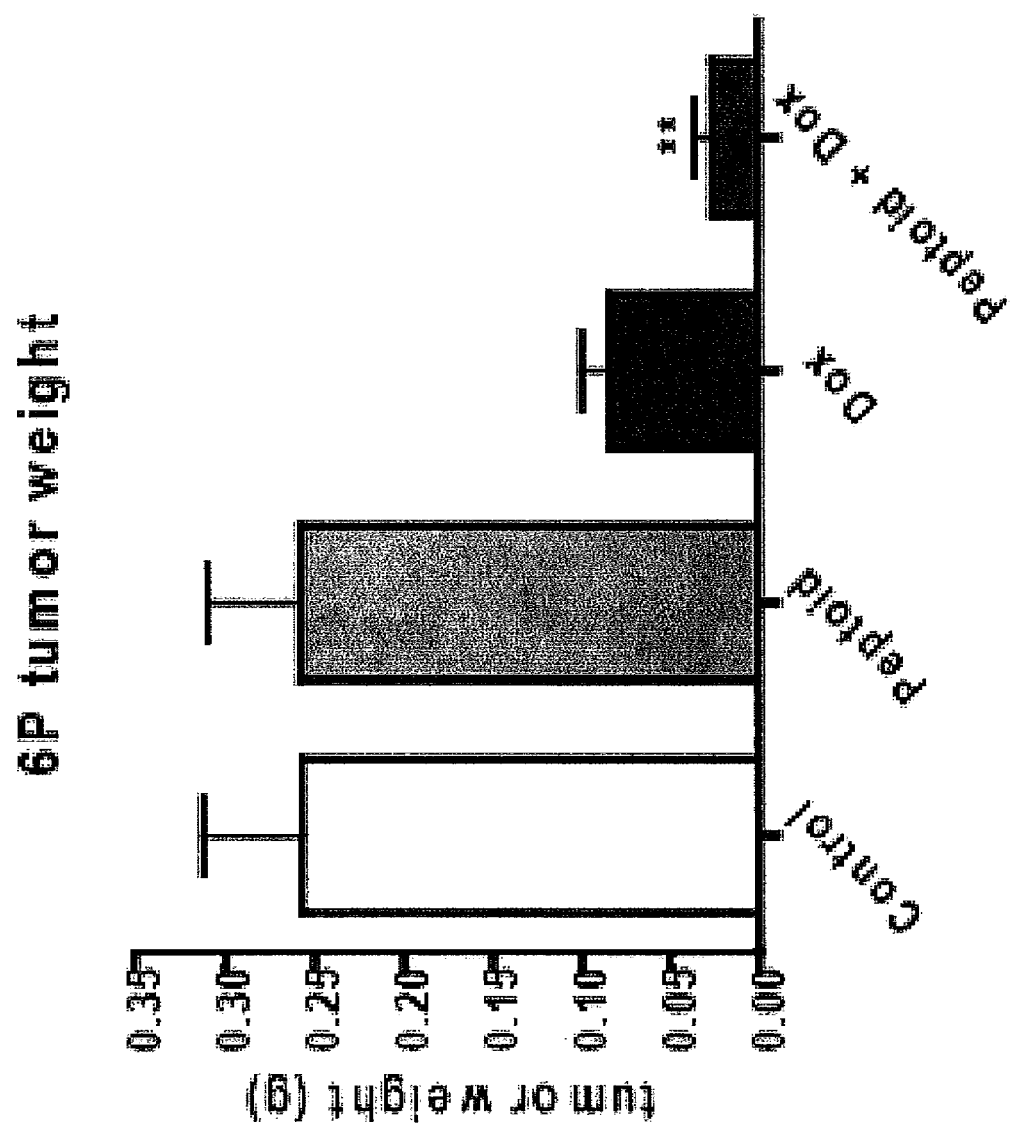
FIG. 22. The effect of Dox and the GU81 dimer on the weight of the MMTV tumor as measured at the time of sacrifice (age 60 days). In agreement with the measurement of tumor volume (see FIG. 21), the peptoid acts synergistically with Dox to reduce the growth of the tumor mass.

GU81 (FIG. 19) is the result of a medicinal chemistry exercise aimed at improving the potency of the molecule. This derivative binds the VEGFR2 about 4 times more tightly than the GU40C parent. The GU81 dimer (FIG. 20) has a high affinity for the VEGFR2 and is a potent antagonist of its activity in vitro and in vivo. FIG. 21 shows the effect of doxorubicin (Dox) and the GU81 dimer (peptoid) on the growth of an aggressive MMTV-induced tumor in a mouse. The data show that while the peptoid alone did not result in significant reduction in the rate of tumor growth, it did function synergistically with Dox. FIG. 22 shows the effect of Dox and the GU81 dimer on the weight of the MMTV tumor as measured at the time of sacrifice (age 60 days). In agreement with the measurement of tumor volume (see FIG. 21), the peptoid acts synergistically with Dox to reduce the growth of the tumor mass.

Example 5

Figure 23:
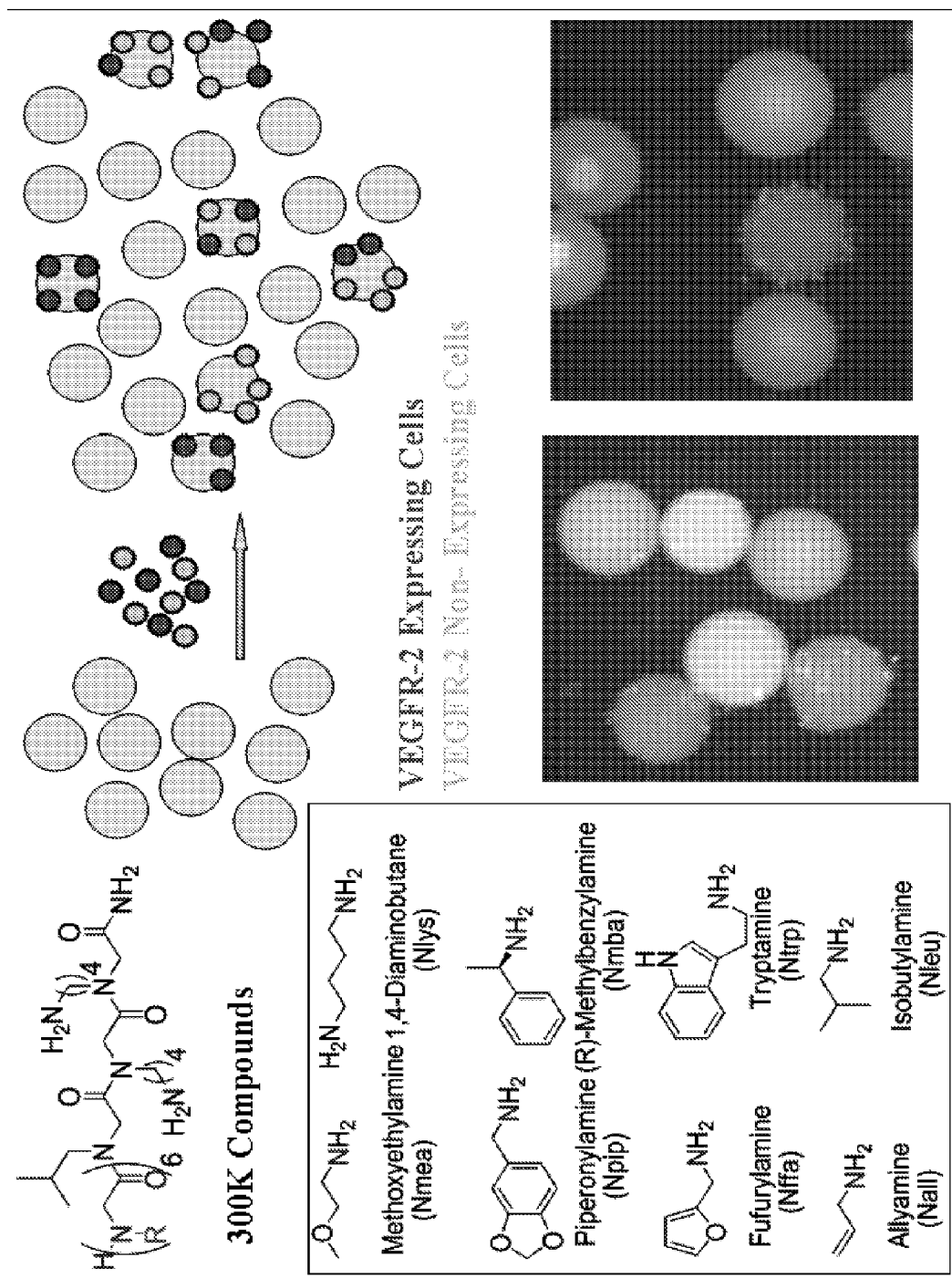
FIG. 23. Schematic of the screening technology and its application to the identification of VEGFR2 ligands.

The inventor sought to develop a rapid and sensitivity screen for agents that bind to pre-selected cell surface structures in a specific fashion. This assays was initially developed using cells expressing the VEGF-2 receptor. Receptor-expressing cells or receptor-null cells were mixed in an approximately 1:1 ratio. The cells were then exposed to a library of molecules displayed on hydrophilic beads (FIG. 23) and after appropriate incubation and washing, the beads that bind only one color cell (red) were picked. The beads were boiled in SDS to remove the cells and other debris and the molecules bound are identified by automated Edman degradation.

This two-color assay demands extremely high specificity, as if the bead-displayed molecule binds any other molecule on the cell surface other than the target receptor, then both colored cells will be retained and the molecule will not be identified as a hit. As evidence of this, the inventors obtained only 5 hits out of 300,000 compounds using the VEGF-2 receptor as the target. Moreover, all of these molecules were later shown to bind the same site on the receptor (Udugamasooriya et al., 2008).

Figure 25:
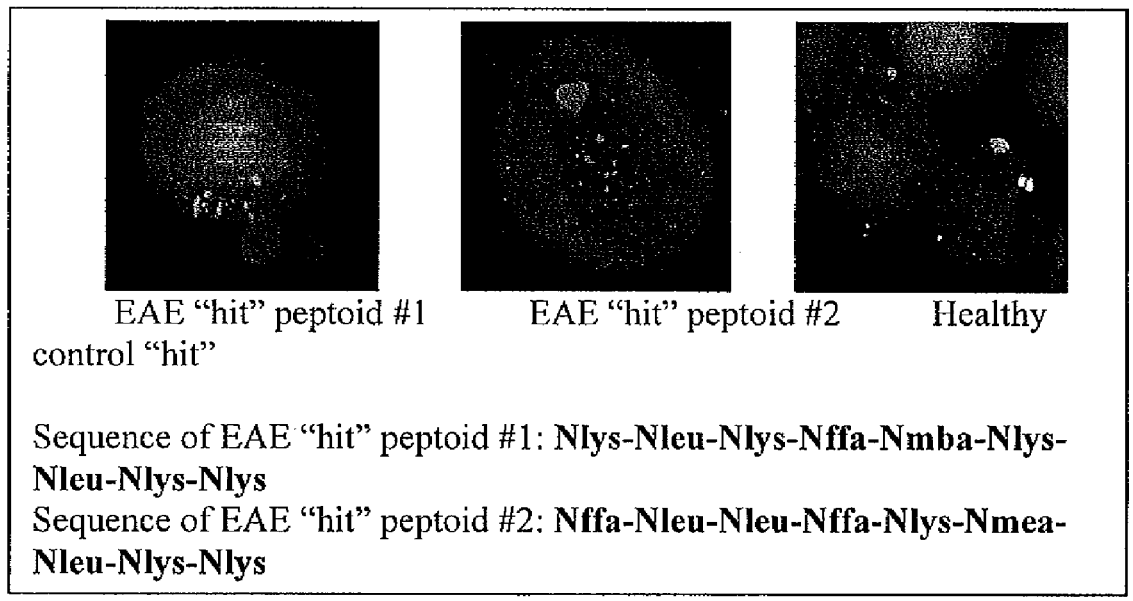
FIG. 25. Results of the screen against two T cell populations. One isolated from EAE mice (labeled red) and the other from healthy control mice (labeled green).

Another example of this assay is shown in FIG. 25, where molecules that bind specifically to autoimmune T cells were identified. Using the general protocol shown in FIG. 23, CD4+ T cells isolated from an animal with an autoimmune disease were labeled with red quantum dots, and CD4+ T cells from a healthy control animal were labeled with green quantum dots. Note that unlike the experiment shown in FIG. 23, this screen is using two different populations of cells. The hypothesis was that the autoimmune T cells involved in disease progression will be present in much higher levels in the autoimmune mouse than in the healthy control. Therefore, the bead library was screened for beads that bind only red T cells (i.e., those isolated from the autoimmune animal). As shown in FIG. 25, when this experiment was performed using mice with EAE, an experimental model of human multiple sclerosis, two peptoids that bound only red cells were identified and sequenced. Subsequent follow-up work (data not shown) revealed that these peptoids also bound a clonal T cell population known to bind the antigen used to initiate this autoimmune disease (a peptide antigen from a nerve sheath protein), providing strong evidence that these peptoids are true hits that recognize autoimmune T cells.

Figure 24:
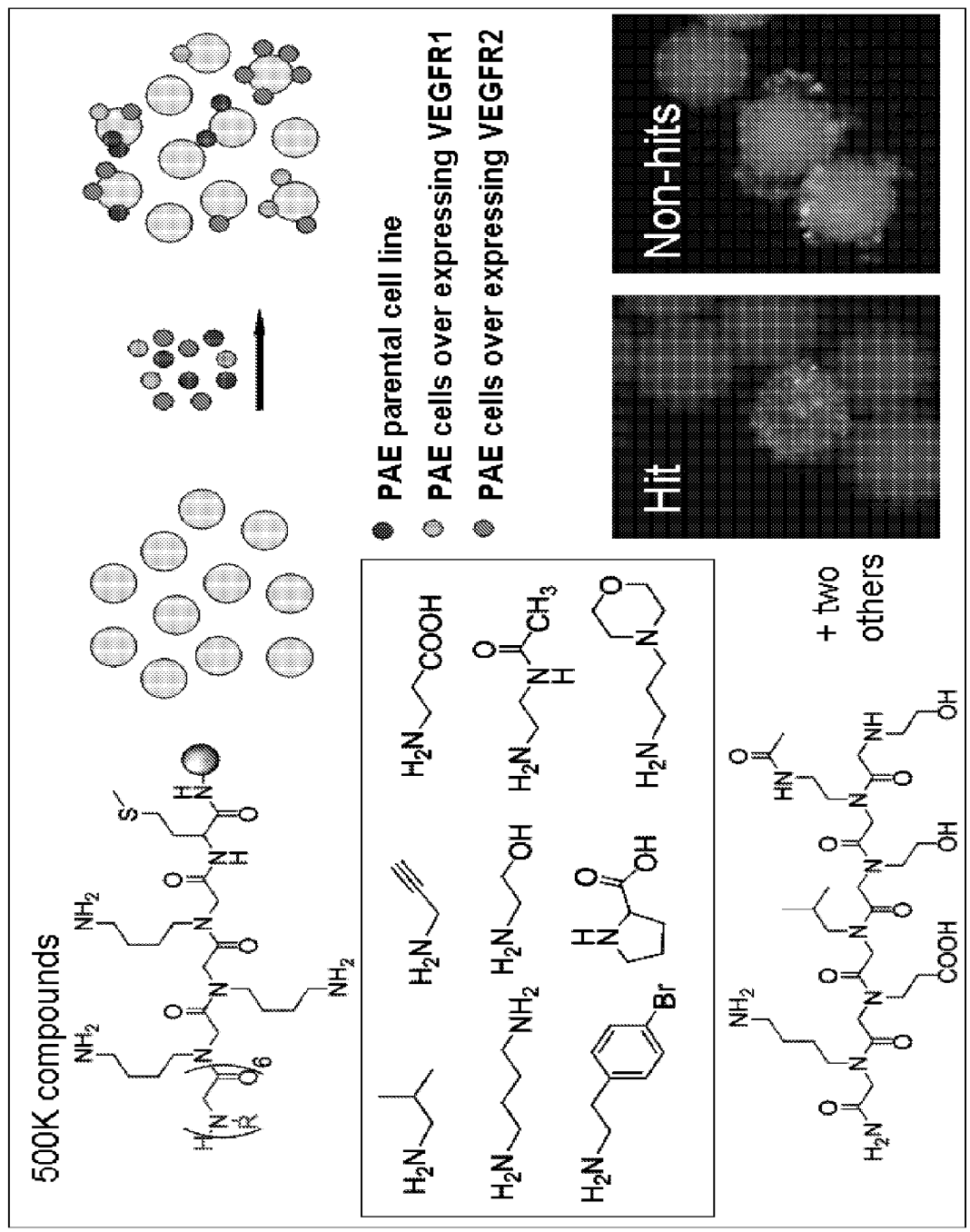
FIG. 24. A three-color assay to identify compounds that discriminate between two closely related receptors.

The assay can be varied in a number of ways to achieve even more specific results. For example, one can screen very large libraries for molecules that distinguish between closely related cell surface receptors. As shown in FIG. 24, the inventor sought to identify of a peptoid capable of binding to VEGFR2, but not VEGFR1. Therefore, a library was synthesized using differing side chains (500,000 compounds) and a three-cell (null, VEGFR2, VEGFR1), three-color screen was performed. This identified three peptoids (the structure of one is shown in FIG. 24) that bound only the VEGFR2-containing cells (labeled green) and not VEGFR1-containing cells (labeled orange) nor the receptor null cells (labeled red).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,680,338
U.S. Pat. No. 5,141,648
U.S. Pat. No. 5,440,013
U.S. Pat. No. 5,446,128
U.S. Pat. No. 5,475,085
U.S. Pat. No. 5,563,250
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,840,833
U.S. Pat. No. 5,856,456
U.S. Pat. No. 5,859,184
U.S. Pat. No. 5,880,270
U.S. Pat. No. 5,929,237
Alluri et al., *J. Amer. Chem. Soc.*, 125:13995-14004, 2003.
Alluri et al, *Mol. BioSystems.*, 2:568-579, 2006.
Ambresin and Mantel, *Rev. Med. Suisse*, 3:137-141, 2007.
Bachhawat-Sikder and Kodadek, *J. Amer. Chem. Soc.*, 125: 9550-9551, 2003.
Binetruy-Tournaire et al., *EMBO J.*, 19:1525-1533, 2000.
Brekken et al., *Cancer Res.*, 58:1952-1959, 1998.
Brekken et al., *Cancer Res.*, 60:5117-5124, 2000.
Cabebe and Wakelee, *Drugs Today (Barc)*, 42:387-398, 2006.
Ciardiello et al., *Expert Opin. Emerg. Drugs*, 8:501-514, 2003.
Clackson and Wells, *Science*, 267:383-386, 1995.
Clark et al., *Clin. Cancer Res.*, 11:5472-5480, 2005.
D'Andrea et al., *Chem. Biol. Drug Des.*, 67:115-126, 2006.
Dvorak, *J. Clin. Oncol.*, 20:4368-4380, 2002.
El Kasmi et al., *Molec. Immunol.*, 35:905, 1998.
Fabian et al., *Nat. Biotechnol.*, 23:329-336, 2005.
Ferrara, *Endocrine Rev.*, 25:581, 2004.
Figliozzi et al., *Methods Enzymol.*, 267:437-447, 1996.
Folkman, *J. Natl. Cancer Inst.*, 82:4-6, 1990.
Fuh et al., *J. Biol. Chem.*, 273:11197-11204, 1998.
Gerber and Ferrara, *Cancer Res.*, 65:671-680, 2005.

Gerber et al., *Cancer Res.*, 60:6253-6258, 2000.
Getmanova et al., *Chem. Biol.*, 13:549-556, 2006.
Hetian et al., *J. Biol. Chem.*, 277:43137-43142, 2002.
Hicklin and Ellis, *J. Clin. Oncol.*, 23:1011-1027, 2005.
Hurwitz et al., *N. Engl. J. Med.*, 350:2335-2342, 2004.
Johannesson et al. *J. Med. Chem.*, 42(22):4524-4537, 1999.
Johnson et al., In: *Biotechnology And Pharmacy*, Pezzuto et al. (Eds.), Chapman and Hall, NY, 1993.
Johnson et al., *J. Clin. Oncol.*, 22:2184-2191, 2004.
Kim et al., *Nature*, 362:841-844, 1993.
Klohs and Hamby, *Curr. Opin. Biotechnol.*, 10:544, 1999.
Kodadek et al., *Acc. Chem. Res.*, 37:711-718, 2004.
Lim et al., *Chem. Commun. (Cambridge, England)*, 1064, 2008.
Liu et al., *Curr. Pharm. Des.*, 13:143-162, 2007.
Liu et al., *J. Amer. Chem. Soc.*, 127:8254-8255, 2005.
Lu et al., *Int. J. Cancer*, 97:393-399, 2002.
Mateo et al., *Hybridoma*, 19:463-471, 2000.
Matthews et al., *Proc. Natl. Acad. Sci. USA*, 88:9026-9030, 1991.
Mattos and Ringe, *Nature Biotechnol.*, 14:595-599, 1996.
Millauer et al., *Cell*, 72:835-846, 1993.
Motzer et al., *J. Clin. Oncol.*, 24:16-24, 2006.
Muller et al., *Proc. Natl. Acad. Sci. USA*, 94:7192-7197, 1997.
Paulick et al., *J. Comb. Chem.*, 8:417-426, 2006.
Peng et al., *Nature Chem. Biol.*, 2:381-389, 2006.
Prewett et al., *Cancer Res.*, 59:5209-5218, 1999.
Reddy et al., *Chem. Biol.*, 11:1127-1137, 2004.
Remington's Pharmaceutical Sciences, 18th Ed. Mack Printing Company, 1990.
Robelek et al., *Angew Chem. Int. Ed. Engl.*, 46:605-608, 2007.
Simon et al., *Proc. Natl. Acad. Sci. USA*, 89:9367-9371, 1992.
Slon-Usakiewicz et al., *Biochemistry*, 36:3494, 1997.
Stevenson, *Leuk. Res.*, 29:239-246, 2005.
Taylor, *Intern. Med.*, 42:15-20, 2003.
Terman et al., *Oncogene*, 6:1677-1683, 1991.
Thomas, *Cancer Nurs.*, 26:21S-25S, 2003.
Udugamasooriya et al., *J. Amer. Chem. Soc.* 130, 5744-5752, 2008.
Vita et al., *Biopolymers*, 47:93-100, 1998.
Wawrzynczak & Thorpe, *Cancer Treat Res.*, 37:239-251, 1988.
Weisshoff et al., *Eur. J. Biochem.*, 259(3):776-788, 1999.
Whitty and Kumaravel, *Nat. Chem. Biol.*, 2:112-118, 2006.
Wiesmann et al., *Cell*, 91:695-704, 1997.
Witte et al., *Cancer Metastasis Rev.*, 17:155-161, 1998.
Zeng et al., *J. Biol. Chem.*, 276:26969-26979, 2001.
Zilberberg et al., *J. Biol. Chem.*, 278:35564-35573, 2003.
Zuckermann et al., *J. Amer. Chem. Soc.*, 114:10646-10647, 1992.
Zuckermann et al., *J. Med. Chem.*, 37:2678-2685, 1994.

What is claimed is:

1. A method of screening a library of peptoid ligands for binding specificity to a cell population mixture comprising:
   (a) providing a peptoid ligand library;
   (b) providing a mixture of cells, wherein said mixture comprises a first cell population of a particular cell type which presents a target cell surface structure and a second cell population of the same or different cell type which does not present the target cell surface structure and wherein the first cell population and the second cell population are differentially labeled with distinct detectable quantum dots;
   (c) contacting said peptoid ligand library with the mixture of cells; and
   (d) determining the binding specificity of the peptoid ligand library by detecting the differentially labeled cell populations bound to the peptoid ligands of the library.

2. The method of claim 1, wherein the peptoid ligands of the library are displayed on a support.

3. The method of claim 1, wherein the cell type of said first cell population is selected from the group comprising a T-cell, a B-cell, an epithelial cell, an endothelial cell, a kidney cell, a cancer cell, a pathogen-infected cell or any other culturable cell type.

4. The method of claim 1, wherein the cell type of said first cell population is a single-celled organism.

5. The method of claim 1, wherein the target cell surface structure comprises an antibody or T-cell receptor, a growth factor receptor, a cell matrix protein, a lectin, a carbohydrate, a lipid or a cell surface antigen.

6. The method of claim 1, wherein at least one of said first and second cell populations is genetically modified.

7. The method of claim 1, wherein the differential label comprises a colorimetric, fluorometric, bioluminescent or chemilluminescent label.

8. The method of claim 2, further comprising identifying the structure or identity of one or more peptoid ligands bound to the differentially labeled cell populations.

9. The method of claim 1, wherein said target cell surface structure is a VEGF2 receptor.

10. The method of claim 1, wherein said target cell surface structure is an antigen.

11. The method of claim 1, wherein said target cell surface structure is a lipid.

12. The method of claim 1, wherein said target cell surface structure is a carbohydrate.

13. The method of claim 1, wherein said quantum dots are internalized into the cells.

14. The method of claim 1, wherein said first cell population and second cell population are B-cell or T-cell types.

15. The method of claim 1, wherein the cell type of said first cell population is a cancer cell.

16. The method of claim 1, wherein the cell type of said first cell population is a pathogen cell or pathogen-infected cell.

17. The method of claim 1, wherein the cell types of said first and second cell populations differ by a specific mutation in a particular gene.

18. The method according to claim 1, wherein the cell type of said first cell population is identical to the cell type of said second cell population.

19. The method of claim 1, wherein said peptoid ligand library has greater than 300,000 distinct oligomers and has at least one monomer selected from the group consisting of:

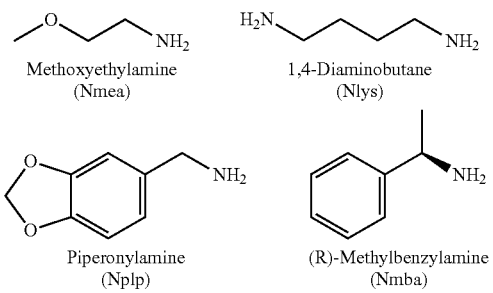

-continued
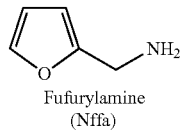
Fufurylamine
(Nffa)
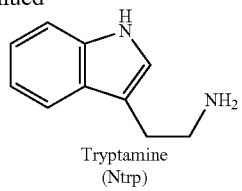
Tryptamine
(Ntrp)
-continued
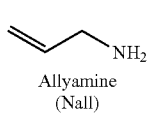
Allyamine
(Nall)
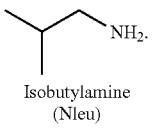
Isobutylamine
(Nleu)
\* \* \* \* \*